United States Patent
Siddiqui-Jain

(10) Patent No.: US 10,772,872 B2
(45) Date of Patent: *Sep. 15, 2020

(54) ANTIMITOTIC AMIDES FOR THE TREATMENT OF CANCER AND PROLIFERATIVE DISORDERS

(71) Applicant: Frost Biologic, Inc., Salt Lake City, UT (US)

(72) Inventor: Adam Siddiqui-Jain, South Jordan, UT (US)

(73) Assignee: Frost Biologic, Inc., Salt Lake City, UT (US)

(*) Notice: Subject to any disclaimer, the term of this patent is extended or adjusted under 35 U.S.C. 154(b) by 0 days.

This patent is subject to a terminal disclaimer.

(21) Appl. No.: 16/024,407

(22) Filed: Jun. 29, 2018

(65) Prior Publication Data

US 2018/0325871 A1 Nov. 15, 2018

Related U.S. Application Data

(63) Continuation of application No. 15/120,470, filed as application No. PCT/US2015/016928 on Feb. 20, 2015, now Pat. No. 10,016,398.

(60) Provisional application No. 61/942,956, filed on Feb. 21, 2014.

(51) Int. Cl.
| | |
|---|---|
| *A61K 31/4178* | (2006.01) |
| *A61K 31/4409* | (2006.01) |
| *C07D 401/14* | (2006.01) |
| *C07D 401/12* | (2006.01) |
| *C07D 405/14* | (2006.01) |
| *C07D 409/14* | (2006.01) |

(52) U.S. Cl.
CPC ...... *A61K 31/4178* (2013.01); *A61K 31/4409* (2013.01); *C07D 401/12* (2013.01); *C07D 401/14* (2013.01); *C07D 405/14* (2013.01); *C07D 409/14* (2013.01); *A61K 2121/00* (2013.01)

(58) Field of Classification Search
CPC .. C07D 401/14; C07D 401/12; C07D 405/14; C07D 409/14
See application file for complete search history.

(56) References Cited

U.S. PATENT DOCUMENTS

| | | | |
|---|---|---|---|
| 6,624,174 B2 | 9/2003 | Manley et al. | |
| 6,995,162 B2 | 2/2006 | Chen et al. | |
| 8,546,403 B2 | 10/2013 | Whitten et al. | |
| 10,016,398 B2* | 7/2018 | Siddiqui-Jain | ....... C07D 401/14 |
| 2009/0156645 A1* | 6/2009 | Dean | ..................... A61K 31/00 |
| | | | 514/343 |
| 2009/0274655 A1 | 11/2009 | Grimes et al. | |
| 2011/0263612 A1 | 10/2011 | Whitten et al. | |

FOREIGN PATENT DOCUMENTS

| | | |
|---|---|---|
| EA | 006973 B1 | 6/2006 |
| JP | 2013525433 | 6/2013 |
| RU | 2296124 C2 | 3/2007 |
| WO | WO 2001/094342 A1 | 12/2001 |
| WO | WO 2008/059042 A1 | 5/2008 |
| WO | WO 2008/125839 A2 | 10/2008 |
| WO | WO 2010/039236 A1 | 4/2010 |
| WO | WO 2010/100475 A1 | 9/2010 |
| WO | WO 2012/107475 A1 | 8/2012 |
| WO | WO 2012/151355 A1 | 11/2012 |
| WO | 2013063385 * | 5/2013 |
| WO | WO 2013/063385 A1 | 5/2013 |

OTHER PUBLICATIONS

CAS Registry No. 1328374-07-7(2011) (Year: 2011).*
Database Registry [Online], Chemical Abstracts Service, Columbus, Ohio, US, Aug. 14, 2011, XP002740103, Database Accession No. 1317573-81-1, Abstract.
Database Registry [Online], Chemical Abstracts Service, Columbus, Ohio, US, Feb. 10, 2015, XP002740104, Database Accession No. 1646329-57-8, Abstract.
International Search Report and Written Opinion for International Patent Application No. PCT/US2015/016928, dated Aug. 21, 2015 (17 pages).

* cited by examiner

*Primary Examiner* — Alexander R Pagano
*Assistant Examiner* — Ebenezer O Sackey
(74) *Attorney, Agent, or Firm* — Barnes & Thornburg LLP

(57) ABSTRACT

Novel, antimitotic heteroaryl amides and pharmaceutically acceptable salts of Formula I where Ar, $R^5$, $R^6$, $R^8$, $R^9$, $R^{11}$, $X^1$, and $X^2$ are as defined herein, as compounds for treatment and prevention of cancer and proliferative diseases and disorders.

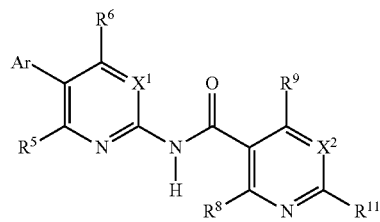

19 Claims, No Drawings

ANTIMITOTIC AMIDES FOR THE TREATMENT OF CANCER AND PROLIFERATIVE DISORDERS

REFERENCE TO EARLIER FILED APPLICATIONS

This application is a continuation of U.S. patent application Ser. No. 15/120,470, filed Aug. 19, 2016, which is a 371 national phase of International Application No. PCT/US2015/016928, filed Feb. 20, 2015, which claims the benefit under 35 U.S.C. § 119(e) of U.S. Provisional Patent Application No. 61/942,956, filed Feb. 21, 2014, the disclosures of which are incorporated, in their entirety, by this reference.

TECHNICAL FIELD OF THE INVENTION

The present invention relates to biologically active chemical compounds, namely heteroaryl amides for treating proliferative disorders such as cancer.

BACKGROUND

Cancer is currently the second leading cause of death in the United States of America, the European Union and Japan and represents a growing world-wide problem. According to the world health organization, annual global cancer deaths are projected to reach 15 million by 2020.

Existing cancer drugs seek to exploit intrinsic differences between cancer cells and normal cells to selectively eradicate the malignant cell population whilst minimizing effects on normal cells that may lead to potentially harmful side-effects. Whereas normal cells are typically quiescent, uncontrolled cellular proliferation is a hallmark of cancer cells and this distinguishing feature underlies the efficacy of most clinically used chemotherapies.

Compounds that directly target cell division or mitosis are amongst the most successful and widely used anti-cancer drugs, either as part of combinatorial drug regimens or as first-line single agent therapies. The most widely used anti-mitotic agents are the taxanes and the *vinca* alkaloids, plant derived natural products, which respectively stabilize and destabilize microtubule networks. In addition to these compounds, other natural product derivatives have recently been approved for cancer treatment including the tubulin stabilizing epothilone, Ixabepilone and the tubulin destabilizing halichondrin-B analog Eribulin. Colchicine, another natural product tubulin polymerization inhibitor is approved for indications other than cancer.

The natural product-based anti-mitotics face a number of intrinsic limitations which severely restrict their clinical utility, including their difficulty of synthesis and/or isolation from natural sources, poor solubility, low bioavailability, systemic toxicities that include neurotoxicity and the development of drug resistance. All or some of these limitations may be overcome by developing synthetic small molecule compounds that work through similar anti-mitotic mechanisms.

Consequently, there remains a great need to develop new, synthetic small molecule anti-mitotic agents that may overcome the limitations of the existing approved natural products and extend the scope and effectiveness of this class of therapeutics.

SUMMARY

Compounds, salts, prodrugs, and solvates of formula I are disclosed,

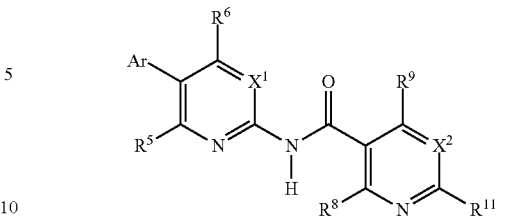

wherein the Ar, $X^1$, $X^2$, $R^5$, $R^6$, $R^8$, $R^9$, and $R^{11}$ have the meanings defined hereafter. The compounds may be used for treatment and prevention of cancer and proliferative diseases and disorders.

In some embodiments, Ar is an optionally substituted phenyl or optionally substituted 5-membered heteroaryl ring, each having 0 to 5 substituents selected from halogen, substituted or unsubstituted $C_{1-8}$ alkyl, substituted or unsubstituted $C_{3-6}$ cycloalkyl, substituted or unsubstituted $C_{2-8}$ alkenyl, substituted or unsubstituted $C_{2-8}$ alkynyl, —CN, —$NO_2$, —C(O)$R^A$, —$CO_2R^A$, —C(O)$NR^AR^B$, —$OR^A$, —OC(O)$R^A$, —OC(O)$NR^AR^B$, —$NR^CC(O)R^A$, —$NR^CC(O)NR^AR^B$, —$NR^AR^B$, —$NR^CCO_2R^A$, —$NR^CS(O)_2R^A$, —$SR^A$, —S(O)$R^A$, —S(O)$_2R^A$, —S(O)$_2NR^AR^B$, substituted or unsubstituted $C_{6-10}$ aryl, substituted or unsubstituted 5- to 10-membered heteroaryl, and substituted or unsubstituted 3- to 10-membered heterocyclyl; provided that when Ar is phenyl, at least one ortho-substitution is —H; $X^1$ is selected from N and $CR^7$; $X^2$ is selected from N and $CR^{10}$; each of $R^5$, $R^6$, $R^7$, $R^{10}$, and $R^{11}$ is independently selected from —H, halogen, substituted or unsubstituted $C_{1-8}$ alkyl, substituted or unsubstituted $C_{2-8}$ alkenyl, substituted or unsubstituted $C_{2-8}$ alkynyl, —CN, —$NO_2$, —C(O)$R^A$, —$CO_2R^A$, —C(O)$NR^AR^B$, —$OR^A$, —OC(O)$R^A$, —OC(O)$NR^AR^B$, —$NR^CC(O)R^A$, —$NR^CC(O)NR^AR^B$, —$NR^AR^B$, —$NR^CCO_2R^A$, —$NR^CS(O)_2R^A$, —$SR^A$, —S(O)$R^A$, —S(O)$_2R^A$, —S(O)$_2NR^AR^B$, substituted or unsubstituted $C_{6-10}$ aryl, substituted or unsubstituted 5- to 10-membered heteroaryl, and substituted or unsubstituted 3- to 10-membered heterocyclyl; each of $R^8$ and $R^9$ is independently selected from H, halogen, —$OR^A$, —$NH_2$, —$NO_2$, —O(CO)$R^A$, —O(CO)$NR^AR^B$, —SH, and —$SR^A$; each of $R^A$, $R^B$, and $R^C$, when present, is independently selected from —H, halogen, substituted or unsubstituted $C_{1-8}$ alkyl, substituted or unsubstituted $C_{3-6}$ cycloalkyl, substituted or unsubstituted $C_{2-8}$ alkenyl, substituted or unsubstituted $C_{2-8}$ alkynyl, —CN, =O, —$NO_2$, —OR', —OC(O)R', —$CO_2$R', —C(O)R', —C(O)NR'R'', —OC(O)NR'R'', —NR'''C(O)R', —NR'''C(O)NR'R'', —NR'R'', —NR'''$CO_2$R', —SR', —S(O)R', —S(O)$_2$R', —S(O)$_2$NR'R'', —NR'S(O)$_2$R'', substituted or unsubstituted $C_{6-10}$ aryl, substituted or unsubstituted 5- to 10-membered heteroaryl, and substituted or unsubstituted 3- to 10-membered heterocyclyl; R', R'', and R''' are each independently —H, unsubstituted $C_{1-4}$ alkyl, substituted or unsubstituted $C_{3-6}$ cycloalkyl, or R' and R'' together with the atoms which they substitute form a substituted or unsubstituted 5-, 6-, or 7-membered ring; provided that when $X^1$ is N, $X^2$ is CH, and Ar is unsubstituted phenyl and each of $R^8$, $R^9$, and $R^{11}$ is hydrogen, then $R^5$ and $R^6$ cannot both be Cl or $OCH_3$; provided that when $X^1$ and $X^2$ are both CH and Ar is unsubstituted phenyl, then at least one of $R^5$, $R^6$, $R^8$, $R^9$, and $R^{11}$ is not hydrogen; provided that when $X^1$ is CH, $X^2$ is C—Cl, Ar is unsubstituted phenyl, and $R^{11}$ is Cl or O-isopropyl, then at least one of $R^5$, $R^6$, $R^8$, and $R^9$ is not hydrogen; and provided that when Ar is 1H-pyrazolo-1-yl, then Ar is not substituted with pyridin-3-yl and trifluoromethyl.

In some embodiments, the compound is of formula II

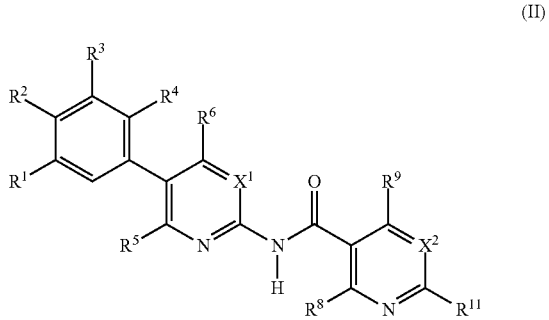

(II)

where $X^1$ is selected from N and $CR^7$; $X^2$ is selected from N and $CR^{10}$; each of $R^1$, $R^2$, $R^3$, and $R^4$ is independently selected from —H, halogen, substituted or unsubstituted $C_{1-8}$ alkyl, substituted or unsubstituted $C_{3-6}$ cycloalkyl, substituted or unsubstituted $C_{2-8}$ alkenyl, substituted or unsubstituted $C_{2-8}$ alkynyl, —CN, —NO$_2$, —C(O)$R^A$, —CO$_2R^A$, —C(O)NR$^A$R$^B$, —OR$^A$, —OC(O)R$^A$, —OC(O)NR$^A$R$^B$, —NR$^C$C(O)R$^A$, —NR$^C$C(O)NR$^A$R$^B$, —NR$^A$R$^B$, —NR$^C$CO$_2R^A$, —NR$^C$S(O)$_2R^A$, —SR$^A$, —S(O)R$^A$, —S(O)$_2R^A$, —S(O)$_2$NR$^A$R$^B$, substituted or unsubstituted $C_{6-10}$ aryl, substituted or unsubstituted 5- to 10-membered heteroaryl, and substituted or unsubstituted 3- to 10-membered heterocyclyl; each of $R^5$, $R^6$, $R^7$, $R^{10}$, and $R^{11}$ is independently selected from —H, halogen, substituted or unsubstituted $C_{1-8}$ alkyl, substituted or unsubstituted $C_{2-8}$ alkenyl, substituted or unsubstituted $C_{2-8}$ alkynyl, —CN, —NO$_2$, —C(O)$R^A$, —CO$_2R^A$, —C(O)NR$^A$R$^B$, —OR$^A$, —OC(O)R$^A$, —OC(O)NR$^A$R$^B$, —NR$^C$C(O)R$^A$, —NR$^C$C(O)NR$^A$R$^B$, —NR$^A$R$^B$, —NR$^C$CO$_2R^A$, —NR$^C$S(O)$_2R^A$, —SR$^A$, —S(O)R$^A$, —S(O)$_2R^A$, —S(O)$_2$NR$^A$R$^B$, substituted or unsubstituted $C_{6-10}$ aryl, substituted or unsubstituted 5- to 10-membered heteroaryl, and substituted or unsubstituted 3- to 10-membered heterocyclyl; each of $R^8$ and $R^9$ is independently selected from —H, halogen, —OR$^A$, —NH$_2$, —NO$_2$, —O(CO)R$^A$, —O(CO)NR$^A$R$^B$, —SH, and —SR$^A$; each of $R^A$, $R^B$, and $R^C$, when present, is independently selected from —H, halogen, substituted or unsubstituted $C_{1-8}$ alkyl, substituted or unsubstituted $C_{3-6}$ cycloalkyl, substituted or unsubstituted $C_{2-8}$ alkenyl, substituted or unsubstituted $C_{2-8}$ alkynyl, —CN, =O, —NO$_2$, —OR', —OC(O)R', —CO$_2$R', —C(O)R', —C(O)NR'R'', —OC(O)NR'R'', —NR'''C(O)R', —NR'''C(O)NR'R'', —NR'R'', —NR'''CO$_2$R', —SR', —S(O)R', —S(O)$_2$R', —S(O)$_2$NR'R'', —NR'S(O)$_2$R'', substituted or unsubstituted $C_{6-10}$ aryl, substituted or unsubstituted 5- to 10-membered heteroaryl and substituted or unsubstituted 3- to 10-membered heterocyclyl; R', R'', and R''' are each independently hydrogen, unsubstituted $C_{1-4}$ alkyl, and substituted or unsubstituted $C_{3-6}$ cycloalkyl or R' and R'' together with the atoms which they substitute form a substituted or unsubstituted 5-, 6-, or 7-membered ring; provided that when $X^1$ is N, $X^2$ is CH, and each of $R^1$, $R^2$, $R^3$, $R^4$, $R^8$, $R^9$, and $R^{11}$ is hydrogen, then $R^5$ and $R^6$ cannot both be Cl or OCH$_3$; provided that when $X^1$ and $X^2$ are both CH, then at least one of $R^1$, $R^2$, $R^3$, $R^4$, $R^5$, $R^6$, $R^8$, $R^9$, and $R^{11}$ is not hydrogen; and provided that when $X^1$ is CH, $X^2$ is C—Cl, and $R^{11}$ is Cl or O-isopropyl, then at least one of $R^1$, $R^2$, $R^3$, $R^4$, $R^5$, $R^6$, $R^8$, and $R^9$ is not hydrogen.

In some embodiments, each of $R^1$, $R^2$, $R^3$, and $R^4$ is independently selected from —H, halogen, substituted or unsubstituted $C_{1-8}$ alkyl, substituted or unsubstituted $C_{3-6}$ cycloalkyl, —C(O)NR$^A$R$^B$, —OR$^A$, —NR$^A$R$^B$, substituted or unsubstituted 5- to 10-membered heteroaryl, and substituted or unsubstituted 3- to 10-membered heterocyclyl. In some embodiments, each of $R^1$, $R^2$, $R^3$, and $R^4$ is —H. In some embodiments, at least one of $R^1$, $R^2$, $R^3$, and $R^4$ is halogen, substituted or unsubstituted $C_{1-8}$ alkyl, substituted or unsubstituted $C_{3-6}$ cycloalkyl, —C(O)NR$^A$R$^B$, —OR$^A$, —NR$^A$R$^B$, —S(O)$_2R^A$, substituted or unsubstituted 5- to 10-membered heteroaryl, or substituted or unsubstituted 3- to 10-membered heterocyclyl. In some embodiments, $R^1$ is selected from —H, chloro, trifluoromethyl, cyclopropyl, —(C=O)NHCH$_3$, —OCH$_3$, —O-cyclopropyl, —NH-cyclopropyl, 1-methyl-piperazin-1-yl, 4-methylpiperazin-1-yl) ethoxyl, phenyl, oxetan-3-yl, cyclobutyl, tert-butyl, —S(O)$_2$-cyclopropyl, piperazin-1-yl, pyrrolidin-3-yl-amino, and —OH; $R^2$ is selected from —H, chloro, and —OCH$_3$; $R^3$ is selected from —H, chloro, cyclopropyl, —(C=O)NHCH$_3$, —OCH$_3$, —O-cyclopropyl, —NH-cyclopropyl, —S(O)$_2$-cyclopropyl, 1-methyl-piperazin-1-yl, 4-methylpiperazin-1-yl)ethoxyl, phenyl, oxetan-3-yl, cyclobutyl, tert-butyl, —S(O)$_2$-cyclopropyl, piperazin-1-yl, pyrrolidin-3-yl-amino, and —OH; and $R^4$ is selected from —H, chloro, trifluoromethyl, and —OCH$_3$; wherein at least one of $R^1$, $R^2$, $R^3$, and $R^4$ is not —H.

In some embodiments, at least one of $R^1$ and $R^3$ is selected from —S(O)$_2$-cyclopropyl and 1-methyl-piperazin-1-yl. In some embodiments, one of $R^1$ and $R^3$ is selected from —S(O)$_2$-cyclopropyl and 1-methyl-piperazin-1-yl and the other of $R^1$ and $R^3$ is selected from —H, —Cl, —S(O)$_2$-cyclopropyl, —NH-cyclopropyl, and cyclopropyl. In some embodiments, at least one of $R^1$ and $R^3$ is —S(O)$_2$-cyclopropyl. In some embodiments, $R^1$ is —S(O)$_2$-cyclopropyl and $R^3$ is —H. In some embodiments, at least one of $R^1$ and $R^3$ is 1-methyl-piperazin-1-yl. In some embodiments, at least one of $R^1$ and $R^3$ is piperazin-1-yl. In some embodiments, at least one of $R^1$ and $R^3$ is —O-cyclopropyl and the other of $R^1$ and $R^3$ is —H. In some embodiments, each of $R^1$ and $R^3$ is selected from cyclopropyl, —O-cyclopropyl, —NH-cyclopropyl, —S(O)$_2$-cyclopropyl, 1-methyl-piperazin-1-yl, piperazin-1-yl, and oxetan-3-yl.

In some embodiments, the compound is of formula III

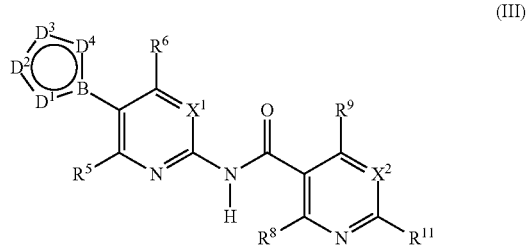

(III)

where $X^1$ is selected from N and $CR^7$; $X^2$ is selected from N and $CR^{10}$; each of $D^1$, $D^2$, $D^3$, and $D^4$ is selected from $CR^1$, $CR^2$, $CR^3$, $CR^4$, N, O, and S; B is selected from C and N; each of $R^1$, $R^2$, $R^3$, and $R^4$ is independently selected from —H, halogen, substituted or unsubstituted $C_{1-8}$ alkyl, substituted or unsubstituted $C_{3-6}$ cycloalkyl, substituted or unsubstituted $C_{2-8}$ alkenyl, substituted or unsubstituted $C_{2-8}$ alkynyl, —CN, —NO$_2$, —C(O)$R^A$, —CO$_2R^A$, —C(O)NR$^A$R$^B$, —OR$^A$, —OC(O)R$^A$, —OC(O)NR$^A$R$^B$, —NR$^C$C(O)R$^A$, —NR$^C$C(O)NR$^A$R$^B$, —NR$^A$R$^B$, —NR$^C$CO$_2R^A$, —NR$^C$S(O)$_2$R$^A$, —SR$^A$, —S(O)R$^A$, —S(O)$_2$R$^A$, —S(O)$_2$NR$^A$R$^B$, substituted or unsubstituted C$_{6-10}$ aryl, substituted or unsubstituted 5- to 10-membered heteroaryl, and substituted or unsubstituted 3- to 10-membered heterocyclyl; each of R$^5$, R$^6$, R$^7$, R$^{10}$, and R$^{11}$ is independently selected from —H, halogen, substituted or unsubstituted C$_{1-8}$ alkyl, substituted or unsubstituted C$_{2-8}$ alkenyl, substituted or unsubstituted C$_{2-8}$ alkynyl, —CN, —NO$_2$, —C(O)R$^A$, —CO$_2$R$^A$, —C(O)NR$^A$R$^B$, —OR$^A$, —OC(O)R$^A$, —OC(O)NR$^A$R$^B$, —NR$^C$C(O)R$^A$, —NR$^C$C(O)NR$^A$R$^B$, —NR$^A$R$^B$, —NR$^C$CO$_2$R$^A$, —NR$^C$S(O)$_2$R$^A$, —SR$^A$, —S(O)R$^A$, —S(O)$_2$R$^A$, —S(O)$_2$NR$^A$R$^B$, substituted or unsubstituted C$_{6-10}$ aryl, substituted or unsubstituted 5- to 10-membered heteroaryl, and substituted or unsubstituted 3- to 10-membered heterocyclyl; each of R$^8$ and R$^9$ is independently selected from —H, halogen, —OR$^A$, —NH$_2$, —NO$_2$, —O(CO)R$^A$, —O(CO)NR$^A$R$^B$, —SH, and —SR$^A$; each of R$^A$, R$^B$, and R$^C$, when present, is independently selected from —H, halogen, substituted or unsubstituted C$_{1-8}$ alkyl, substituted or unsubstituted C$_{3-6}$ cycloalkyl, substituted or unsubstituted C$_{2-8}$ alkenyl, substituted or unsubstituted C$_{2-8}$ alkynyl, —CN, =O, —NO$_2$, —OR', —OC(O)R', —CO$_2$R', —C(O)R', —C(O)NR'R", —OC(O)NR'R", —NR'''C(O)R', —NR'''C(O)NR'R", —NR'R", —NR'''CO$_2$R', —SR', —S(O)R', —S(O)$_2$R', —S(O)$_2$NR'R", —NR'S(O)$_2$R", substituted or unsubstituted C$_{6-10}$ aryl, substituted or unsubstituted 5- to 10-membered heteroaryl and substituted or unsubstituted 3- to 10-membered heterocyclyl; R', R", and R''' are each independently selected from —H, unsubstituted C$_{1-4}$ alkyl, and substituted or unsubstituted C$_{3-6}$ cycloalkyl or R' and R" together with the atoms which they substitute form a substituted or unsubstituted 5-, 6-, or 7-membered ring; provided that when B and D$^1$ are N, then D$^2$ and D$^4$ cannot be C-pyridin-3-yl or C-trifluoromethyl.

In some embodiments, B is C. In some embodiments, each of D$^1$, D$^2$, and D$^4$ is CH and D$^3$ is S. In some embodiments, each of D$^2$, D$^3$, and D$^4$ is CH and D$^1$ is S. In some embodiments, each of D$^1$, D$^3$, and D$^4$ is CH and D$^2$ is O. In some embodiments, each of D$^1$, D$^2$, and D$^3$ is CH and D$^4$ is O.

In some embodiments, X$^1$ is C—H. In some embodiments, X$^1$ is C—F. In some embodiments, X$^2$ is C—H. In some embodiments, X$^2$ is N. In some embodiments, R$^5$ and R$^6$ are both —H. In some embodiments, R$^5$ is —CH$_3$ and R$^6$ is —H. In some embodiments, each of R$^8$ and R$^9$ is independently selected from —H and halogen. In some embodiments, both R$^8$ and R$^9$ is —H. In some embodiments, R$^8$ is fluoro and R$^9$ is —H. In some embodiments, R$^{11}$ is selected from —H, substituted or unsubstituted C$_{1-8}$ alkyl, and —NR$^A$R$^B$. In some embodiments, R$^{11}$ is selected from —H, —CH$_3$, and —NH$_2$. In some embodiments, R$^{11}$ is —H. In some embodiments, R$^{11}$ is —CH$_3$. In some embodiments, R$^{11}$ is —NH$_2$. In some embodiments, X$^1$ is N and R$^7$ is absent.

In one aspect, a pharmaceutical composition having a compound of any one of formulas I-III or any of the compounds disclosed herein and a pharmaceutically acceptable carrier or excipient.

In another aspect, a method of treating an proliferative disorder in a patient in need thereof, includes administering a compound of any one of formulas I-II or any of the compounds disclosed herein or a pharmaceutical composition disclosed herein to the patient. In some embodiments, proliferative disorder is cancer and is selected from adrenal, anal, aplastic anemia, bile duct, bladder, bone, brain, breast, cervical, central nervous system, colon, endometrial, esophagial, ewing family, ocular, gallbladder, gastrointestinal carcinoid, gastrointestinal stromal, Kaposi sarcoma, kidney, laryngeal, leukemia, liver, lung, lymphomas, malignant mesothelioma, multiple myeloma, myelodysplastic syndrome, nasal cavity and paranasal sinus, nasopharyngeal, neuroblastoma, oral cavity and oropharyngeal, osteosarcoma, ovarian, pancreatic, penile, pituitary, prostate, rectal, retinoblastoma, rhabdomyosarcoma, salivary, sarcoma, skin, small intestine, stomach, testicular, thymus, thyroid, uterine sarcoma, vaginal, and Wilms tumor cancers. In some embodiments, the proliferative disorder is a gastric cancer. In some embodiments, the proliferative disorder is selected from Castleman disease, gestational trophoblastic disease, and Hodgkins disease.

DETAILED DESCRIPTION

While the terminology used in this application is standard within the art, the following definitions of certain terms are provided to assure clarity.

Units, prefixes, and symbols may be denoted in their SI accepted form. Numeric ranges recited herein are inclusive of the numbers defining the range and include and are supportive of each integer within the defined range. Unless otherwise noted, the terms "a" or "an" are to be construed as meaning "at least one of." The section headings used herein are for organizational purposes only and are not to be construed as limiting the subject matter described. All documents, or portions of documents, cited in this application, including but not limited to patents, patent applications, articles, books, and treatises, are hereby expressly incorporated by reference in their entirety for any purpose.

The term "alkyl" refers to a saturated, branched or straight-chained or cyclic hydrocarbon radical (group) having from 1 to 16 carbon atoms including, but not limited to, saturated C$_1$-C$_6$ such as: methyl, ethyl, 1-propyl and 2-propyl, 1-butyl, 2-butyl, 2-methyl-1-propyl, 1,1-dimethylethyl, 1-pentyl, 2-pentyl, 3-pentyl, 2-methyl-1-butyl, 3-methyl-1-butyl, 2,2-dimethylpropyl, 1-hexyl, 2-hexyl, 3-hexyl, 2-methyl-1-pentyl, 3-methyl-1-pentyl, 4-methyl-1-pentyl, 3,3-dimethyl-1-butyl, 3,3-dimethyl-2-butyl, 2-ethyl-1-butyl and the like. Alkyl groups may be unsubstituted or substituted. Examples of suitable substituents include, but are not limited to amino, alkylamino, alkoxy, alkylsulfanyl, oxo (=O), halo, acyl, nitro, hydroxyl, cyano, aryl, alkylaryl, aryloxy, arylsulfanyl, arylamino, carbocyclyl, carbocycly loxy, carbocyclylthio, carbocyclylamino, heterocyclyl, heterocyclyloxy, heterocyclylamino, heterocyclylthio, thione (=S), imino (=NR where R can be H, alkyl, acetyl, or aralkyl) and the like.

As used herein, "aralkyl" refers to an aryl group that is attached to another moiety via an alkylene linker. Aralkyl groups can be optionally substituted with one or more substituents.

As used herein, "alkoxy" refers to an OR group, where R is alkyl (substituted or unsubstituted) or aryl. The term "lower alkoxy" refers alkoxy groups having one to six carbon atoms. Alkoxy groups can be optionally substituted with one or more substituents.

As used herein, "alkylene" refers to an alkyl group or a cycloalkyl group that has two points of attachment to two moieties (for example {—CH$_2$-} and {—CH$_2$CH$_2$—} etc.) where the brackets indicate points of attachment. Alkylene groups may be optionally substituted with one more substituents.

As used herein, "aromatic ring" or "aryl" means a monocyclic or polycyclic-aromatic ring or ring radical comprising carbon and hydrogen atoms. Typically, aryl groups have about 6 to about 14 carbon atom ring members. Examples of suitable aryl groups include, but are not limited to, phenyl, anthacenyl, fluorenyl, indenyl, azulenyl, and naphthyl, as well as benzo-fused carbocyclic moieties such as 5,6,7,8-tetrahydronaphthyl. An aryl group can be unsubstituted or substituted with one or more substituents (including without limitation to alkyl or alkyl substituted with one or more halo such as triflouormethyl or hydroxy), hydroxy, alkoxy, alkylsulfanyl, cyano, halo, amino, thiol, thioether, and nitro. In certain embodiments, the aryl group is a monocyclic ring, wherein the ring comprises 6 carbon atoms.

The term "arylalkyl" refers to alkyl substituted with aryl. The aryl portion may be carbocyclic aryl (also referred to as carboaryl), heterocyclic aryl (also referred to as heteroaryl), or biaryl.

The term "alkylsulfanyl," as used herein, refers to an alkyl group which is linked to another moiety though a divalent sulfur atom. Alkylsulfanyl groups can be optionally substituted with one or more substituents.

The term "arylsulfanyl," as used herein, refers to an aryl group which is linked to another moiety though a divalent sulfur atom. Arylsulfanyl groups can be optionally substituted with one or more substituents.

As used herein, the term "alkenyl" means a straight chain or branched, hydrocarbon radical typically having from 2 to 10 carbon atoms and having at least one carbon-carbon double bond. Representative straight chain and branched alkenyls include vinyl, allyl, 1-butenyl, 2-butenyl, isobutylenyl, 1-pentenyl, 2-pentenyl, 3-methyl-1-butenyl, 1-methyl-2-butenyl, 2,3-dimethyl-2-butenyl, 1-hexenyl, 2-hexenyl, 3-hexenyl, 1-heptenyl, 2-heptenyl, 3-heptenyl, 1-octenyl, 2-octenyl, 3-octenyl, 1-nonenyl, 2-nonenyl, 3-nonenyl, 1-decenyl, 2-decenyl, 3-decenyl and the like. Alkenyl groups can be optionally substituted with one or more substituents. Examples of dialkenyl radicals include, but are not limited to, propandiene (allene), 1,3-butadiene, 1,3-pentadiene, 1,4-pentadiene, 2-methyl-1,3-butadiene (isoprene), 3-methyl-1,2-butadiene, 1,3-hexadiene, 1,4-hexadiene, 1,5-hexadiene, 2,4-hexadiene, 2,3-dimethyl-1,3-butadiene, 2-methyl-1,3-pentadiene, 2-methyl-1,4-pentadiene, 3-methyl-1,4-pentadiene, 4-methyl-1,3-pentadiene, 3-methyl-1,3-pentadiene, and the like.

As used herein, the term "alkynyl" means a straight chain or branched, hydrocarbon radical typically having from 2 to 10 carbon atoms and having at least one carbon-carbon triple bond. Representative straight chain and branched alkynyls include acetylenyl, propynyl, 1-butynyl, 2-butynyl, 1-pentynyl, 2-pentynyl, 3-methyl-1-butynyl, 4-pentynyl,-1-hexynyl, 2-hexynyl, 5-hexynyl, 1-heptynyl, 2-heptynyl, 6-heptynyl, 1-octynyl, 2-octynyl, 3-octynyl, 4-octynyl, 7-octynyl, 1-nonynyl, 2-nonynyl, 8-nonynyl, 1-decynyl, 2-decynyl, 5-decynyl, 9-decynyl and the like. Alkynyl groups can be optionally substituted with one or more substituents.

As used herein, "cycloalkyl" means a saturated, mono- or polycyclic alkyl radical typically having from 3 to 14 carbon atoms. In some embodiments, the number of ring carbons is from 3 to 6. Representative cycloalkyls include cyclopropyl, cyclobutyl, cyclopentyl, cyclohexyl, cycloheptyl, cyclooctyl, cyclononyl, cyclodecyl, adamantly, decahydro-naphthyl, octahydropentalene, bicycle[1.1.1]pentanyl, and the like. Cycloalkyl groups can be optionally substituted with one or more substituents. Suitable substituents include halogen, substituted or unsubstituted $C_{1-8}$ alkyl, substituted or unsubstituted $C_{3-6}$ cycloalkyl, substituted or unsubstituted $C_{2-8}$ alkenyl, substituted or unsubstituted $C_{2-8}$ alkynyl, —CN, —NO$_2$, —C(O)R$^A$, —CO$_2$R$^A$, —C(O)NR$^A$R$^B$, —OR$^A$, —OC(O)R$^A$, —OC(O)NR$^A$R$^B$, —NR$^C$C(O)R$^A$, —NR$^C$C (O)NR$^A$R$^B$, —NR$^A$R$^B$, —NR$^C$CO$_2$R$^A$, —NR$^C$S(O)$_2$R$^A$, —SR$^A$, —S(O)R$^A$, —S(O)$_2$R$^A$, —S(O)$_2$NR$^A$R$^B$, substituted or unsubstituted $C_{6-10}$ aryl, substituted or unsubstituted 5- to 10-membered heteroaryl, and substituted or unsubstituted 3- to 10-membered heterocyclyl, where R$^A$, R$^B$, and R$^C$ are further defined here.

As used herein, the term "cycloalkenyl" means a cyclic non-aromatic alkenyl radical having at least one carbon-carbon double bond in the cyclic system and typically having from 5 to 14 carbon atoms. Representative cycloalkenyls include cyclopentenyl, cyclopentadienyl, cyclohexenyl, cyclo-hexadienyl, cycloheptenyl, cycloheptadienyl, cycloheptatrienyl, cyclooctenyl, cyclooctadienyl, cyclooctatrienyl, cyclooctatetraenyl, cyclone-nenyl, cyclo-nonadienyl, cyclodecenyl, cyclodecadienyl and the like. Cycloalkenyl groups can be optionally substituted with one or more substituents.

As used herein, "ester" includes both ROCO— (in the case of R=alkyl, alkoxycarbonyl-) and RCOO— (in the case of R=alkyl, alkylcarbonyloxy-).

As used herein, the term "heterocycle" or "heterocyclyl" means a monocyclic or polycyclic heterocyclic ring (typically having 3- to 14-members) which is either a saturated ring or an unsaturated non-aromatic ring. A 3-membered heterocycle can contain from 1 to 3 heteroatoms, and a 4- to 14-membered heterocycle can contain from 1 to about 8 heteroatoms. Each heteroatom is independently selected from nitrogen, which can be quaternized, oxygen, and sulfur, including sulfoxide and sulfone. The heterocycle may be attached via any heteroatom or carbon atom. Representative heterocycles include morpholinyl, thiomorpholinyl, pyrrolidinonyl, pyrrolidinyl, piperidinyl, piperazinyl, hydantoinyl, valerolactamyl, oxiranyl, oxetanyl, tetrahydrofuranyl, tetrahydropyranyl, 4H-pyranyl, tetrahydropyridinyl, tetrahydropyrimidinyl, tetrahydrothiophenyl, tetrahydrothiopyranyl, and the like. Furthermore, the heterocyclyl may be optionally substituted with one or more substituents (including without limitation to halo, alkyl, haloalkyl, aryl, hydroxyl, amino, alkylamino, dialkylamino, thiol, and alkoxy). Only stable isomers of such substituted heterocyclic groups are contemplated in this definition.

As used herein, the term "heteroaromatic" or "heteroaryl" means a monocyclic or polycyclic heteroaromatic ring (or radical thereof) comprising carbon atom ring members and one or more heteroatom ring members (such as, for example, oxygen, sulfur or nitrogen). Typically, the heteroaromatic ring has from 5 to about 14 ring members in whichours at least 1 ring member is a heteroatom selected from oxygen, sulfur and nitrogen. In another embodiment, the heteroaromatic ring is a 5 or 6 membered ring and may contain from 1 to about 4 heteroatoms. In another embodiment, the heteroaromatic ring system has a 7 to 14 ring members and may contain from 1 to about 7 heteroatoms. Representative heteroaryls include pyridyl, furyl, thienyl, pyrrolyl, oxazolyl, imidazolyl, indolizinyl, thiazolyl, isoxazolyl, pyrazolyl, isothiazolyl, pyridazinyl, pyrimidinyl, pyrazinyl, triazinyl, triazolyl, pyridinyl, thiadiazolyl, pyrazinyl, quinolyl, isoquniolyl, indazolyl, benzoxazolyl, benzofuryl, benzothiazolyl, indolizinyl, imidazopyridinyl, isothiazolyl, tetrazolyl, benzo[1,3]dioxolyl, 2,3-dihydro-benzo[1,4] dioxinyl, benzimidazolyl, benzoxazolyl, benzothiazolyl, benzothiadiazolyl, benzoxadiazolyl, indolyl, tetrahydroindolyl, azaindolyl, imidazopyridyl, qunizaolinyl, purinyl, pyrrolo[2,3]pyrimidyl, pyrazolo[3,4]pyrimidyl or benzo(b) thienyl and the like. Heteroaryl groups may be optionally substituted with one or more substituents like heterocycle.

A heteroaralkyl group refers to a heteroaryl group that is attached to another moiety via an alkylene linker. Heteroaralkyl groups can be substituted or unsubstituted with one or more substituents.

The term "heteroalkyl," as used herein, refers to an alkyl group which has one or more carbons in the alkyl chain replaced with an —O—, —S— or —NR—, wherein R is H or a lower alkyl. Heteroalkyl groups can be optionally substituted with one or more substituents.

As used herein, the term "halogen" or "halo" means —F, —Cl, —Br or —I.

As used herein, the term "haloalkyl" means an alkyl group in which one or more —H is replaced with a halo group. Examples of haloalkyl groups include —$CF_3$, —$CHF_2$, —$CCl_3$, —$CH_2CH_2Br$, —$CH_2CH(CH_2CH_2Br)CH_3$, —$CH_{21}CH_3$, and the like.

As used herein, the term "haloalkoxy" means an alkoxy group in which one or more —H is replaced with a halo group. Examples of haloalkoxy groups include —$OCF_3$ and —$OCHF_2$.

The term "alkylamino," as used herein, refers to an amino group in which one hydrogen atom attached to the nitrogen has been replaced by an alkyl group. The term "dialkylamino," as used herein, refers to an amino group in which two hydrogen atoms attached to the nitrogen have been replaced by alkyl groups, in which the alkyl groups can be the same or different. Alkylamino groups and dialkylamino groups can be optionally substituted with one or more substituents.

The term "fused" when used with aryl or heterocycle refers to the aryl or heterocycle group sharing a common bond with another cyclic group such as a phenyl ring.

The term "cancer" refers to a pathological diseases associated with the growth of transformed cells, and includes the pathological progression of the disease. Thus the term includes cancers of all stages and of all cellular origin. Cancer cells have the capacity for autonomous growth (an abnormal state or condition characterized by rapidly proliferating cell growth). The term is meant to include all types of cancerous growths or oncogenic processes, metastatic tissues or malignantly transformed cells, tissues, or organs, irrespective of histopathologic type, or stage of invasiveness. Examples of cancers include, but are not limited to, carcinoma and sarcoma such as leukemia, sarcomas, osteosarcoma, lymphomas, melanoma, ovarian cancer, skin cancer, testicular cancer, gastric cancer, pancreatic cancer, renal cancer, breast cancer, prostate cancer, colorectal cancer, cancer of the head and neck, brain cancer, esophageal cancer, bladder cancer, adrenal cortical cancer, lung cancer, bronchus cancer, endometrial cancer, nasopharyngeal cancer, cervical or hepatic cancer, or cancer of unknown primary site. In addition, cancer can be associated with a drug resistance phenotype.

As used herein, a "patient" refers to one in need of treatment for diseases and conditions affected by modulating epithelial-mesenchymal transition or is afflicted within one or more of the diseases or conditions described herein or is at a recognized risk of developing one or more of the diseases or conditions described herein as diagnosed by an attending physician or clinician. The identification of those patients who are in need of treatment for the conditions identified herein is well within the ability and knowledge of one skilled in the art. A clinician skilled in the art can readily identify, by the use of clinical tests, physical examination and medical/family history, those patients who are in need of such treatment. A patient includes a warm-blooded animal such as a mammal which is in need of modulated protein kinase activity. It is understood that guinea pigs, dogs, cats, rats, mice, horses, cattle, sheep, and humans are examples of animals within the scope of the meaning of the term.

The terms "treatment," "treating" and "treat," as used herein, include their generally accepted meanings, i.e., the management and care of a patient for the purpose of preventing, reducing the risk in incurring or developing a given condition or disease, prohibiting, restraining, alleviating, ameliorating, slowing, stopping, delaying, or reversing the progression or severity, and holding in check and/or treating existing characteristics, of a disease, disorder, or pathological condition, described herein, including the alleviation or relief of symptoms or complications, or the cure or elimination of the disease, disorder, or condition. The present methods include both medical therapeutic and/or prophylactic treatment, as appropriate.

The terms "hydroxyl" and "hydroxy" both refer to an OH group.

In chemical structures where a carbon-carbon double bond exists (for example olefins), the double bond may be trans (E), or cis (Z).

Where a particular substituent, such as an alkyl substituent, occurs multiple times in a given structure or moiety, the identity of the substituent is independent in each case and may be the same as or different from other occurrences of that substituent in the structure or moiety.

The compounds disclosed herein are defined by their chemical structures and/or chemical names. Where a compound is referred to by both a chemical structure and a chemical name, and the chemical structure and chemical name conflict, the chemical structure is determinative of the compound's identity.

Suitable substituents for an alkyl, alkoxy, alkylsulfanyl, alkylamino, dialkylamino, alkylene, alkenyl, alkynyl, cycloalkyl, cycloalkenyl, heterocyclyl, aryl, aralkyl, heteroaryl, and heteroaralkyl groups include any substituent which will form a stable compound. Examples of substituents for an alkyl, alkoxy, alkylsulfanyl, alkylamino, dialkylamino, alkylene, alkenyl, alkynyl, cycloalkyl, cycloalkenyl, heterocyclyl, aryl, aralkyl, heteroaryl, and heteroaralkyl include: an alkyl, an alkoxy, an alkylsulfanyl, an alkylamino, a dialkylamino, an alkenyl, an alkynyl, a cycloalkyl, a cycloalkenyl, a heterocyclyl, an aryl, a heteroaryl, an aralkyl, a heteraralkyl, a haloalkyl, —C(O)NR'R", —NR'''C(O)R'''', halo, —OR''', cyano, nitro, haloalkoxy, —C(O)R''', —NR'R", —SR''', —C(O)OR''', —OC(O)R''', —NR'''C(O)NR'R", —OC(O)NR'R", —NR'''C(O)OR'''', —S(O)$_p$R''', or —S(O)$_p$NR'R", wherein R' and R", for each occurrence are, independently, H, an alkyl, a cycloalkyl, an alkenyl, an alkynyl, a cycloalkyl, a cycloalkenyl, a heterocyclyl, an aryl, a heteroaryl, an aralkyl, or a heteraralkyl; or R' and R" taken together with the nitrogen to which they are attached is a heterocyclyl or a heteroaryl; and R''' and R'''' for each occurrence are, independently, H, an alkyl, a cycloalkyl, an alkenyl, an alkynyl, a cycloalkyl, a cycloalkenyl, a heterocyclyl, an aryl, a heteroaryl, an aralkyl, or a heteraralkyl.

In addition, alkyl, cycloalkyl, alkylene, a heterocyclyl, and any saturated portion of an alkenyl, cycloalkenyl, alkynyl, aralkyl, and heteroaralkyl groups, may also be substituted with =O, =S, =N—R (where R is —H, an alkyl, acetyl, or aralkyl).

When a heterocyclyl, heteroaryl, or heteroaralkyl group contains a nitrogen atom, it may be substituted or unsubstituted. When a nitrogen atom in the aromatic ring of a heteroaryl group has a substituent the nitrogen may be a quaternary nitrogen.

Choices and combinations of substituents and variables envisioned by this invention are only those that result in the formation of stable compounds. The term "stable", as used herein, refers to compounds which possess stability sufficient to allow manufacture and which maintains the integrity of the compound for a sufficient period of time to be useful for the purposes detailed herein (e.g., therapeutic or prophylactic administration to a subject). Typically, such compounds are stable at a temperature of 40° C. or less, in the absence of excessive moisture, for at least one week. Such choices and combinations will be apparent to those of ordinary skill in the art and may be determined without undue experimentation.

Unless indicated otherwise, the compounds of the invention containing reactive functional groups (such as, without limitation, carboxy, hydroxy, and amino moieties) also include protected derivatives thereof. "Protected derivatives" are those compounds in which a reactive site or sites are blocked with one or more protecting groups. Suitable protecting groups for carboxy moieties include benzyl, tert-butyl, and the like. Suitable protecting groups for amino and amido groups include acetyl, tert-butoxycarbonyl, benzyloxycarbonyl, and the like. Suitable protecting groups for hydroxy include benzyl, trimethylsilyl (TMS) and the like. Other suitable protecting groups are well known to those of ordinary skill in the art and include those found in T. W. Greene, Protecting Groups in Organic Synthesis, John Wiley & Sons, Inc. 1981, the entire teachings of which are incorporated herein by reference.

As used herein and unless otherwise indicated, the term "prodrug" means a derivative of a compound that can hydrolyze, oxidize, or otherwise react under biological conditions (in vitro or in vivo) to provide a compound otherwise disclosed herein. Prodrugs may only become active upon such reaction under biological conditions, but they may have activity in their unreacted forms. Examples of prodrugs contemplated in this invention include, but are not limited to, analogs or derivatives of compounds of any one of formulas I-III, or of Table 1 that comprise biohydrolyzable moieties such as biohydrolyzable amides, biohydrolyzable esters, biohydrolyzable carbamates, biohydrolyzable carbonates, biohydrolyzable ureides, and biohydrolyzable phosphate analogues. Other examples of prodrugs include derivatives of compounds of any one of formulas I-III or of Table 1 that comprise —NO, —NO$_2$, —ONO, or —ONO$_2$ moieties. Prodrugs can typically be prepared using well-known methods, such as those described by 1 Burger's Medicinal Chemistry and Drug Discovery (1995) 172-178, 949-982 (Manfred E. Wolff ed., 5$^{th}$ ed), the entire teachings of which are incorporated herein by reference.

As used herein and unless otherwise indicated, the terms "biohydrolyzable amide", "biohydrolyzable ester", "biohydrolyzable carbamate", "biohydrolyzable carbonate", "biohydrolyzable ureide" and "biohydrolyzable phosphate analogue" mean an amide, ester, carbamate, carbonate, ureide, or phosphate analogue, respectively, that either: 1) does not destroy the biological activity of the compound and confers upon that compound advantageous properties in vivo, such as uptake, duration of action, or onset of action; or 2) is itself biologically inactive but is converted in vivo to a biologically active compound. Examples of biohydrolyzable amides include, but are not limited to, lower alkyl amides, α-amino acid amides, alkoxyacyl amides, and alkylaminoalkylcarbonyl amides. Examples of biohydrolyzable esters include, but are not limited to, lower alkyl esters, alkoxyacyloxy esters, alkyl acylamino alkyl esters, and choline esters. Examples of biohydrolyzable carbamates include, but are not limited to, lower alkylamines, substituted ethylenediamines, aminoacids, hydroxyalkylamines, heterocyclic and heteroaromatic amines, and polyether amines.

As used herein, the term "pharmaceutically acceptable salt," is a salt formed from an acid and a basic group of one of the compounds of any one of formulas I-III or of Table 1. Illustrative salts include, but are not limited, to sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate, and pamoate (i.e., 1,1'-methylene-bis-(2-hydroxy-3-naphthoate)) salts. The term "pharmaceutically acceptable salt" also refers to a salt prepared from a compound of any one of formulas I-III or of Table 1 having an acidic functional group, such as a carboxylic acid functional group, and a pharmaceutically acceptable inorganic or organic base. Suitable bases include, but are not limited to, hydroxides of alkali metals such as sodium, potassium, and lithium; hydroxides of alkaline earth metal such as calcium and magnesium; hydroxides of other metals, such as aluminum and zinc; ammonia, and organic amines, such as unsubstituted or hydroxy-substituted mono-, di-, or trialkylamines; dicyclohexylamine; tributyl amine; pyridine; N-methyl,N-ethylamine; diethylamine; triethylamine; mono-, bis-, or tris-(2-hydroxy-lower alkyl amines), such as mono-, bis-, or tris-(2-hydroxy ethyl)-amine, 2-hydroxy-tert-butylamine, or tris-(hydroxymethyl)methyl-amine, N,N,-di-lower alkyl-N-(hydroxy lower alkyl)-amines, such as N,N-dimethyl-N-(2-hydroxyethyl)amine, or tri-(2-hydroxyethyl)amine; N-methyl-D-glucamine; and amino acids such as arginine, lysine, and the like. The term "pharmaceutically acceptable salt" also refers to a salt prepared from a compound of any one of formulas I-III or of Table 1 having a basic functional group, such as an amino functional group, and a pharmaceutically acceptable inorganic or organic acid. Suitable acids include, but are not limited to, hydrogen sulfate, citric acid, acetic acid, oxalic acid, hydrochloric acid, hydrogen bromide, hydrogen iodide, nitric acid, phosphoric acid, isonicotinic acid, lactic acid, salicylic acid, tartaric acid, ascorbic acid, succinic acid, maleic acid, besylic acid, fumaric acid, gluconic acid, glucaronic acid, saccharic acid, formic acid, benzoic acid, glutamic acid, methanesulfonic acid, ethanesulfonic acid, benzenesulfonic acid, and p-toluenesulfonic acid.

As used herein, the term "pharmaceutically acceptable solvate," is a solvate formed from the association of one or more solvent molecules to one or more molecules of a compound of any one of formulas I-III or of Table 1. The term solvate includes hydrates (e.g., hemi-hydrate, monohydrate, dihydrate, trihydrate, tetrahydrate, and the like).

As used herein, a "proliferative disorder" or a "hyperproliferative disorder," and other equivalent terms, means a disease or medical condition involving pathological growth of cells. Proliferative disorders include cancer, smooth muscle cell proliferation, systemic sclerosis, cirrhosis of the liver, adult respiratory distress syndrome, idiopathic cardiomyopathy, lupus erythematosus, retinopathy (e.g., diabetic retinopathy or other retinopathies), choroidal neovascularisation (e.g., macular degeneration), cardiac hyperplasia, reproductive system associated disorders such as benign prostatic hyperplasia and ovarian cysts, pulmonary fibrosis, endometriosis, fibromatosis, harmatomas, lymphangiomatosis, sarcoidosis, and desmoid tumors.

Smooth muscle cell proliferation includes hyperproliferation of cells in the vasculature, for example, intimal smooth muscle cell hyperplasia, restenosis and vascular occlusion, particularly stenosis following biologically- or mechanically-mediated vascular injury, e.g., vascular injury associated with angioplasty. Moreover, intimal smooth muscle cell hyperplasia can include hyperplasia in smooth muscle other than the vasculature, e.g., bile duct blockage, bronchial airways of the lung in patients with asthma, in the kidneys of patients with renal interstitial fibrosis, and the like.

Non-cancerous proliferative disorders also include hyperproliferation of cells in the skin such as psoriasis and its varied clinical forms, Reiter's syndrome, pityriasis rubra pilaris, and hyperproliferative variants of disorders of keratinization (e.g., actinic keratosis, senile keratosis), scleroderma, and the like.

In some embodiments, the proliferative disorder is cancer. Cancers that can be treated or prevented by the methods disclosed herein include, but are not limited to human sarcomas and carcinomas, e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma; leukemias, e.g., acute lymphocytic leukemia and acute myelocytic leukemia (myeloblastic, promyelocytic, myelomonocytic, monocytic and erythroleukemia); chronic leukemia (chronic myelocytic (granulocytic) leukemia and chronic lymphocytic leukemia); and polycythemia vera, lymphoma (Hodgkin's disease and non-Hodgkin's disease), multiple myeloma, Waldenstrobm's macroglobulinemia, and heavy chain disease.

Antiproliferative Compounds

The present disclosure addresses a need for effective anti-proliferative, anti-mitotic agents to directly treat cancers or to improve the efficacy of other cancer treatments. The disclosure relates to compounds and pharmaceutical compositions that are useful for treating or preventing proliferative disorders, such as cancer.

In one embodiment, compounds of formula I are disclosed (I)

that include pharmaceutically acceptable salts, solvates, and prodrugs, where Ar is an optionally substituted phenyl or optionally substituted 5-membered heteroaryl ring, each having 0 to 5 substituents selected from halogen, substituted or unsubstituted $C_{1-8}$ alkyl, substituted or unsubstituted $C_3$-$C_6$ cycloalkyl, substituted or unsubstituted $C_{2-8}$ alkenyl, substituted or unsubstituted $C_{2-8}$ alkynyl, —CN, —NO$_2$, —C(O)R$^A$, —CO$_2$R$^A$, —C(O)NR$^A$R$^B$, —OR$^A$, —OC(O)R$^A$, —OC(O)NR$^A$R$^B$, —NR$^C$C(O)R$^A$, —NR$^C$C(O)NR$^A$R$^B$, —NR$^A$R$^B$, —NR$^C$CO$_2$R$^A$, —NR$^C$S(O)$_2$R$^A$, —SR$^A$, —S(O)R$^A$, —S(O)$_2$R$^A$, —S(O)$_2$NR$^A$R$^B$, substituted or unsubstituted $C_{6-10}$ aryl, substituted or unsubstituted 5- to 10-membered heteroaryl, and substituted or unsubstituted 3- to 10-membered heterocyclyl; provided that when Ar is phenyl, at least one ortho-substitution is H.

$X^1$ is selected from N and CR$^7$, and $X^2$ is selected from N and CR$^{10}$.

Each of R$^5$, R$^6$, R$^7$, R$^{10}$, and R$^{11}$ is independently selected from —H, halogen, substituted or unsubstituted $C_{1-8}$ alkyl, substituted or unsubstituted $C_{3-8}$ cycloalkyl, substituted or unsubstituted $C_{2-8}$ alkenyl, substituted or unsubstituted $C_{2-8}$ alkynyl, —CN, —NO$_2$, —C(O)R$^A$, —CO$_2$R$^A$, —C(O)NR$^A$R$^B$, —OR$^A$, —OC(O)R$^A$, —OC(O)NR$^A$R$^B$, —NR$^C$C(O)R$^A$, —NR$^C$C(O)NR$^A$R$^B$, —NR$^A$R$^B$, —NRCCO$_2$R$^A$, —NR$^C$S(O)$_2$R$^A$, —SR$^A$, —S(O)R$^A$, —S(O)$_2$R$^A$, —S(O)$_2$NR$^A$R$^B$, substituted or unsubstituted $C_{6-10}$ aryl, substituted or unsubstituted 5- to 10-membered heteroaryl, and substituted or unsubstituted 3- to 10-membered heterocyclyl.

Each of R$^8$ and R$^9$ is independently selected from H, halogen, —OR$^A$, —NH$_2$, —NO$_2$, —O(CO)R$^A$, —O(CO)NR$^A$R$^B$, —SH, and —SR$^A$.

Each of R$^A$, R$^B$, and R$^C$, when present, is independently selected from —H, halogen, substituted or unsubstituted $C_{1-8}$ alkyl, substituted or unsubstituted $C_{3-6}$ cycloalkyl, substituted or unsubstituted $C_{2-8}$ alkenyl, substituted or unsubstituted $C_{2-8}$ alkynyl, —CN, =O, —NO$_2$, —OR', —OC(O)R', —CO$_2$R', —C(O)R', —C(O)NR'R'', —OC(O)NR'R'', —NR'''C(O)R', —NR'''C(O)NR'R'', —NR'R'', —NR'''CO$_2$R', —SR', —S(O)R', —S(O)$_2$R', —S(O)$_2$NR'R'', —NR'S(O)$_2$R'', substituted or unsubstituted $C_{6-10}$ aryl, substituted or unsubstituted 5- to 10-membered heteroaryl, and substituted or unsubstituted 3- to 10-membered heterocyclyl.

Each of R', R'', and R''' are independently hydrogen, unsubstituted $C_{1-4}$ alkyl, and substituted or unsubstituted $C_{3-6}$ cycloalkyl, or R' and R'' together with the atoms which they substitute form a substituted or unsubstituted 5-, 6-, or 7-membered ring.

In compounds of Formula I, the following exclusions may apply:

(1) when $X^1$ is N, $X^2$ is CH, and Ar is unsubstituted phenyl and each of R$^8$, R$^9$, and R$^{11}$ is hydrogen, then R$^5$ and R$^6$ cannot both be Cl or OCH$_3$;

(2) when $X^1$ and $X^2$ are both CH and Ar is unsubstituted phenyl, then at least one of R$^5$, R$^6$, R$^8$, R$^9$, and R$^{11}$ is not hydrogen;

(3) when $X^1$ is CH, $X^2$ is C—Cl, Ar is unsubstituted phenyl, and R$^{11}$ is Cl or O-isopropyl, then at least one of R$^5$, R$^6$, R$^8$, and R$^9$ is not hydrogen;

(4) when Ar is N-(5-(3-(pyridin-3-yl)-5-(trifluoromethyl)-1H-pyrazol-1-yl), $X^1$ is CH, and each of R$^5$, R$^6$, R$^7$, R$^8$, R$^9$, and R$^{11}$ is not hydrogen;

(5) when Ar is N-(5-(3-(pyridin-3-yl)-5-(trifluoromethyl)-1H-pyrazol-1-yl), $X^1$ and $X^2$ are CH, and each of R$^5$, R$^6$, R$^8$ and R$^9$ are H, then R'' is not —OCH$_2$CF$_3$, 2-(pyrrolidin-1-yl)ethoxy, 2-morpholinoethoxy, or cyano; or alternatively to (4) and (5) above, when Ar is 1H-pyrazolo-1-yl, then Ar is not substituted with pyridin-3-yl and trifluoromethyl; or alternatively to all of (1)-(5) above, one or more of the following compounds may be excluded:
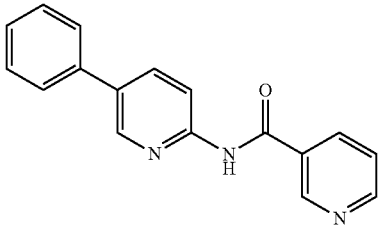
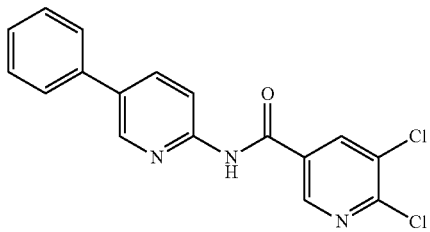
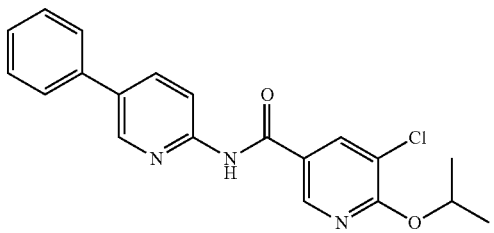
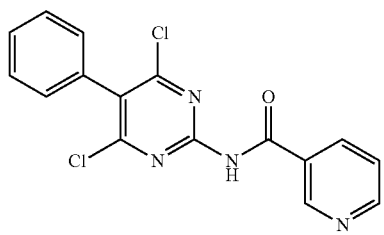
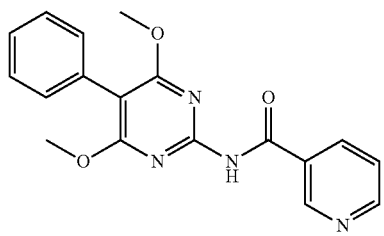
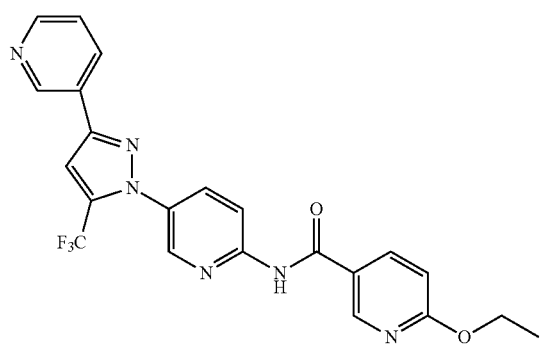
-continued
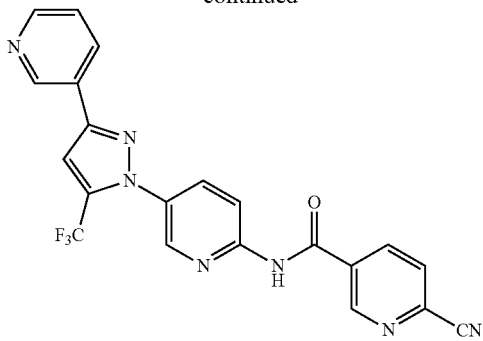
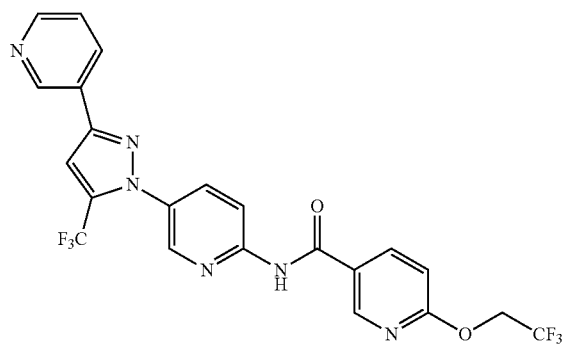
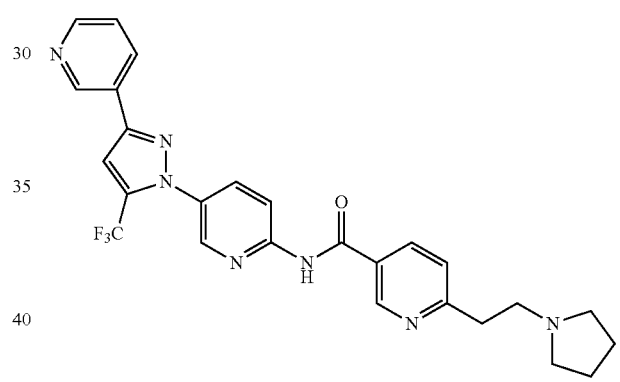
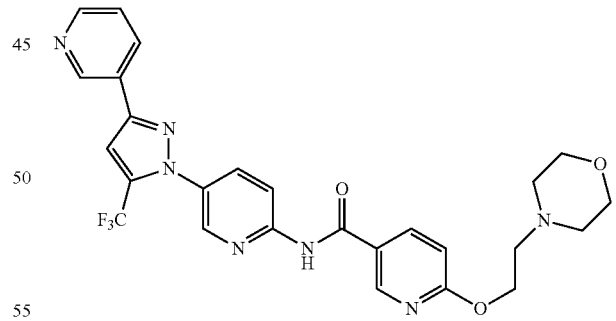
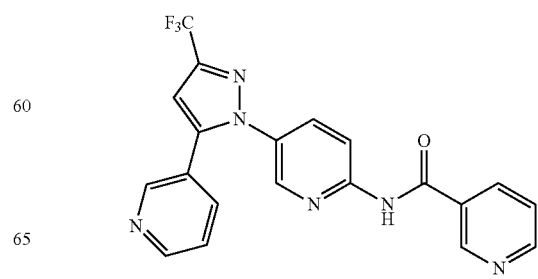

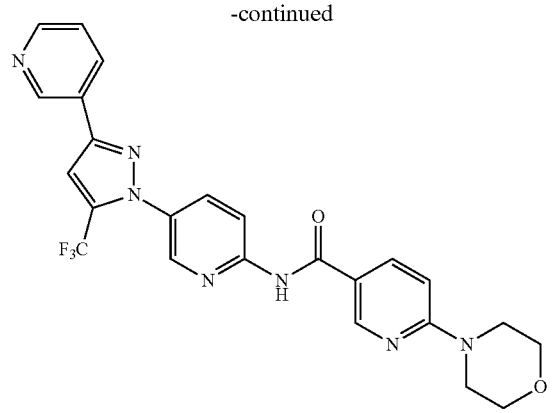
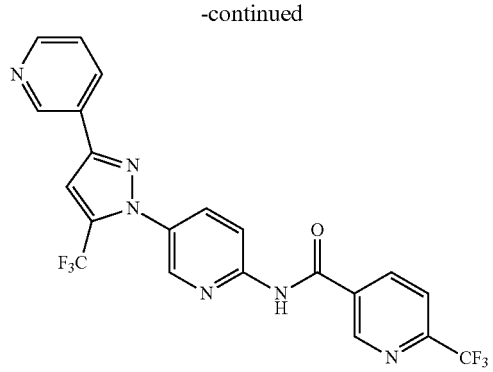
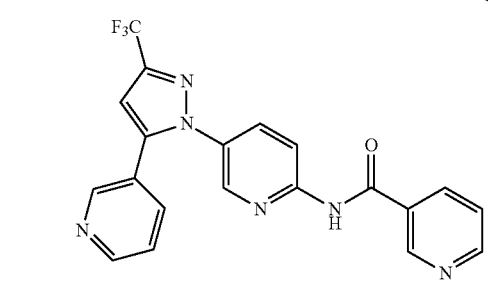
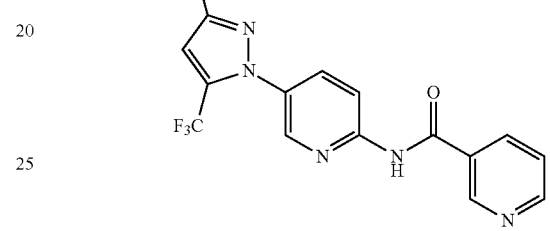
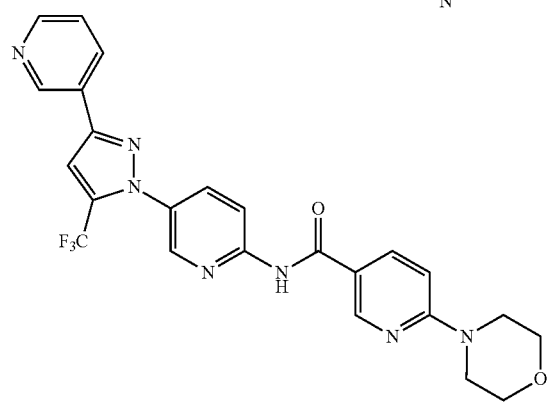
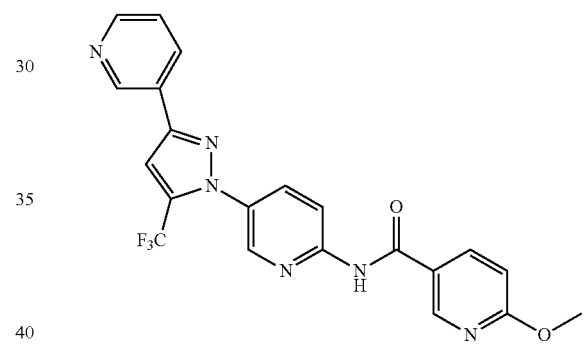
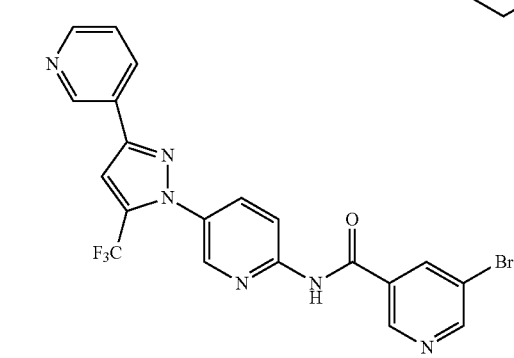
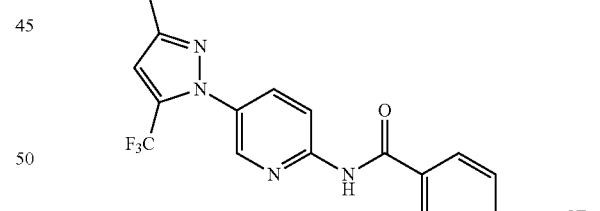
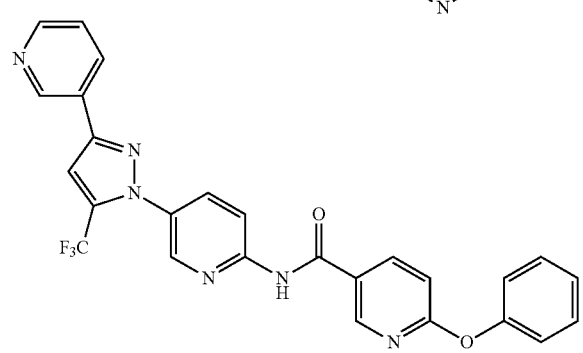
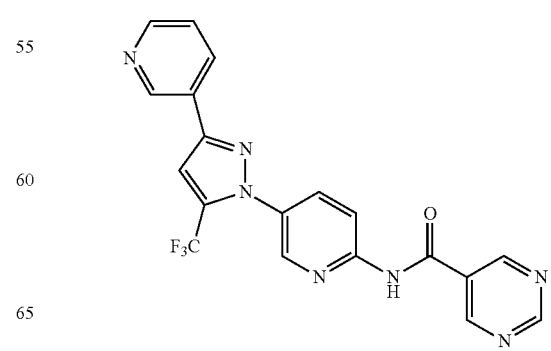

-continued

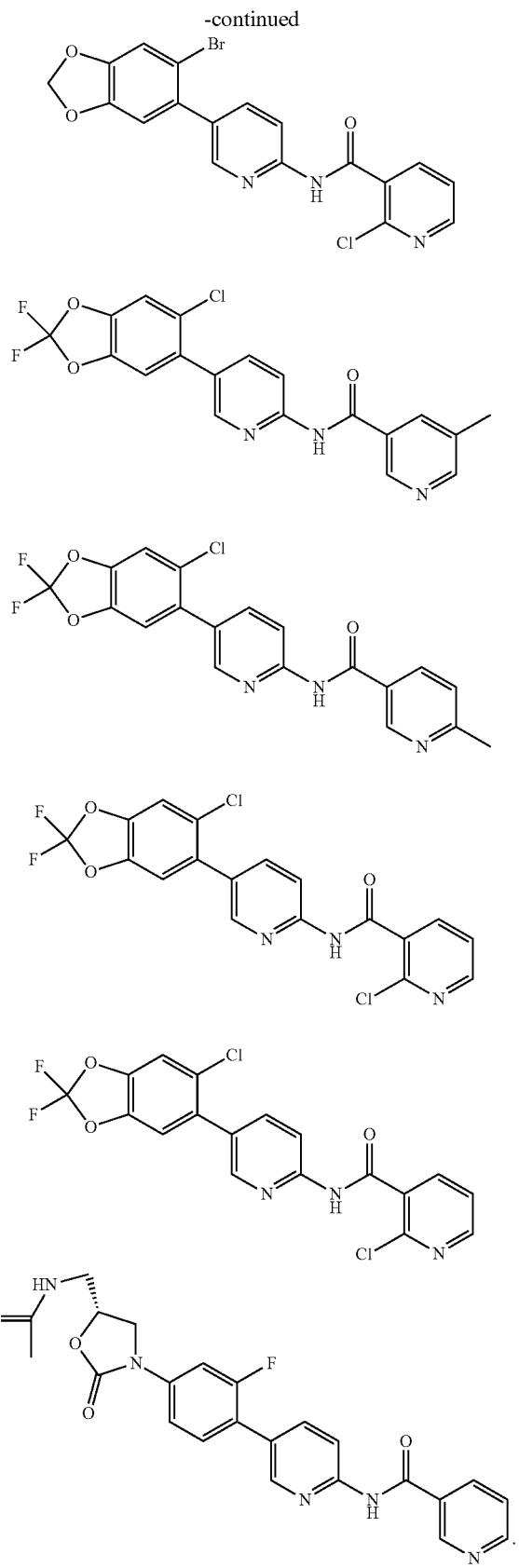

In another embodiment, compounds of formula II are disclosed (II)

that include pharmaceutically acceptable salts, solvates, and prodrugs, where $X^1$ is selected from N and $CR^7$, and $X^2$ is selected from N and $CR^{10}$.

Each of $R^1$, $R^2$, $R^3$, and $R^4$ is independently selected from —H, halogen, substituted or unsubstituted $C_{1-8}$ alkyl, substituted or unsubstituted $C_{3-6}$ cycloalkyl, substituted or unsubstituted $C_{2-8}$ alkenyl, substituted or unsubstituted $C_{2-8}$ alkynyl, —CN, —NO$_2$, —C(O)R$^A$, —CO$_2$R$^A$, —C(O)NR$^A$R$^B$, —OR$^A$, —OC(O)R$^A$, —OC(O)NR$^A$R$^B$, —NR$^C$C(O)R$^A$, —NR$^C$C(O)NR$^A$R$^B$, —NR$^A$R$^B$, —NR$^C$CO$_2$R$^A$, —NR$^C$S(O)$_2$R$^A$, —SR$^A$, —S(O)R$^A$, —S(O)$_2$R$^A$, —S(O)$_2$NR$^A$R$^B$, substituted or unsubstituted $C_{6-10}$ aryl, substituted or unsubstituted 5- to 10-membered heteroaryl, and substituted or unsubstituted 3- to 10-membered heterocyclyl.

Each of $R^5$, $R^6$, $R^7$, $R^{10}$, and $R^{11}$ is independently selected from —H, halogen, substituted or unsubstituted $C_{1-8}$ alkyl, substituted or unsubstituted $C_{2-8}$ alkenyl, substituted or unsubstituted $C_{2-8}$ alkynyl, —CN, —NO$_2$, —C(O)R$^A$, —CO$_2$R$^A$, —C(O)NR$^A$R$^B$, —OR$^A$, —OC(O)R$^A$, —OC(O)NR$^A$R$^B$, —NR$^C$C(O)R$^A$, —NR$^C$C(O)NR$^A$R$^B$, —NR$^A$R$^B$, —NR$^C$CO$_2$R$^A$, —NR$^C$S(O)$_2$R$^A$, —SR$^A$, —S(O)R$^A$, —S(O)$_2$R$^A$, —S(O)$_2$NR$^A$R$^B$, substituted or unsubstituted $C_{6-10}$ aryl, substituted or unsubstituted 5- to 10-membered heteroaryl, and substituted or unsubstituted 3- to 10-membered heterocyclyl.

Each of $R^8$ and $R^9$ is independently selected from —H, halogen, —OR$^A$, —NH$_2$, —NO$_2$, —O(CO)R$^A$, —O(CO)NR$^A$R$^B$, —SH, and —SR$^A$.

Each of $R^A$, $R^B$, and $R^C$, when present, is independently selected from —H, halogen, substituted or unsubstituted $C_{1-8}$ alkyl, substituted or unsubstituted $C_{3-6}$ cycloalkyl, substituted or unsubstituted $C_{2-8}$ alkenyl, substituted or unsubstituted $C_{2-8}$ alkynyl, —CN, =O, —NO$_2$, —OR', —OC(O)R', —CO$_2$R', —C(O)R', —C(O)NR'R'', —OC(O)NR'R'', —NR'''C(O)R', —NR'''C(O)NR'R'', —NR'R'', —NR'''CO$_2$R', —SR', —S(O)R', —S(O)$_2$R', —S(O)$_2$NR'R'', —NR'S(O)$_2$R'', substituted or unsubstituted $C_{6-10}$ aryl, substituted or unsubstituted 5- to 10-membered heteroaryl and substituted or unsubstituted 3- to 10-membered heterocyclyl.

R', R'', and R''' are each independently hydrogen, unsubstituted $C_{1-4}$ alkyl, and substituted or unsubstituted $C_{3-6}$ cycloalkyl, or R' and R'' together with the atoms which they substitute form a substituted or unsubstituted 5-, 6-, or 7-membered ring.

In compounds of Formula II, the following exclusions apply:

(1) when $X^1$ is N, $X^2$ is CH, and each of $R^1$, $R^2$, $R^3$, $R^4$, $R^8$, $R^9$, and $R^{11}$ is hydrogen, then $R^5$ and $R^6$ cannot both be Cl or OCH$_3$;

(2) when $X^1$ and $X^2$ are both CH, then at least one of $R^1$, $R^2$, $R^3$, $R^4$, $R^5$, $R^6$, $R^8$, $R^9$, and $R^{11}$ is not hydrogen;

(3) when $X^1$ is CH, $X^2$ is C—Cl, and $R^{11}$ is Cl or O-isopropyl, then at least one of $R^1$, $R^2$, $R^3$, $R^4$, $R^5$, $R^6$, $R^8$, and $R^9$ is not hydrogen; or alternatively to (1)-(3) above, any one or more of the compounds identified as potential exceptions to formula I above.

In another embodiment, compounds of formula III are disclosed

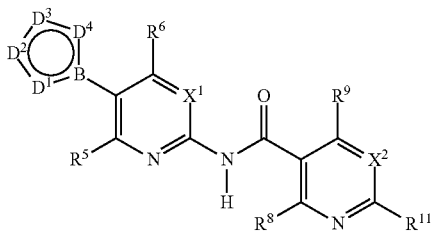

(III)

that include pharmaceutically acceptable salts, solvates, and prodrugs, where $X^1$ is selected from N and $CR^7$, and $X^2$ is selected from N and $CR^{10}$.

Each of $D^1$, $D^2$, $D^3$, and $D^4$ is selected from $CR^1$, $CR^2$, $CR^3$, $CR^4$, N, O, and S. B is selected from C and N.

Each of $R^1$, $R^2$, $R^3$, and $R^4$ is independently selected from —H, halogen, substituted or unsubstituted $C_{1-8}$ alkyl, substituted or unsubstituted $C_{3-6}$ cycloalkyl, substituted or unsubstituted $C_{2-8}$ alkenyl, substituted or unsubstituted $C_{2-8}$ alkynyl, —CN, —$NO_2$, —$C(O)R^A$, —$CO_2R^A$, —$C(O)NR^AR^B$, —$OR^A$, —$OC(O)R^A$, —$OC(O)NR^AR^B$, —$NR^CC(O)R^A$, —$NR^CC(O)NR^AR^B$, —$NR^AR^B$, —$NR^CCO_2R^A$, —$NR^CS(O)_2R^A$, —$SR^A$, —$S(O)R^A$, —$S(O)_2R^A$, —$S(O)_2NR^AR^B$, substituted or unsubstituted $C_{6-10}$ aryl, substituted or unsubstituted 5- to 10-membered heteroaryl, and substituted or unsubstituted 3- to 10-membered heterocyclyl.

Each of $R^5$, $R^6$, $R^7$, $R^{10}$, and $R^{11}$ is independently selected from —H, halogen, substituted or unsubstituted $C_{1-8}$ alkyl, substituted or unsubstituted $C_{2-8}$ alkenyl, substituted or unsubstituted $C_{2-8}$ alkynyl, —CN, —$NO_2$, —$C(O)R^A$, —$CO_2R^A$, —$C(O)NR^AR^B$, —$OR^A$, —$OC(O)R^A$, —$OC(O)NR^AR^B$, —$NR^CC(O)R^A$, —$NR^CC(O)NR^AR^B$, —$NR^AR^B$, —$NR^CCO_2R^A$, —$NR^CS(O)_2R^A$, —$SR^A$, —$S(O)R^A$, —$S(O)_2R^A$, —$S(O)_2NR^AR^B$, substituted or unsubstituted $C_{6-10}$ aryl, substituted or unsubstituted 5- to 10-membered heteroaryl, and substituted or unsubstituted 3- to 10-membered heterocyclyl.

Each of $R^8$ and $R^9$ is independently selected from H, halogen, —$OR^A$, —$NH_2$, —$NO_2$, —$O(CO)R^A$, —$O(CO)NR^AR^B$, —SH, and —$SR^A$.

Each of $R^A$, $R^B$, and $R^C$, when present, is independently selected from —H, halogen, substituted or unsubstituted $C_{1-8}$ alkyl, substituted or unsubstituted $C_{3-6}$ cycloalkyl, substituted or unsubstituted $C_{2-8}$ alkenyl, substituted or unsubstituted $C_{2-8}$ alkynyl, —CN, =O, —$NO_2$, —OR', —OC(O)R', —$CO_2R'$, —C(O)R', —C(O)NR'R'', —OC(O)NR'R'', —NR'''C(O)R', —NR'''C(O)NR'R'', —NR'R'', —$NR'''CO_2R'$, —SR', —S(O)R', —$S(O)_2R'$, —$S(O)_2NR'R''$, —$NR'S(O)_2R''$, substituted or unsubstituted $C_{6-10}$ aryl, substituted or unsubstituted 5- to 10-membered heteroaryl and substituted or unsubstituted 3- to 10-membered heterocyclyl.

R', R'', and R''' are each independently hydrogen, unsubstituted $C_{1-4}$ alkyl, and substituted or unsubstituted $C_{1-6}$ cycloalkyl or R' and R'' together with the atoms which they substitute form a substituted or unsubstituted 5-, 6-, or 7-membered ring.

In compounds of Formula III, the following exclusions apply: (1) when B and $D^1$ are N, $D^2$ is C-3-pyridyl, $D^3$ is CH, and $D^4$ is $C(CF_3)$, $X^1$ is CH, and each of $R^5$, $R^6$, $R^8$, $R^9$, $R^{11}$ are H, then $X^2$ is not N; and (2) when B and $D^1$ are N, $D^2$ is C-3-pyridyl, $D^3$ is CH, and $D^4$ is $C(CF_3)$, $X^1$ and $X^2$ are CH, and each of $R^2$, $R^3$, $R^6$, $R^7$ are H, then $R^5$ is not $OCH_2CF_3$, 2-(pyrrolidin-1-yl)ethoxy, 2-morpholinoethoxy, or cyano;

or alternatively to (1) and (2) above, when B and $D^1$ are N, then $D^2$ and $D^4$ cannot be C-pyridin-3-yl or C-trifluoromethyl.

or alternatively to (1) and (2) above, any one or more of the compounds identified above with respect to formula I above.

In some embodiments of the compounds represented by formulas I-III, $X^1$ is $CR^7$. In some embodiments, $X^1$ is C—H. In some embodiment, $X^1$ is N. In some embodiments, $X^1$ is C—F. In some embodiments, $X^2$ is $CR^{10}$. In some embodiments, $X^2$ is C—H. In some embodiment, $X^2$ is N. In some embodiments, $X^1$ is $CR^7$ and $X^2$ is $CR^{10}$. In some embodiments, $X^1$ and $X^2$ are both C—H. In some embodiments, $X^1$ and $X^2$ are both N. In some embodiments, $X^1$ is $CR^7$ and $X^2$ is N. In some embodiments, $X^1$ is N and $X^2$ is $CR^{10}$. In some embodiments, $X^1$ is CH and $X^2$ is N. In some embodiments, $X^1$ is C—H and $X^2$ is N. In some embodiments, $X^1$ is C—F and $X^2$ is N. In some embodiments, $X^1$ is N and $R^7$ is absent.

In some embodiments of compounds represented by formula III, B is C. In some embodiments, B is N.

In some embodiments of compounds represented by formula III, $D^1$ is $CR^1$. In some embodiments, $D^1$ is N. In some embodiments, $D^1$ is O. In some embodiments, $D^1$ is S.

In some embodiments of compounds represented by formula III, $D^2$ is $CR^2$. In some embodiments, $D^2$ is N. In some embodiments, $D^2$ is O. In some embodiments, $D^2$ is S.

In some embodiments of compounds represented by formula III, $D^3$ is $CR^3$. In some embodiments, $D^3$ is N. In some embodiments, $D^3$ is O. In some embodiments, $D^3$ is S.

In some embodiments of compounds represented by formula III, $D^4$ is $CR^4$. In some embodiments, $D^4$ is N. In some embodiments, $D^4$ is O. In some embodiments, $D^4$ is S.

In some embodiments of compounds represented by formula III, each of $D^1$, $D^2$, and $D^4$ is CH and $D^3$ is S. In some embodiments, each of $D^2$, $D^3$, and $D^4$ is CH and $D^1$ is S. In some embodiments, each of $D^1$, $D^3$, and $D^4$ is CH and $D^2$ is O. In some embodiments, each of $D^1$, $D^2$, and $D^3$ is CH and $D^4$ is O.

In some embodiments of the compounds represented by formulas II and III, $R^1$ is H. In some embodiments, $R^1$ is halogen. In some embodiments, $R^1$ is substituted or unsubstituted $C_{1-8}$ alkyl. In some embodiments, $R^1$ is unsubstituted $C_{1-8}$ alkyl. In some embodiments, $R^1$ is substituted $C_{1-8}$ alkyl. In some embodiments, $R^1$ is cycloalkyl. In some embodiments, $R^1$ is cyclopropyl. In some embodiments, $R^1$ is substituted or unsubstituted $C_{3-6}$ cycloalkyl. In some embodiments, $R^1$ is substituted $C_{3-6}$ cycloalkyl. In some embodiments, $R^1$ is unsubstituted $C_{3-6}$ cycloalkyl. In some embodiments, $R^1$ is substituted or unsubstituted $C_{2-8}$ alkenyl. In some embodiments, $R^1$ is unsubstituted $C_{2-8}$ alkenyl. In some embodiments, $R^1$ is substituted $C_{2-8}$ alkenyl. In some embodiments, $R^1$ is substituted or unsubstituted $C_{2-8}$ alkynyl. In some embodiments, $R^1$ is unsubstituted $C_{2-8}$ alkynyl. In some embodiments, $R^1$ is substituted $C_{2-8}$ alkynyl. In some embodiments, $R^1$ is —CN. In some embodiments, $R^1$ is —$NO_2$. In some embodiments, $R^1$ is —$C(O)R^A$. In some embodiments, $R^1$ is —$CO_2R^A$. In some embodiments, $R^1$ is —$C(O)NR^AR^B$. In some embodiments, $R^1$ is —OR$^A$. In some embodiments, R$^1$ is —OC(O)R$^A$. In some embodiments, R$^1$ is —OC(O)NR$^A$R$^B$. In some embodiments, R$^1$ is —NR$^C$C(O)R$^A$. In some embodiments, R$^1$ is —R$^C$C(O) NR$^A$R$^B$. In some embodiments, R$^1$ is —NR$^A$R$^B$. In some embodiments, R$^1$ is —NR$^C$CO$_2$R$^A$. In some embodiments, R$^1$ is —NR$^C$S(O)$_2$R$^A$. In some embodiments, R$^1$ is —SR$^A$. In some embodiments, R$^1$ is —S(O)R$^A$. In some embodiments, R$^1$ is —S(O)$_2$R$^A$. In some embodiments, R$^1$ is —S(O)$_2$NR$^A$R$^B$. In some embodiments, R$^1$ is substituted or unsubstituted C$_{6-10}$ aryl. In some embodiments, R$^1$ is substituted C$_{6-10}$ aryl. In some embodiments, R$^1$ is unsubstituted C$_{6-10}$ aryl. In some embodiments, R$^1$ is substituted or unsubstituted 5- to 10-membered heteroaryl. In some embodiments, R$^1$ is substituted 5- to 10-membered heteroaryl. In some embodiments, R$^1$ is unsubstituted 5- to 10-membered heteroaryl. In some embodiments, R$^1$ is substituted or unsubstituted 3- to 10-membered heterocyclyl. In some embodiments, R$^1$ is substituted 3- to 10-membered heterocyclyl. In some embodiments, R$^1$ is unsubstituted 3- to 10-membered heterocyclyl.

In some embodiments of compounds represented by formulas II and III, R$^1$ is selected from: —H, halogen, substituted or unsubstituted C$_{1-8}$ alkyl, substituted or unsubstituted C$_{3-6}$ cycloalkyl, —C(O)NR$^A$R$^B$, —OR$^A$, —NR$^A$R$^B$, —S(O)$_2$R$^A$, substituted or unsubstituted 5- to 10-membered heteroaryl, and substituted or unsubstituted 3- to 10-membered heterocyclyl.

In some embodiments of compounds represented by formulas II and III, R$^1$ is selected from: —H, chloro, trifluoromethyl, cyclopropyl, —C=O)NHCH$_3$, —OCH$_3$, —O-cyclopropyl, —NH-cyclopropyl, 1-methyl-piperazin-1-yl, 4-methylpiperazin-1-yl)ethoxyl, phenyl, oxetan-3-yl, cyclobutyl, tert-butyl, —S(O)$_2$-cyclopropyl, piperazinyl-1-yl, pyrrolidiny-3-yl-amino, and —OH. In some embodiments, R$^1$ is —H. In some embodiments, R$^1$ is chloro. In some embodiments, R$^1$ is trifluoromethyl. In some embodiments, R$^1$ is cyclopropyl. In some embodiments, R$^1$ is —(C=O)NHCH$_3$. In some embodiments, R$^1$ is —OCH$_3$. In some embodiments, R$^1$ is —O-cyclopropyl. In some embodiments, R$^1$ is —NH-cyclopropyl. In some embodiments, R$^1$ is 1-methyl-piperazin-1-yl. In some embodiments, R$^1$ is 4-methylpiperazin-1-yl)ethoxyl. In some embodiments, R$^1$ is phenyl. In some embodiments, R$^1$ is oxetan-3-yl. In some embodiments, R$^1$ is cyclobutyl. In some embodiments, R$^1$ is and tert-butyl. In some embodiments, R$^1$ is —S(O)$_2$-cyclopropyl. In some embodiments, R$^1$ is piperazinyl-1-yl. In some embodiments, R$^1$ is pyrrolidiny-3-yl-amino. In some embodiments, R$^1$ is —OH.

In some embodiments of compounds represented by formulas II and III, R$^2$ is —H. In some embodiments, R$^2$ is halogen. In some embodiments, R$^2$ is substituted or unsubstituted C$_{1-8}$ alkyl. In some embodiments, R$^2$ is cycloalkyl. In some embodiments, R$^2$ is cyclopropyl. In some embodiments, R$^2$ is substituted or unsubstituted C$_{3-6}$ cycloalkyl. In some embodiments, R$^2$ is substituted C$_{3-6}$ cycloalkyl. In some embodiments, R$^2$ is unsubstituted C$_{3-6}$ cycloalkyl. In some embodiments, R$^2$ is unsubstituted C$_{1-8}$ alkyl. In some embodiments, R$^2$ is substituted C$_{1-8}$ alkyl. In some embodiments, R$^2$ is substituted or unsubstituted C$_{2-8}$ alkenyl. In some embodiments, R$^2$ is unsubstituted C$_{2-8}$ alkenyl. In some embodiments, R$^2$ is substituted C$_{2-8}$ alkenyl. In some embodiments, R$^2$ is substituted or unsubstituted C$_{2-8}$ alkynyl. In some embodiments, R$^2$ is unsubstituted C$_{2-8}$ alkynyl. In some embodiments, R$^2$ is substituted C$_{2-8}$ alkynyl. In some embodiments, R$^2$ is —CN. In some embodiments, R$^2$ is —NO$_2$. In some embodiments, R$^2$ is —C(O)R$^A$. In some embodiments, R$^2$ is —CO$_2$R$^A$. In some embodiments, R$^2$ is —C(O)NR$^A$R$^B$. In some embodiments, R$^2$ is —OR$^A$. In some embodiments, R$^2$ is —OC(O)R$^A$. In some embodiments, R$^2$ is —OC(O)NR$^A$R$^B$. In some embodiments, R$^2$ is —NR$^C$C(O)R$^A$. In some embodiments, R$^2$ is —R$^C$C(O) NR$^A$R$^B$. In some embodiments, R$^2$ is —NR$^A$R$^B$. In some embodiments, R$^2$ is —NR$^C$CO$_2$R$^A$. In some embodiments, R$^2$ is —NR$^C$S(O)$_2$R$^A$. In some embodiments, R$^2$ is —SR$^A$. In some embodiments, R$^2$ is —S(O)R$^A$. In some embodiments, R$^2$ is —S(O)$_2$R$^A$. In some embodiments, R$^2$ is —S(O)$_2$NR$^A$R$^B$. In some embodiments, R$^2$ is substituted or unsubstituted C$_{6-10}$ aryl. In some embodiments, R$^2$ is substituted C$_{6-10}$ aryl. In some embodiments, R$^2$ is unsubstituted C$_{6-10}$ aryl. In some embodiments, R$^2$ is substituted or unsubstituted 5- to 10-membered heteroaryl. In some embodiments, R$^2$ is substituted 5- to 10-membered heteroaryl. In some embodiments, R$^2$ is unsubstituted 5- to 10-membered heteroaryl. In some embodiments, R$^2$ is substituted or unsubstituted 3- to 10-membered heterocyclyl. In some embodiments, R$^2$ is substituted 3- to 10-membered heterocyclyl. In some embodiments, R$^2$ is unsubstituted 3- to 10-membered heterocyclyl.

In some embodiments of compounds represented by formulas II and III, R$^2$ is selected from: —H, halogen, substituted or unsubstituted C$_{1-8}$ alkyl, substituted or unsubstituted C$_{3-6}$ cycloalkyl, —C(O)NR$^A$R$^B$, —OR$^A$, —NR$^A$R$^B$, —S(O)$_2$R$^A$, substituted or unsubstituted 5- to 10-membered heteroaryl, and substituted or unsubstituted 3- to 10-membered heterocyclyl.

In some embodiments of compounds represented by formulas II and III, R$^2$ is selected from: —H, chloro, trifluoromethyl, cyclopropyl, —C=O)NHCH$_3$, —OCH$_3$, —O-cyclopropyl, —NH-cyclopropyl, 1-methyl-piperazin-1-yl, 4-methylpiperazin-1-yl)ethoxyl, phenyl, oxetan-3-yl, cyclobutyl, tert-butyl, —S(O)$_2$-cyclopropyl, piperazinyl-1-yl, pyrrolidiny-3-yl-amino, and —OH. In some embodiments, R$^2$ is —H. In some embodiments, R$^2$ is chloro. In some embodiments, R$^2$ is trifluoromethyl. In some embodiments, R$^2$ is cyclopropyl. In some embodiments, R$^2$ is —(C=O)NHCH$_3$. In some embodiments, R$^2$ is —OCH$_3$. In some embodiments, R$^2$ is —O-cyclopropyl. In some embodiments, R$^2$ is —NH-cyclopropyl. In some embodiments, R$^2$ is 1-methyl-piperazin-1-yl. In some embodiments, R$^2$ is 4-methylpiperazin-1-yl)ethoxyl. In some embodiments, R$^2$ is phenyl. In some embodiments, R$^2$ is oxetan-3-yl. In some embodiments, R$^2$ is cyclobutyl. In some embodiments, R$^2$ is and tert-butyl. In some embodiments, R$^2$ is chloro or —OCH$_3$. In some embodiments, R$^2$ is —S(O)$_2$-cyclopropyl. In some embodiments, R$^2$ is piperazin-1-yl. In some embodiments, R$^2$ is pyrrolidin-3-yl-amino. In some embodiments, R$^2$ is —OH.

In some embodiments of compounds represented by formulas II and III, R$^3$ is H. In some embodiments, R$^3$ is halogen. In some embodiments, R$^3$ is substituted or unsubstituted C$_{1-8}$ alkyl. In some embodiments, R$^3$ is unsubstituted C$_{1-8}$ alkyl. In some embodiments, R$^3$ is substituted C$_{1-8}$ alkyl. In some embodiments, R$^3$ is cycloalkyl. In some embodiments, R$^3$ is cyclopropyl. In some embodiments, R$^3$ is substituted or unsubstituted C$_{3-6}$ cycloalkyl. In some embodiments, R$^3$ is substituted C$_{3-6}$ cycloalkyl. In some embodiments, R$^3$ is unsubstituted 03-6 cycloalkyl. In some embodiments, R$^3$ is substituted or unsubstituted C$_{2-8}$ alkenyl. In some embodiments, R$^3$ is unsubstituted C$_{2-8}$ alkenyl. In some embodiments, R$^3$ is substituted C$_{2-8}$ alkenyl. In some embodiments, R$^3$ is substituted or unsubstituted C$_{2-8}$ alkynyl. In some embodiments, R$^3$ is unsubstituted C$_{2-8}$ alkynyl. In some embodiments, R$^3$ is substituted C$_{2-8}$ alkynyl. In some embodiments, R$^3$ is —CN. In some embodiments, $R^3$ is —$NO_2$. In some embodiments, $R^3$ is —$C(O)R^A$. In some embodiments, $R^3$ is —$CO_2R^A$. In some embodiments, $R^3$ is —$C(O)NR^AR^B$. In some embodiments, $R^3$ is —$OR^A$. In some embodiments, $R^3$ is —$OC(O)R^A$. In some embodiments, $R^3$ is —$OC(O)NR^AR^B$. In some embodiments, $R^3$ is —$NR^CC(O)R^A$. In some embodiments, $R^3$ is —$R^CC(O)NR^AR^B$. In some embodiments, $R^3$ is —$NR^AR^B$. In some embodiments, $R^3$ is —$NR^CCO_2R^A$. In some embodiments, $R^3$ is —$NR^CS(O)_2R^A$. In some embodiments, $R^3$ is —$SR^A$. In some embodiments, $R^3$ is —$S(O)R^A$. In some embodiments, $R^3$ is —$S(O)_2R^A$. In some embodiments, $R^3$ is —$S(O)_2NR^AR^B$. In some embodiments, $R^3$ is substituted or unsubstituted $C_{6-10}$ aryl. In some embodiments, $R^3$ is substituted $C_{6-10}$ aryl. In some embodiments, $R^3$ is unsubstituted $C_{6-10}$ aryl. In some embodiments, $R^3$ is substituted or unsubstituted 5- to 10-membered heteroaryl. In some embodiments, $R^3$ is substituted 5- to 10-membered heteroaryl. In some embodiments, $R^3$ is unsubstituted 5- to 10-membered heteroaryl. In some embodiments, $R^3$ is substituted or unsubstituted 3- to 10-membered heterocyclyl. In some embodiments, $R^3$ is substituted 3- to 10-membered heterocyclyl. In some embodiments, $R^3$ is unsubstituted 3- to 10-membered heterocyclyl.

In some embodiments of compounds represented by formulas II and III, $R^3$ is selected from: —H, halogen, substituted or unsubstituted $C_{1-8}$ alkyl, substituted or unsubstituted $C_{3-6}$ cycloalkyl, —$C(O)NR^AR^B$, —$OR^A$, —$NR^AR^B$, —$S(O)_2R^A$, substituted or unsubstituted 5- to 10-membered heteroaryl, and substituted or unsubstituted 3- to 10-membered heterocyclyl.

In some embodiments of compounds represented by formulas II and III, $R^3$ is selected from: —H, chloro, trifluoromethyl, cyclopropyl, —C=O)NHCH_3, —OCH_3, —O-cyclopropyl, —NH-cyclopropyl, 1-methyl-piperazin-1-yl, 4-methyl-piperazin-1-yl)ethoxyl, phenyl, oxetan-3-yl, cyclobutyl, tert-butyl, —$S(O)_2$-cyclopropyl, piperazin-1-yl, pyrrolidin-3-yl, and —OH. In some embodiments, $R^3$ is chloro. In some embodiments, $R^3$ is cyclopropyl. In some embodiments, $R^3$ is —(C=O)NHCH_3. In some embodiments, $R^3$ is —OCH_3. In some embodiments, $R^3$ is —O-cyclopropyl. In some embodiments, $R^3$ is —NH-cyclopropyl. In some embodiments, $R^3$ is 1-methyl-piperazin-1-yl. In some embodiments, $R^3$ is 4-methylpiperazin-1-yl)ethoxyl. In some embodiments, $R^3$ is phenyl. In some embodiments, $R^3$ is oxetan-3-yl. In some embodiments, $R^3$ is cyclobutyl. In some embodiments, $R^3$ is and tert-butyl. In some embodiments, $R^3$ is —$S(O)_2$-cyclopropyl. In some embodiments, $R^3$ is piperazin-1-yl. In some embodiments, $R^3$ is pyrrolidin-3-yl. In some embodiments, $R^3$ is —OH.

In some embodiments of compounds represented by formulas II and III, $R^4$ is H. In some embodiments, $R^4$ is halogen. In some embodiments, $R^4$ is substituted or unsubstituted $C_{1-8}$ alkyl. In some embodiments, $R^4$ is unsubstituted $C_{1-8}$ alkyl. In some embodiments, $R^4$ is substituted $C_{1-8}$ alkyl. In some embodiments, $R^4$ is cycloalkyl. In some embodiments, $R^4$ is cyclopropyl. In some embodiments, $R^4$ is substituted or unsubstituted $C_{3-6}$ cycloalkyl. In some embodiments, $R^4$ is substituted $C_{3-6}$ cycloalkyl. In some embodiments, $R^4$ is unsubstituted $C_{3-6}$ cycloalkyl. In some embodiments, $R^4$ is substituted or unsubstituted $C_{2-8}$ alkenyl. In some embodiments, $R^4$ is unsubstituted $C_{2-8}$ alkenyl. In some embodiments, $R^4$ is substituted $C_{2-8}$ alkenyl. In some embodiments, $R^4$ is substituted or unsubstituted $C_{2-8}$ alkynyl. In some embodiments, $R^4$ is unsubstituted $C_{2-8}$ alkynyl. In some embodiments, $R^4$ is substituted $C_{2-8}$ alkynyl. In some embodiments, $R^4$ is —CN. In some embodiments, $R^4$ is —$NO_2$. In some embodiments, $R^4$ is —$C(O)R^A$.

In some embodiments, $R^4$ is —$CO_2R^A$. In some embodiments, $R^4$ is —$C(O)NR^AR^B$. In some embodiments, $R^4$ is —$OR^A$. In some embodiments, $R^4$ is —$OC(O)R^A$. In some embodiments, $R^4$ is —$OC(O)NR^AR^B$. In some embodiments, $R^4$ is —$NR^CC(O)R^A$. In some embodiments, $R^4$ is —$R^CC(O)NR^AR^B$. In some embodiments, $R^4$ is —$NR^AR^B$. In some embodiments, $R^4$ is —$NR^CCO_2R^A$. In some embodiments, $R^4$ is —$NR^CS(O)_2R^A$. In some embodiments, $R^4$ is —$SR^A$. In some embodiments, $R^4$ is —$S(O)R^A$. In some embodiments, $R^4$ is —$S(O)_2R^A$. In some embodiments, $R^4$ is —$S(O)_2NR^AR^B$. In some embodiments, $R^4$ is substituted or unsubstituted $C_{6-10}$ aryl. In some embodiments, $R^4$ is substituted $C_{6-10}$ aryl. In some embodiments, $R^4$ is unsubstituted $C_{6-10}$ aryl. In some embodiments, $R^4$ is substituted or unsubstituted 5- to 10-membered heteroaryl. In some embodiments, $R^4$ is substituted 5- to 10-membered heteroaryl. In some embodiments, $R^4$ is unsubstituted 5- to 10-membered heteroaryl. In some embodiments, $R^4$ is substituted or unsubstituted 3- to 10-membered heterocyclyl. In some embodiments, $R^4$ is substituted 3- to 10-membered heterocyclyl. In some embodiments, $R^4$ is unsubstituted 3- to 10-membered heterocyclyl.

In some embodiments of compounds represented by formulas II and III, $R^4$ is selected from: —H, halogen, substituted or unsubstituted $C_{1-8}$ alkyl, cycloalkyl, —$C(O)NR^AR^B$, —$OR^A$, —$NR^AR^B$, —$S(O)_2R^A$, substituted or unsubstituted 5- to 10-membered heteroaryl, and substituted or unsubstituted 3- to 10-membered heterocyclyl.

In some embodiments of compounds represented by formulas II and III, $R^4$ is selected from: —H, chloro, trifluoromethyl, cyclopropyl, —C=O)NHCH_3, —OCH_3, —O-cyclopropyl, —NH-cyclopropyl, 1-methyl-piperazin-1-yl, 4-methylpiperazin-1-yl)ethoxyl, phenyl, oxetan-3-yl, cyclobutyl, tert-butyl, —$S(O)_2$-cyclopropyl, piperazin-1-yl, pyrrolidin-3-yl-amino, and —OH. In some embodiments, $R^4$ is —H. In some embodiments, $R^4$ is chloro. In some embodiments, $R^4$ is trifluoromethyl. In some embodiments, $R^4$ is cyclopropyl. In some embodiments, $R^4$ is —(C=O)NHCH_3. In some embodiments, $R^4$ is —OCH_3. In some embodiments, $R^4$ is —O-cyclopropyl. In some embodiments, $R^4$ is —NH-cyclopropyl. In some embodiments, $R^4$ is 1-methyl-piperazin-1-yl. In some embodiments, $R^4$ is 4-methylpiperazin-1-yl)ethoxyl. In some embodiments, $R^4$ is phenyl. In some embodiments, $R^4$ is oxetan-3-yl. In some embodiments, $R^4$ is cyclobutyl. In some embodiments, $R^4$ is and tert-butyl. In some embodiments, $R^4$ is chloro trifluoromethyl, or —OCH_3. In some embodiments, $R^4$ is —$S(O)_2$-cyclopropyl. In some embodiments, $R^4$ is piperazin-1-yl. In some embodiments, $R^4$ is pyrrolidin-3-yl. In some embodiments, $R^4$ is —OH.

In some embodiments of compounds represented by formulas II and III, each of $R^1$, $R^2$, $R^3$, and $R^4$ is —H. In some embodiments represented by formula II, at least one of $R^1$, $R^2$, $R^3$, and $R^4$ is not —H.

In some embodiments of Formula II, at least one of $R^1$, $R^2$, $R^3$, and $R^4$ is halogen, substituted or unsubstituted $C_{1-8}$ alkyl, cycloalkyl, —$C(O)NR^AR^B$, —$OR^A$, —$NR^AR^B$, —$S(O)_2R^A$, substituted or unsubstituted 5- to 10-membered heteroaryl, or substituted or unsubstituted 3- to 10-membered heterocyclyl.

In some embodiments of compounds represented by formulas II and III, $R^1$ is selected from —H, chloro, trifluoromethyl, cyclopropyl, —(C=O)NHCH_3, —OCH_3, —O-cyclopropyl, —NH-cyclopropyl, 1-methyl-piperazin-1-yl, 4-methylpiperazin-1-yl)ethoxyl, phenyl, oxetan-3-yl, cyclobutyl, tert-butyl, —$S(O)_2$-cyclopropyl, piperazin-1-yl, pyrrolidin-3-yl-amino, and —OH; $R^2$ is selected from —H, chloro and —OCH$_3$; R$^3$ is selected from chloro, cyclopropyl, —(C=O)NHCH$_3$, —OCH$_3$, —O-cyclopropyl, —NH-cyclopropyl, 1-methyl-piperazin-1-yl, 4-methylpiperazin-1-yl)ethoxyl, phenyl, oxetan-3-yl, cyclobutyl, tert-butyl, —S(O)$_2$-cyclopropyl, piperazin-1-yl, pyrrolidin-3-yl-amino, and —OH; and R$^4$ is selected from —H, chloro, trifluoromethyl, and —OCH$_3$, wherein at least one of R$^1$, R$^2$, R$^3$, and R$^4$ is not —H.

In some embodiments, at least one of R$^1$ and R$^3$ is selected from —S(O)$_2$-cyclopropyl and 1-methyl-piperazin-1-yl. In some embodiments, one of R$^1$ and R$^3$ is selected from —S(O)$_2$-cyclopropyl and 1-methyl-piperazin-1-yl and the other of R$^1$ and R$^3$ is selected from —H, —Cl, —S(O)$_2$-cyclopropyl, —NH-cyclopropyl, and cyclopropyl. In some embodiments, at least one of R$^1$ and R$^3$ is —S(O)$_2$-cyclopropyl. In some embodiments, R$^1$ is —S(O)$_2$-cyclopropyl and R$^3$ is —H. In some embodiments, at least one of R$^1$ and R$^3$ is 1-methyl-piperazin-1-yl. In some embodiments, at least one of R$^1$ and R$^3$ is piperazin-1-yl. In some embodiments, at least one of R$^1$ and R$^3$ is —O-cyclopropyl and the other of R$^1$ and R$^3$ is —H. In some embodiments, each of R$^1$ and R$^3$ is selected from cyclopropyl, —O-cyclopropyl, —NH-cyclopropyl, —S(O)$_2$-cyclopropyl, 1-methyl-piperazin-1-yl, piperazin-1-yl, and oxetan-3-yl.

In some embodiments of compounds of Formula I-III, R$^5$ is H. In some embodiments of compounds of Formula I-III, R$^6$ is H. In some embodiments of compounds of Formula I-III, R$^5$ and R$^6$ are both H.

In some embodiments of compounds of Formula I-III, R$^7$ is H.

In some embodiments of compounds of Formula I-III, R$^8$ is selected from —H and halogen. In some embodiments, R$^8$ is —H. In some embodiments, R$^8$ is halogen. In some embodiments, R$^8$ is fluoro. In some embodiments, R$^8$ is chloro. In some embodiments, R$^8$ is bromo. In some embodiments, R$^8$ is iodo.

In some embodiments of compounds of Formula I-III, R$^9$ is selected from —H and halogen. In some embodiments, R$^9$ is —H. In some embodiments, R$^9$ is halogen. In some embodiments, R$^9$ is fluoro. In some embodiments, R$^9$ is chloro. In some embodiments, R$^9$ is bromo. In some embodiments, R$^9$ is iodo.

In some embodiments of compounds of Formula I-III, R$^8$ and R$^9$ are both —H.

In some embodiments, R$^8$ is fluoro and R$^9$ is —H.

In some embodiments of compounds of Formula I-III, R$^{10}$ is H.

In some embodiments of compounds of Formula I-III, R$^{11}$ is selected from —H, substituted or unsubstituted C$_{1-8}$ alkyl, cycloalkyl, and —NR$^A$R$^B$. In some embodiments, R$^{11}$ is —H. In some embodiments, R$^{11}$ is substituted or unsubstituted C$_{1-8}$ alkyl. In some embodiments, R$^{11}$ is substituted C$_{1-8}$ alkyl. In some embodiments, R$^{11}$ is substituted C$_{1-8}$ alkyl. In some embodiments, R$^{11}$ is cycloalkyl. In some embodiments, R$^{11}$ is —NR$^A$R$^B$.

In some embodiments of compounds of Formula I-III, R$^{11}$ is selected from —H, —CH$_3$, and —NH$_2$. In some embodiments, R$^{11}$ is —H. In some embodiments, R$^{11}$ is —CH$_3$. In some embodiments, R$^{11}$ is —NH$_2$.

In some embodiments of compounds of Formula I-III, R$^A$ is —H. In some embodiments, R$^A$ is halogen. In some embodiments, R$^A$ is substituted or unsubstituted C$_{1-8}$ alkyl. In some embodiments, R$^A$ is unsubstituted C$_{1-8}$ alkyl. In some embodiments, R$^A$ is substituted C$_{1-8}$ alkyl. In some embodiments, R$^A$ is cycloalkyl. In some embodiments, R$^A$ is cyclopropyl. In some embodiments, R$^A$ is substituted or unsubstituted C$_{3-6}$ cycloalkyl. In some embodiments, R$^A$ is substituted C$_{3-6}$ cycloalkyl. In some embodiments, R$^A$ is unsubstituted C$_{3-6}$ cycloalkyl. In some embodiments, R$^A$ is substituted or unsubstituted C$_{2-8}$ alkenyl. In some embodiments, R$^A$ is unsubstituted C$_{2-8}$ alkenyl. In some embodiments, R$^A$ is substituted C$_{2-8}$ alkenyl. In some embodiments, R$^A$ is substituted or unsubstituted C$_{2-8}$ alkynyl. In some embodiments, R$^A$ is unsubstituted C$_{2-8}$ alkynyl. In some embodiments, R$^A$ is substituted C$_{2-8}$ alkynyl. In some embodiments, R$^A$ is —CN. In some embodiments, R$^A$ is =O. In some embodiments, R$^A$ is —NO$_2$. In some embodiments, R$^A$ is —OR'. In some embodiments, R$^A$ is —OC(O)R'. In some embodiments, R$^A$ is —CO$_2$R'. In some embodiments, R$^A$ is —C(O)R'. In some embodiments, R$^A$ is —C(O)NR'R''. In some embodiments, R$^A$ is —OC(O)NR'R''. In some embodiments, R$^A$ is —NR'''C(O)R'. In some embodiments, R$^A$ is —NR'''C(O)NR'R''. In some embodiments, R$^A$ is —NR'R''. In some embodiments, R$^A$ is —NR'''CO$_2$R'. In some embodiments, R$^A$ is —SR'. In some embodiments, R$^A$ is -S(O)R'. In some embodiments, R$^A$ is —S(O)$_2$R'. In some embodiments, R$^A$ is —S(O)$_2$-cycloalkyl. In some embodiments, R$^A$ is —S(O)$_2$-cyclopropyl. In some embodiments, R$^A$ is substituted or unsubstituted —S(O)$_2$-cycloalkyl. In some embodiments, R$^A$ is substituted —S(O)$_2$—C$_{3-6}$ cycloalkyl. In some embodiments, R$^A$ is unsubstituted —S(O)$_2$—C$_{3-6}$ cycloalkyl. In some embodiments, R$^A$ is —S(O)$_2$NR'R''. In some embodiments, R$^A$ is —NR'S(O)$_2$R''. In some embodiments, R$^A$ is substituted or unsubstituted C$_{6-10}$ aryl. In some embodiments, R$^A$ is unsubstituted C$_{6-10}$ aryl. In some embodiments, R$^A$ is substituted C$_{6-10}$ aryl. In some embodiments, R$^A$ is substituted or unsubstituted 5- to 10-membered heteroaryl. In some embodiments, R$^A$ is unsubstituted 5- to 10-membered heteroaryl. In some embodiments, R$^A$ is substituted 5- to 10-membered heteroaryl. In some embodiments, R$^A$ is and substituted or unsubstituted 3- to 10-membered heterocyclyl. In some embodiments, R$^A$ is unsubstituted 3- to 10-membered heterocyclyl. In some embodiments, R$^A$ is substituted 3- to 10-membered heterocyclyl.

In some embodiments of compounds of Formula I-III, R$^B$ is —H. In some embodiments, R$^B$ is halogen. In some embodiments, R$^B$ is substituted or unsubstituted C$_{1-8}$ alkyl. In some embodiments, R$^B$ is unsubstituted C$_{1-8}$ alkyl. In some embodiments, R$^B$ is substituted C$_{1-8}$ alkyl. In some embodiments, R$^B$ is cycloalkyl. In some embodiments, R$^B$ is cyclopropyl. In some embodiments, R$^B$ is substituted or unsubstituted C$_{3-6}$ cycloalkyl. In some embodiments, R$^B$ is substituted C$_{3-6}$ cycloalkyl. In some embodiments, R$^B$ is unsubstituted C$_{3-6}$ cycloalkyl. In some embodiments, R$^B$ is substituted or unsubstituted C$_{2-8}$ alkenyl. In some embodiments, R$^B$ is unsubstituted C$_{2-8}$ alkenyl. In some embodiments, R$^B$ is substituted C$_{2-8}$ alkenyl. In some embodiments, R$^B$ is substituted or unsubstituted C$_{2-8}$ alkynyl. In some embodiments, R$^B$ is unsubstituted C$_{2-8}$ alkynyl. In some embodiments, R$^B$ is substituted C$_{2-8}$ alkynyl. In some embodiments, R$^B$ is —CN. In some embodiments, R$^B$ is =O. In some embodiments, R$^B$ is —NO$_2$. In some embodiments, R$^B$ is —OR'. In some embodiments, R$^B$ is —OC(O)R'. In some embodiments, R$^B$ is —CO$_2$R'. In some embodiments, R$^B$ is —C(O)R'. In some embodiments, R$^B$ is —C(O)NR'R''. In some embodiments, R$^B$ is —OC(O)NR'R''. In some embodiments, R$^B$ is —NR'''C(O)R'. In some embodiments, R$^B$ is —NR'''C(O)NR'R''. In some embodiments, R$^B$ is —NR'R''. In some embodiments, R$^B$ is —NR'''CO$_2$R'. In some embodiments, R$^B$ is —SR'. In some embodiments, R$^B$ is -S(O)R'. In some embodiments, R$^B$ is —S(O)$_2$R'. In some embodiments, R$^B$ is —S(O)$_2$-cycloalkyl. In some embodiments, R$^B$ is —S(O)$_2$-cyclopropyl. In some embodiments, $R^B$ is substituted or unsubstituted —S(O)$_2$-cycloalkyl. In some embodiments, $R^B$ is substituted —S(O)$_2$—C$_{3-6}$ cycloalkyl. In some embodiments, $R^B$ is unsubstituted —S(O)$_2$—C$_{3-6}$ cycloalkyl. In some embodiments, $R^B$ is —S(O)$_2$NR'R". In some embodiments, $R^B$ is —NR'S(O)$_2$R". In some embodiments, $R^B$ is substituted or unsubstituted C$_{6-10}$ aryl. In some embodiments, $R^B$ is unsubstituted C$_{6-10}$ aryl. In some embodiments, $R^B$ is substituted C$_{6-10}$ aryl. In some embodiments, $R^B$ is substituted or unsubstituted 5- to 10-membered heteroaryl. In some embodiments, $R^B$ is unsubstituted 5- to 10-membered heteroaryl. In some embodiments, $R^B$ is substituted 5- to 10-membered heteroaryl. In some embodiments, $R^B$ is and substituted or unsubstituted 3- to 10-membered heterocyclyl. In some embodiments, $R^B$ is unsubstituted 3- to 10-membered heterocyclyl. In some embodiments, $R^B$ is substituted 3- to 10-membered heterocyclyl.

In some embodiments of compounds of Formula I-III, $R^C$ is —H. In some embodiments, $R^C$ is halogen. In some embodiments, $R^C$ is substituted or unsubstituted C$_{1-8}$ alkyl. In some embodiments, $R^C$ is unsubstituted C$_{1-8}$ alkyl. In some embodiments, $R^C$ is substituted C$_{1-8}$ alkyl. In some embodiments, $R^C$ is cycloalkyl. In some embodiments, $R^C$ is cyclopropyl. In some embodiments, $R^C$ is substituted or unsubstituted C$_{3-6}$ cycloalkyl. In some embodiments, $R^C$ is substituted C$_{3-6}$ cycloalkyl. In some embodiments, $R^C$ is unsubstituted C$_{3-6}$ cycloalkyl. In some embodiments, $R^C$ is substituted or unsubstituted C$_{2-8}$ alkenyl. In some embodiments, $R^C$ is unsubstituted C$_{2-8}$ alkenyl. In some embodiments, $R^C$ is substituted C$_{2-8}$ alkenyl. In some embodiments, $R^C$ is substituted or unsubstituted C$_{2-8}$ alkynyl. In some embodiments, $R^C$ is unsubstituted C$_{2-8}$ alkynyl. In some embodiments, $R^C$ is substituted C$_{2-8}$ alkynyl. In some embodiments, $R^C$ is —CN. In some embodiments, $R^C$ is =O. In some embodiments, $R^C$ is —NO$_2$. In some embodiments, $R^B$ is —OR'. In some embodiments, $R^C$ is —OC(O)R'. In some embodiments, $R^C$ is —CO$_2$R'. In some embodiments, $R^C$ is —C(O)R'. In some embodiments, $R^C$ is —C(O)NR'R". In some embodiments, $R^C$ is —OC(O)NR'R". In some embodiments, $R^C$ is —NR'''C(O)R'. In some embodiments, $R^C$ is —NR'''C(O)NR'R". In some embodiments, $R^C$ is —NR'R". In some embodiments, $R^C$ is —NR'''CO$_2$R'. In some embodiments, $R^C$ is —SR'. In some embodiments, $R^C$ is-S(O)R'. In some embodiments, $R^C$ is —S(O)$_2$R'. In some embodiments, $R^C$ is —S(O)$_2$-cycloalkyl. In some embodiments, $R^C$ is —S(O)$_2$-cyclopropyl. In some embodiments, $R^C$ is substituted or unsubstituted —S(O)$_2$-cycloalkyl. In some embodiments, $R^C$ is substituted —S(O)$_2$—C$_{3-6}$ cycloalkyl. In some embodiments, $R^C$ is unsubstituted —S(O)$_2$—C$_{3-6}$ cycloalkyl. In some embodiments, $R^C$ is —S(O)$_2$NR'R". In some embodiments, $R^C$ is —NR'S(O)$_2$R". In some embodiments, $R^C$ is substituted or unsubstituted C$_{6-10}$ aryl. In some embodiments, $R^C$ is unsubstituted C$_{6-10}$ aryl. In some embodiments, $R^C$ is substituted C$_{6-10}$ aryl. In some embodiments, $R^C$ is substituted or unsubstituted 5- to 10-membered heteroaryl. In some embodiments, $R^C$ is unsubstituted 5- to 10-membered heteroaryl. In some embodiments, $R^C$ is substituted 5- to 10-membered heteroaryl. In some embodiments, $R^C$ is and substituted or unsubstituted 3- to 10-membered heterocyclyl. In some embodiments, $R^C$ is unsubstituted 3- to 10-membered heterocyclyl. In some embodiments, $R^C$ is substituted 3- to 10-membered heterocyclyl.

In some embodiments of compounds of Formula I-III, R' is —H. In some embodiments, R' is unsubstituted C$_{1-4}$ alkyl. In some embodiments, R' is cycloalkyl. In some embodiments, R" is —H. In some embodiments, R" is unsubstituted C$_{1-4}$ alkyl. In some embodiments, R" is cycloalkyl. In some embodiments, R' and R" together with the atoms which they substitute form a substituted or unsubstituted 5-, 6-, or 7-membered ring. In some embodiments, R''' is —H. In some embodiments, R''' is unsubstituted C$_{1-4}$ alkyl. In some embodiments, R''' is cycloalkyl.

In another embodiment, the compounds are selected from compounds 1-5, 7-12, and 16-46 in Table 1. In some embodiments, the compounds are selected from compounds 1-5, 7-9, 16-23, 26, 27, 30, 31, 34, 35, 38, 40-42, 45, and 46. In some embodiments, the compounds are selected from compounds 10, 11, 24, 25, 28, 29, 32, 33, 36, 37, 39, 43, and 44. In some embodiments, the compound is compound 12. In some embodiments, the compounds are selected from compounds 7, 11, 19, and 20. In another embodiment, the compounds are selected from compounds 6 and 13-15 in Table 1.

Formulations and Routes of Administration

The compounds described herein, or pharmaceutically acceptable addition salts or hydrates thereof, can be delivered to a patient using a wide variety of routes or modes of administration. Suitable routes of administration include, but are not limited to, inhalation, transdermal, oral, rectal, transmucosal, intestinal and parenteral administration, including intramuscular, subcutaneous and intravenous injections.

The compounds described herein, or pharmaceutically acceptable salts and/or hydrates thereof, may be administered singly, in combination with other compounds of the invention, and/or in cocktails combined with other therapeutic agents. Of course, the choice of therapeutic agents that can be co-administered with the compounds of the invention will depend, in part, on the condition being treated.

For example, when administered to a patient undergoing cancer treatment, the compounds may be administered in cocktails containing other anti-cancer agents and/or supplementary potentiating agents. The compounds may also be administered in cocktails containing agents that treat the side-effects of radiation therapy, such as anti-emetics, radiation protectants, etc.

Anti-cancer drugs that can be co-administered with the compounds disclosed herein, but are not limited to Aminoglutethimide; Asparaginase; Bleomycin; Busulfan; Carboplatin; Carmustine (BCNU); Chlorambucil; Cisplatin (cis-DDP); Cyclophosphamide; Cytarabine HCl; Dacarbazine; Dactinomycin; Daunorubicin HCl; Doxorubicin HCl; Estramustine phosphate sodium; Etoposide (VP-16); Floxuridine; Fluorouracil (5-FU); Flutamide; Hydroxyurea (hydroxycarbamide); Ifosfamide; Interferon α-2a, α-2b, Lueprolide acetate (LHRH-releasing factor analogue); Lomustine (CCNU); Mechlorethamine HCl (nitrogen mustard); Melphalan; Mercaptopurine; Mesna; Methotrexate (MTX); Mitomycin; Mitotane (o.p'-DDD); Mitoxantrone HCl; Octreotide; Plicamycin; Procarbazine HCl; Streptozocin; Tamoxifen citrate; Thioguanine; Thiotepa; Vinblastine sulfate; Vincristine sulfate; Amsacrine (m-AMSA); Azacitidine; Hexamethylmelamine (HMM); Interleukin 2; Mitoguazone (methyl-GAG; methyl glyoxal bis-guanylhydrazone; MGBG); Pentostatin; Semustine (methyl-CCNU); Teniposide (VM-26); paclitaxel and other taxanes; and Vindesine sulfate.

Supplementary potentiating agents that can be co-administered with the compounds of the invention include, but are not limited to, tricyclic anti-depressant drugs (such as imipramine, desipramine, amitriptyline, clomipramine, trimipramine, doxepin, nortriptyline, protriptyline, amoxapine and maprotiline); non-tricyclic and anti-depressant drugs (such as sertraline, trazodone and citalopram); $Ca^{2+}$ antagonists (such as verapamil, nifedipine, nitrendipine and caroverine); Amphotericin (such as Tween 80 and perhexiline maleate); triparanol analogues (such as tamoxifen); antiarrhythmic drugs (such as quinidine); antihypertensive drugs (such as reserpine); thiol depleters (such as buthionine and sulfoximine); and calcium leucovorin.

The active compound(s) may be administered per se or in the form of a pharmaceutical composition wherein the active compound(s) is in admixture with one or more pharmaceutically acceptable carriers, excipients or diluents. Pharmaceutical compositions for use with the compounds described above may be formulated in conventional manner using one or more physiologically acceptable carriers comprising excipients and auxiliaries which facilitate processing of the active compounds into preparations which can be used pharmaceutically. Proper formulation is dependent upon the route of administration chosen.

For injection, the agents of the invention may be formulated in aqueous solutions, preferably in physiologically compatible buffers such as Hanks' solution, Ringer's solution, or physiological saline buffer. For transmucosal administration, penetrants appropriate to the barrier to be permeated are used in the formulation. Such penetrants are generally known in the art.

For oral administration, the compounds can be formulated readily by combining the active compound(s) with pharmaceutically acceptable carriers well known in the art. Such carriers enable the compounds of the invention to be formulated as tablets, pills, dragees, capsules, liquids, gels, syrups, slurries, suspensions and the like, for oral ingestion by a patient to be treated. Pharmaceutical preparations for oral use can be obtained solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate.

Dragee (tablet) cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration.

For buccal administration, the compositions may take the form of tablets or lozenges formulated in conventional manner.

For administration by inhalation, the compounds for use according to the present invention are conveniently delivered in the form of an aerosol spray presentation from pressurized packs or a nebulizer, with the use of a suitable propellant (such as dichlorodifluoromethane, trichlorofluoromethane, dichlorotetrafluoroethane, carbon dioxide or other suitable gas). In the case of a pressurized aerosol the dosage unit may be determined by providing a valve to deliver a metered amount. Capsules and cartridges of gelatin for use in an inhaler or insufflator may be formulated containing a powder mix of the compound and a suitable powder base such as lactose or starch.

The compounds may be formulated for parenteral administration by injection (such as by bolus injection or continuous infusion). Formulations for injection may be presented in unit dosage form (in ampoules or in multi-dose containers) with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension (such as sodium carboxymethyl cellulose, sorbitol, or dextran). Optionally, the suspension may also contain suitable stabilizers or agents which increase the solubility of the compounds to allow for the preparation of highly concentrated solutions.

Alternatively, the active ingredient may be in powder form for constitution with a suitable vehicle (such as sterile pyrogen-free water) before use.

The compounds may also be formulated in rectal compositions such as suppositories or retention enemas (such as containing conventional suppository bases like cocoa butter or other glycerides).

In addition to the formulations described previously, the compounds may also be formulated as a depot preparation. Such long acting formulations may be administered by implantation or transcutaneous delivery (such as subcutaneously or intramuscularly), intramuscular injection or a transdermal patch. Thus, the compounds may be formulated with suitable polymeric or hydrophobic materials (such as an emulsion in an acceptable oil) or ion exchange resins, or as sparingly soluble derivatives (such as a sparingly soluble salt).

The pharmaceutical compositions also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

Effective Dosages

Pharmaceutical compositions suitable for use with the compounds described above include compositions wherein the active ingredient is contained in a therapeutically effective amount (an amount effective to achieve its intended purpose). Of course, the actual amount effective for a particular application will depend on the condition being treated. For example, when administered in methods to inhibit cell proliferation, such compositions will contain an amount of active ingredient effective to achieve this result. When administered to patients suffering from disorders characterized by abnormal cell proliferation, such compositions will contain an amount of active ingredient effective to prevent the development of or alleviate the existing symptoms of, or prolong the survival of, the patient being treated. For use in the treatment of cancer, a therapeutically effective amount further includes that amount of compound which arrests or regresses the growth of a tumor. Determination of an effective amount is well within the capabilities of those skilled in the art.

For any compound described herein the therapeutically effective amount can be initially determined from cell culture arrays. Target plasma concentrations will be those concentrations of active compound(s) that are capable of inducing at least about 25% inhibition of cell proliferation in cell culture assays, depending, of course, on the particular desired application. Target plasma concentrations of active compound(s) that are capable of inducing at least about 50%, 75%, or even 90% or higher inhibition of cell proliferation in cell culture assays are preferred. The percentage of inhibition of cell proliferation in the patient can be monitored to assess the appropriateness of the plasma drug concentration achieved, and the dosage can be adjusted upwards or downwards to achieve the desired percentage of inhibition.

Therapeutically effective amounts for use in humans can also be determined from animal models. For example, a dose for humans can be formulated to achieve a circulating concentration that has been found to be effective in animals. Useful animal models for diseases characterized by abnormal cell proliferation are well-known in the art. In particular, the following references provide suitable animal models for cancer xenografts (Corbett et al., 1996, J. Exp. Ther. Oncol. 1:95-108; Dykes et al., 1992, Contrib. Oncol. Basel. Karger 42:1-22), restenosis (Carter et al., 1994, J. Am. Coll. Cardiol: 24(5):1398-1405), atherosclerosis (Zhu et al., 1994, Cardiology 85(6):370-377) and neovascularization (Epstein et al., 1987, Cornea 6(4):250-257). The dosage in humans can be adjusted by monitoring inhibition of cell proliferation and adjusting the dosage upwards or downwards, as described above.

A therapeutically effective dose can also be determined from human data for compounds which are known to exhibit similar pharmacological activities. Adjusting the dose to achieve maximal efficacy in humans based on the methods described above and other methods as are well-known in the art is well within the capabilities of the ordinarily skilled artisan.

In the case of local administration, the systemic circulating concentration of administered compound will not be of particular importance. In such instances, the compound is administered so as to achieve a concentration at the local area effective to achieve the intended result.

When treating disorders characterized by abnormal cell proliferation, including cancer, a circulating concentration of administered compound of about 0.001 µM to about 20 µM is considered to be effective, or about 0.1 µM to about 5 µM.

Patient doses for oral administration of the compounds described herein for the treatment or prevention of cell proliferative disorders typically range from about 80 mg/day to 16,000 mg/day, more typically from about 800 mg/day to 8000 mg/day, and most typically from about 800 mg/day to 4000 mg/day. Stated in terms of patient body weight, typical dosages range from about 1 to 200 mg/kg/day, more typically from about 10 to 100 mg/kg/day, and most typically from about 10 to 50 mg/kg/day. Stated in terms of patient body surface areas, typical dosages range from about 40 to 8000 mg/m²/day, more typically from about 400 to 4000 mg/m²/day, and most typically from about 400 to 2000 mg/m²/day.

For other modes of administration, dosage amount and interval can be adjusted individually to provide plasma levels of the administered compound effective for the particular clinical indication being treated. For use in the treatment of tumorigenic cancers, the compounds can be administered before, during or after surgical removal of the tumor. For example, the compounds can be administered to the tumor via injection into the tumor mass prior to surgery in a single or several doses. The tumor, or as much as possible of the tumor, may then be removed surgically. Further dosages of the drug at the tumor site can be applied post removal. Alternatively, surgical removal of as much as possible of the tumor can precede administration of the compounds at the tumor site.

Combined with the teachings provided herein, by choosing among the various active compounds and weighing factors such as potency, relative bioavailability, patient body weight, severity of adverse side-effects and preferred mode of administration, an effective prophylactic or therapeutic treatment regimen can be planned which does not cause substantial toxicity and yet is entirely effective to treat the clinical symptoms demonstrated by the particular patient. Of course, many factors are important in determining a therapeutic regimen suitable for a particular indication or patient. Severe indications such as invasive or metastasized cancer may warrant administration of higher dosages as compared with less severe indications such early-detected, non-metastasized cancer.

EXAMPLES

Compounds of Formulas I-III are listed and identified with ¹H-NMR data in Table I. ND indicates that ¹H-NMR data was not identified. The compounds listed in Table I are further characterized in Table II. Methods for preparing each of the compounds in Table I are also identified in Table II. NA in the monomer synthesis column of Table II indicates that the monomer used as the starting material was commercially available except for compounds 51, 52, 53, 54, 55, 56, 58, 60, 65 and 68. Methods for the preparation of compounds 51, 52, 53, 54, 55, 56, 58, 60, 65 and 68 are described elsewhere in the Examples.

General Coupling Procedure 1

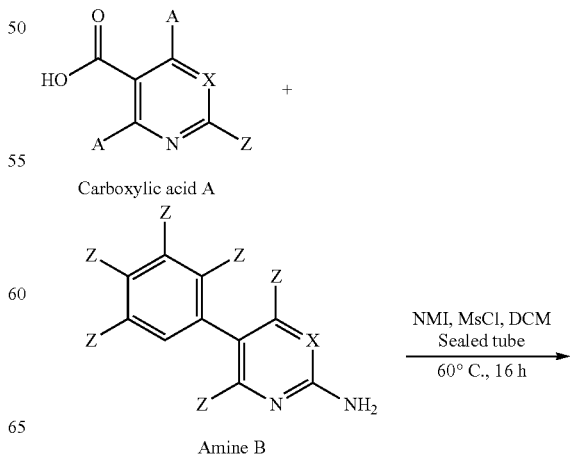

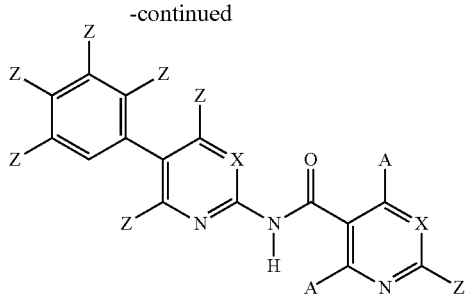

Methanesulfonyl chloride (1.5 eq.) was added to a stirred solution of N-methylimidazole (1.0 eq.) in dichloromethane (25 mL), cooled to 0° C. and the reaction mixture was stirred for 10 to 15 min. Carboxylic acid A (1.0 eq.) was added at 0° C. and again the reaction mixture was stirred for 20 min at 10° C. to 15° C. Amine B (1.2 eq.) was added to the reaction mixture, which was subsequently heated in a sealed glass tube at 55° C. to 60° C. for 16 h. After completion of the reaction, volatiles were removed under reduced pressure. The residual material was triturated with dichloromethane (50 mL), filtered and the wet cake was washed with dichloromethane (100 mL) then dried under reduced pressure to obtain pure product. Additional purification by flash chromatography over silica was performed when necessary.

General Coupling Procedure 2

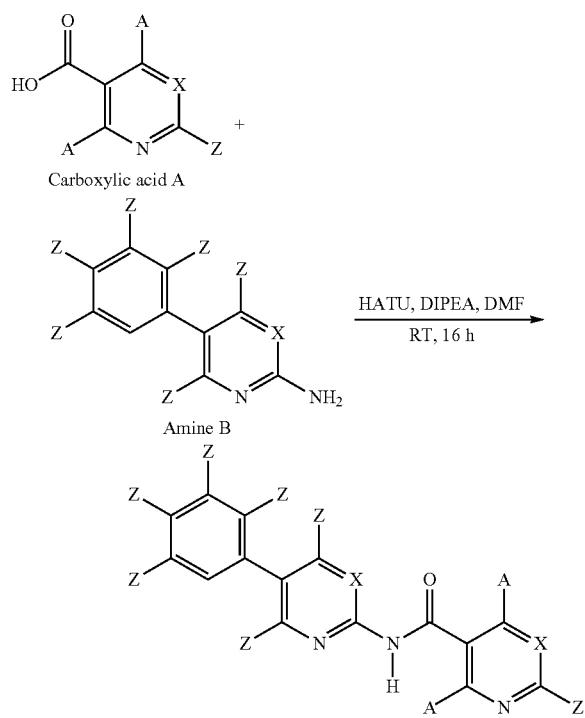

HATU (1.5 eq.) was added to a stirred solution of Carboxylic acid A (1.0 eq.) and Amine B (1.2 eq.) in DMF (25 mL) at 0° C. and, after 30 min. of additional stirring, DIPEA (4.0 eq.) was added in dropwise fashion and the total reaction mixture was stirred at RT for 16 h. After completion of the reaction, ice water was added to the reaction mixture and the precipitated solid was filtered and washed with ethyl acetate (100 ml) and diethyl ether (100 ml) before drying under reduced pressure to obtain pure product. Additional purification by flash chromatography over silica was performed when necessary.

General Coupling Procedure 3

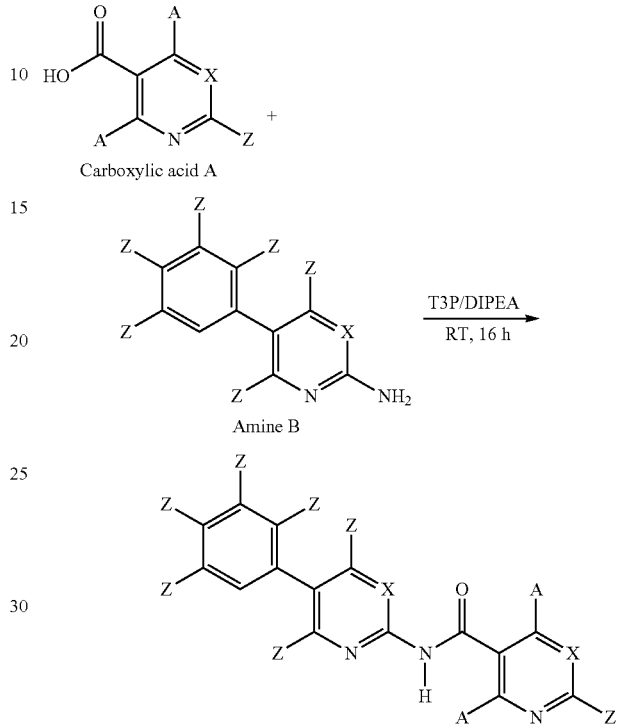

1-Propanephosphonic acid cyclic anhydride (1.5 eq.) and DIPEA (4 eq.) were added to a stirred solution of Carboxylic acid A (1.0 eq.) and Amine B (1.2 eq.) in DMF (25 mL) at RT. The reaction mixture was stirred for 16 h at RT. The reaction mixture was then poured into ice water, stirred for 5 min. and the resulting precipitate was filtered and washed with water. The wet cake was dried under reduced pressure and washed with diethyl ether and n-pentane to obtain a crude product. Additional purification by flash chromatography over silica was performed when necessary.

General Coupling Procedure 4

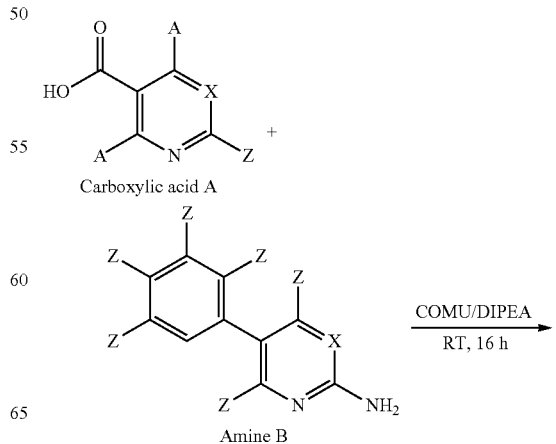

-continued

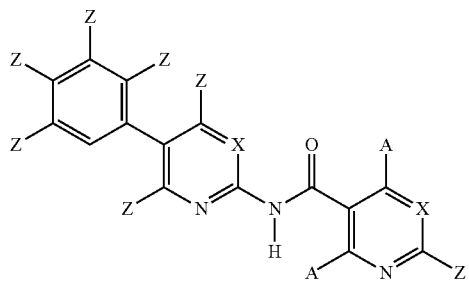

COMU (1.5 eq.) and DIPEA (4 eq.) were added to a stirred solution of Carboxylic acid A (1.0 eq.) and Amine B (1.2 eq.) in THF (2 mL) at RT. The reaction mixture was stirred for 16 h at RT. The reaction mixture was then poured in ice water, stirred for 5 min. and the resulting precipitate was filtered and washed with water. The cake was dried under reduced pressure and washed with diethyl ether and n-pentane to obtain a crude product. Additional purification by flash chromatography over silica was performed when necessary.

General Coupling Procedure 5

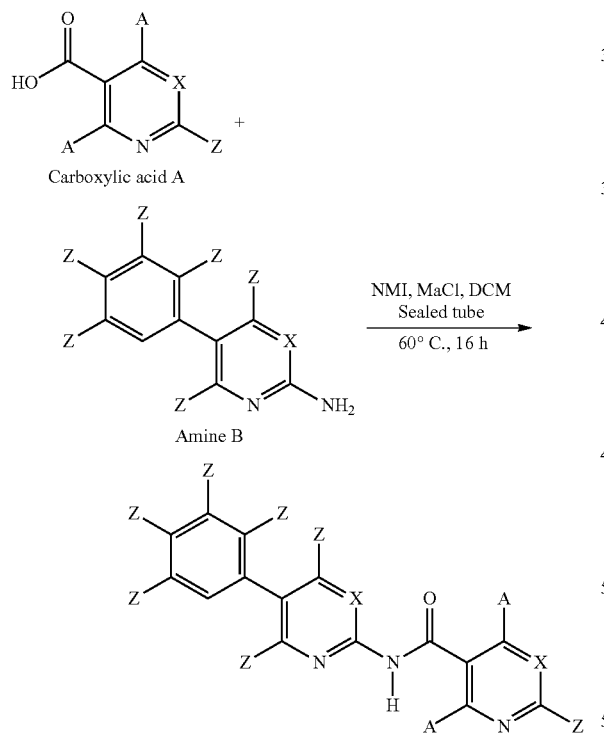

POCl$_3$ (3 eq.) was added to a stirred solution of carboxylic acid A (1.0 eq.) and amine B (1.0 eq.) in pyridine (25 mL) at 0° C. The reaction mixture was stirred for 1 h at RT. The reaction mixture was then filtered and the filtrate was diluted with ethyl acetate (100 mL) then washed with water and brine (100 mL each). The organic layer was dried over Na$_2$SO$_4$ and concentrated under reduced pressure to obtain the crude product, which was then purified by preparative HPLC.

Monomer Synthesis Procedure A

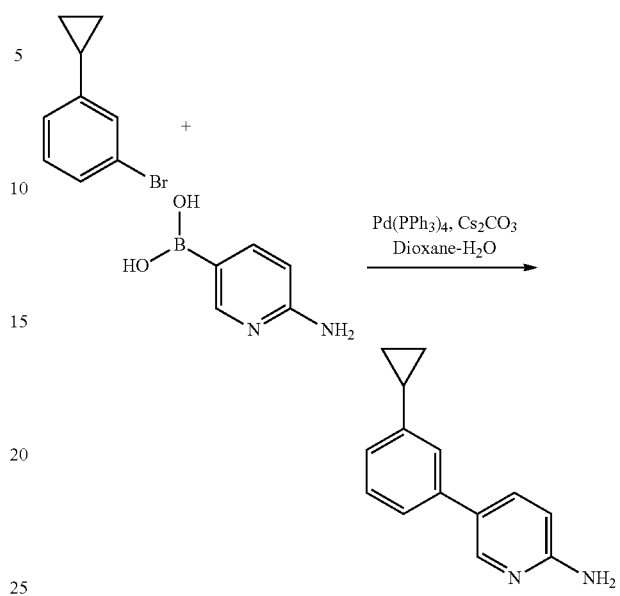

1-Bromo-3-cyclopropylbenzene (0.20 g, 1.4 mmol, 1.0 eq.), 6-Aminopyridine-3-boronic acid (0.28 g, 1.4 mmol, 1.0 eq.) and CS$_2$CO$_3$ (1.41 g, 4.3 mmol, 1.5 eq.) were added to a mixture of dioxane (8 mL) and water (2 mL) which was subsequently degassed with argon for 30 min. Pd(PPh$_3$)$_4$ (0.087 g, 4.3 mmol, 0.05 eq.) was added and the reaction mixture was heated to 90° C. for 16 h. After completion of the reaction, the reaction mixture was filtered and the filtrate was concentrated under reduced pressure. The resulting crude material was dissolved in ethyl acetate (100 mL) and washed with cold water (100 mL) and brine (25 mL). The organic layer was dried over Na$_2$SO$_4$ and concentrated under reduced pressure to obtain crude product. This material was purified by flash chromatography (over silica gel 100-200 mesh) eluting with 25% ethyl acetate in petroleum ether to obtain pure 5-(3-cyclopropylphenyl)pyridin-2-amine (80 mg; 37%).

Monomer Synthesis Procedure B

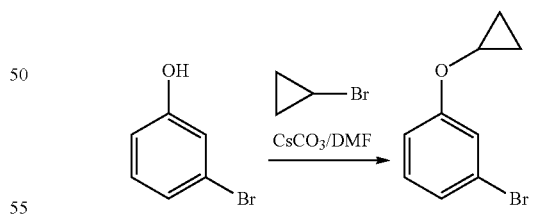

Step-1: CS$_2$CO$_3$ (56.6 g, 174.4 mmol, 3.0 eq.) and NaI (872 mg, 5.81 mmol, 0.1 eq.) were added to a stirred solution of 3-bromophenol (10 g, 58.13 mmol, 1.0 eq.) and bromocyclopropane (13.95 g, 116.2 mmol, 2.0 eq.) in DMF (50 mL). The reaction mixture was heated to 150° C. for 16 h after which time it was allowed to cool to RT. The reaction mixture was then diluted with ethyl acetate (200 mL) then washed with chilled water (100 mL) and brine (50 mL). The organic layer was dried over Na$_2$SO$_4$ and concentrated under reduced pressure to obtain crude product. This material was purified by flash chromatography (over silica gel 100-200 mesh) eluting with 2% ethyl acetate in petroleum ether to obtain pure 1-bromo-3-(cyclopropyloxy)benzene (4.0 g; 32.5%).

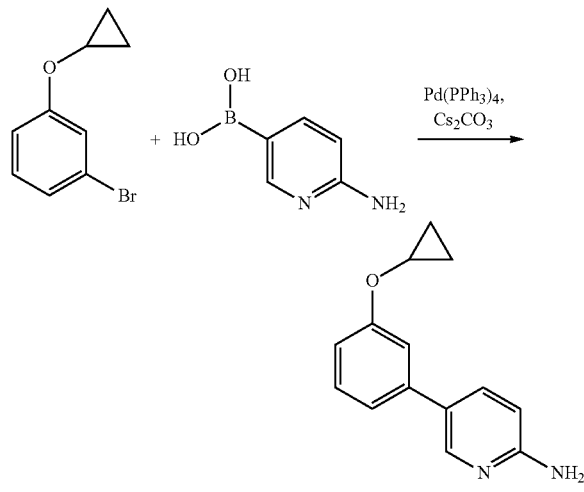

Step-2: A stirred solution of 1-bromo-3-(cyclopropyloxy) benzene (1 g, 4.71 mmol, 1.0 eq.), 6-aminopyridin-3-ylboronic acid (0.65 g, 4.712 mmol, 1.0 eq.), and $Cs_2CO_3$ (4.6 g, 14.13 mmol, 3.0 eq.) in a mixture of dioxane (30 mL) and water (10 mL) was degassed with argon for 30 min. $Pd(PPh_3)_4$ (0.272 g, 0.235 mmol, 0.05 eq.) was added and the reaction mixture was heated to 90° C. for 16 h after which time it was allowed to cool to RT. The reaction mixture was then then filtered and the filtrate was concentrated under reduced pressure. The resulting crude material was diluted with ethyl acetate (200 mL) then washed with chilled water (100 mL) and brine (50 mL). The organic layer was dried over $Na_2SO_4$ and concentrated under reduced pressure to obtain crude product. This material was purified by flash chromatography (over silica gel 100-200 mesh) eluting with 25% Ethyl acetate in petroleum ether to obtain pure 5-[3-(cyclopropyloxy)phenyl]pyridin-2-amine (1.0 g; 56.6%).

Monomer Synthesis Procedure C

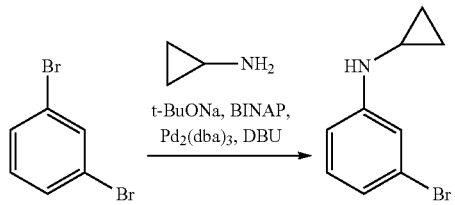

Step-1: BINAP (0.079 g, 0.11 mmol, 0.01 eq.), $Pd_2(dba)_3$ (100 mg, 0.11 mmol, 0.01 eq.), DBU (1.73 g, 10.28 mmol, 0.8 eq.) and Sodium t-butoxide (1.8 g, 19.06 mmol, 1.5 eq.) were added to a stirred solution of 1,3-dibromobenzene (3 g, 12.8 mmol, 1.0 eq.) and cyclopropylamine (0.511 g, 8.9 mmol, 0.7 eq.) in toluene (50 mL) under a nitrogen atmosphere. The reaction mixture was heated to 100° C. for 10 h after which time it was allowed to cool to RT. The reaction mixture was then then filtered and the filtrate was concentrated under reduced pressure. The resulting crude material was diluted with ethyl acetate (200 mL) then washed with chilled water (100 mL) and brine (50 mL). The organic layer was dried over $Na_2SO_4$ and concentrated under reduced pressure to obtain crude product. This material was purified by flash chromatography (using silica gel 100-200 mesh) eluting with 25% Ethyl acetate in petroleum ether to obtain pure 3-bromo-N-cyclopropylaniline (0.5 g; 18.5%).

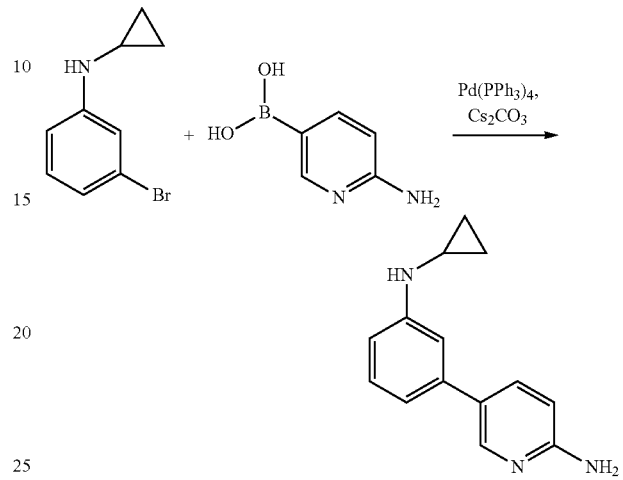

Step-2: A stirred solution of 3-bromo-N-cyclopropylaniline (1 g, 4.73 mmol, 1.0 eq.), 6-aminopyridin-3-ylboronic acid (0.65 g, 4.73 mmol, 1.0 eq.), and $CS_2CO_3$ (4.6 g, 14.13 mmol, 3.0 eq.) in a mixture of dioxane and water (3:1, 40 mL) was degassed with argon for 30 min. $Pd(PPh_3)_4$ (0.272 g, 0.235 mmol, 0.05 eq.) was added and the reaction mixture was heated to 90° C. for 16 h after which time it was allowed to cool to RT. The reaction mixture was then then filtered and the filtrate was concentrated under reduced pressure. The resulting crude material was diluted with ethyl acetate (200 mL) then washed with chilled water (100 mL) and brine (50 mL). The organic layer was dried over $Na_2SO_4$ and concentrated under reduced pressure to obtain crude product. This material was purified by flash chromatography (using silica gel 100-200 mesh) eluting with 25% Ethyl acetate in petroleum ether to obtain pure 5-[3-(cyclopropylamino)phenyl]pyridin-2-amine (0.6 g; 57%).

Monomer Synthesis Procedure D

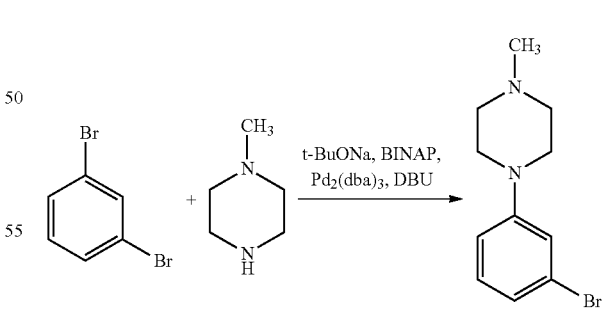

Step-1: BINAP (0.266 g, 0.42 mmol, 0.01 eq.), $Pd_2(dba)_3$ (0.391 g, 0.42 mmol, 0.01 eq.), DBU (5.19 g, 34.18 mmol, 0.8 eq.) and Sodium t-butoxide (6.15 g, 64.1 mmol, 1.5 eq.) were added to a stirred solution of 1,3-dibromobenzene (10 g, 42.7 mmol, 1.0 eq.), and N-methylpiperazine (2.99 g, 29.9 mmol, 0.7 eq.) in toluene (200 mL) under a nitrogen atmosphere. The reaction mixture was heated to 100° C. for 10 h after which time it was allowed to cool to RT. The reaction mixture was then filtered and the filtrate was concentrated under reduced pressure. The resulting crude material was diluted with ethyl acetate (200 mL) then washed with chilled water (100 mL) and brine (50 mL). The organic layer was dried over Na₂SO₄ and concentrated under reduced pressure to obtain crude product. This material was purified by flash chromatography (over silica gel 100-200 mesh) eluting with 25% Ethyl acetate in petroleum ether to obtain pure 1-(3-bromophenyl)-4-methylpiperazine (4.0 g; 37%).

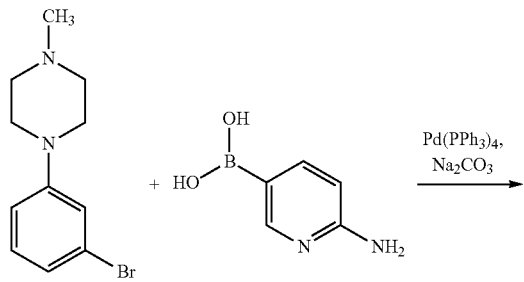

Step-2: A stirred solution of 1-(3-bromophenyl)-4-methylpiperazine (1.7 g, 6.69 mmol, 1.0 eq.), 6-aminopyridin-3-ylboronic acid (0.923 g, 6.69 mmol, 1.0 eq.) and Na₂CO₃ (1.4 g, 13.38 mmol, 2.0 eq.) in a mixture of toluene, EtOH and water (2:2:1, 25 mL) was degassed with argon for 30 min. Pd(PPh₃)₄ (0.386 g, 0.334 mmol, 0.05 eq.) was added and the reaction mixture was heated to 90° C. for 16 h after which time it was allowed to cool to RT. The reaction mixture was then filtered and the filtrate was concentrated under reduced pressure. The resulting crude material was diluted with ethyl acetate (200 mL) then washed with chilled water (100 mL) and brine (50 mL). The organic layer was dried over Na₂SO₄ and concentrated under reduced pressure to obtain crude product. This material was purified by flash chromatography (over silica gel 100-200 mesh) eluting with 25% Ethyl acetate in petroleum ether to obtain pure 5-[3-(4-methylpiperazin-1-yl)phenyl]pyridin-2-amine (1.0 g; 55.8%).

Monomer Synthesis Procedure E

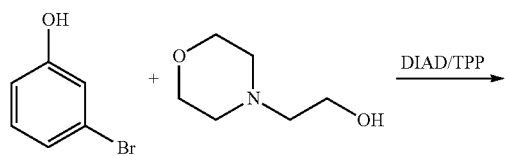

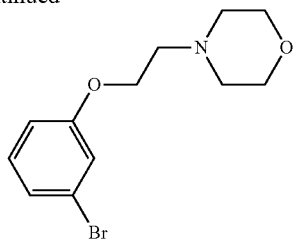

Step-1: 3-Bromophenol (5.0 g, 29.06 mmol) and 2-(morpholin-4-yl)ethanol (4.18 g, 29.06 mmol) were added to a stirred solution of TPP (8.3 g, 31.97 mmol, 1.0 eq.) in THF (100 mL) at RT. The reaction mixture was cooled to 0° C. and DIAD (6.45 g, 31.97 mmol) was added. The reaction mixture was stirred at RT for 16 h then quenched with ice water and extracted with ethyl acetate (3×25 mL). The combined organic layers were dried over Na₂SO₄ and concentrated under reduced pressure to give crude product. This material was purified by flash chromatography (over silica gel 100-200 mesh) eluting with 75% Ethyl acetate in petroleum ether to obtain pure 4-[2-(3-bromophenoxy)ethyl]morpholine (3.0 g; 34.4%).

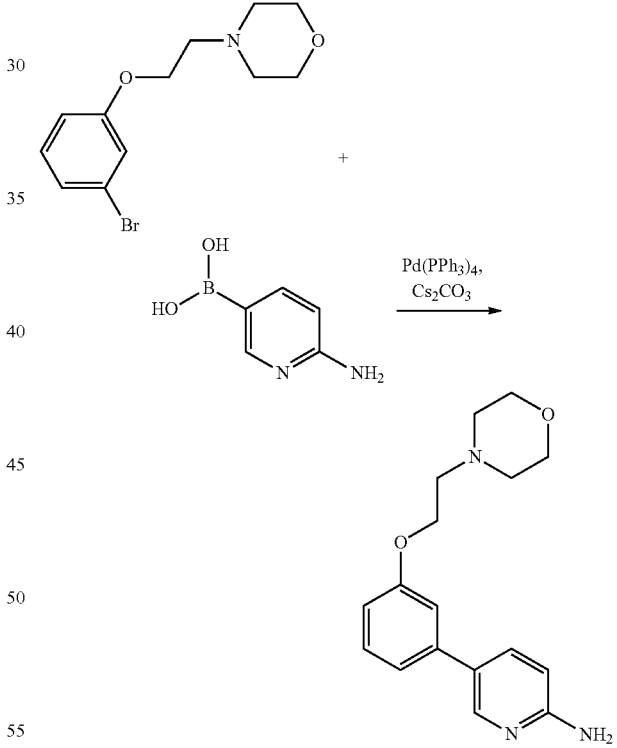

Step-2: A stirred solution of 1-[2-(3-bromophenoxy)ethyl]morpholine (1 g, 3.35 mmol, 1.0 eq.), 6-aminopyridin-3-ylboronic acid (0.463 g, 3.35 mmol, 1.0 eq.), and CS₂CO₃ (3.26 g, 1.05 mmol, 3.0 eq.) in a mixture of dioxane (30 mL) and water (10 mL) was degassed with argon for 30 min. Pd(PPh₃)₄ (0.193 g, 0.167 mmol, 0.05 eq.) was added and the reaction mixture was heated to 90° C. for 16 h after which time it was allowed to cool to RT. The reaction mixture was then filtered and the filtrate was concentrated under reduced pressure. The resulting crude material was diluted with ethyl acetate (200 mL) then washed with chilled water (100 mL) and brine (50 mL). The organic layer was dried over Na$_2$SO$_4$ and concentrated under reduced pressure to obtain crude product. This material was purified by flash chromatography (over silica gel 100-200 mesh) eluting with 25% ethyl acetate in petroleum ether to obtain pure 5-[3-(4-methylpiperazin-1-yl)phenyl]pyridin-2-amine (300 mg; 28.8%).

Monomer Synthesis Procedure F

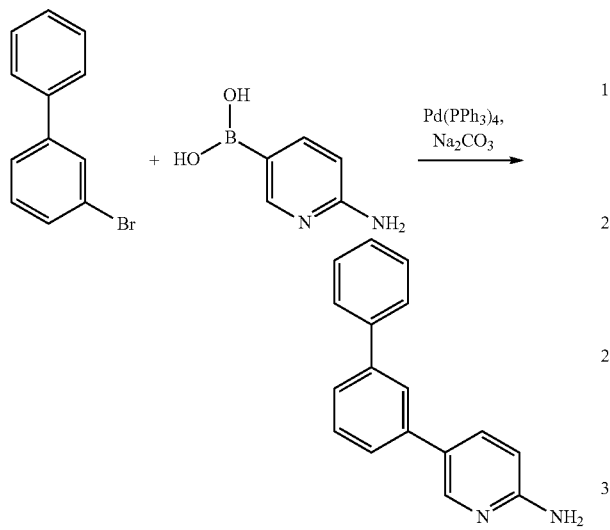

A solution of 3-bromobiphenyl (500 mg, 2.155 mmol, 1.0 eq.), 6-aminopyridin-3-ylboronic acid (0.297 g, 2.15 mmol, 1.0 eq.), and Na$_2$CO$_3$ (452 mg, 4.31 mmol, 2.0 eq.) in a mixture of toluene, EtOH and water (2:2:1, 5 mL) was degassed with argon for 30 min. Pd(PPh$_3$)$_4$ (0.124 g, 0.107 mmol, 0.05 eq.) was added and the reaction mixture was heated to 90° C. for 16 h after which time it was allowed to cool to RT. The reaction mixture was then filtered and the filtrate was concentrated under reduced pressure. The resulting crude material was diluted with ethyl acetate (200 mL) then washed with chilled water (100 mL) and brine (50 mL). The organic layer was dried over Na$_2$SO$_4$ and concentrated under reduced pressure to obtain crude product. This material was purified by flash chromatography (over silica gel 100-200 mesh) eluting with 25% Ethyl acetate in petroleum ether to obtain pure 5-(biphenyl-3-yl)pyridin-2-amine (200 mg; 37.7%).

Monomer Synthesis Procedure G

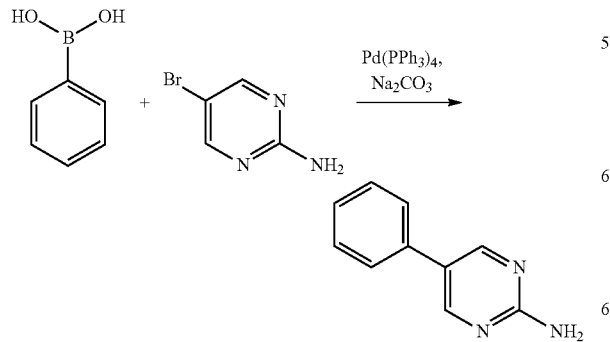

A solution of phenylboronic acid (500 mg, 4.09 mmol, 1.0 eq.), 5-bromopyrimidin-2-amine (0.709 g, 4.09 mmol, 1.0 eq.), and Na$_2$CO$_3$ (860 mg, 8.19 mmol, 2.0 eq.) in a mixture of toluene, EtOH and water (2:2:1, 5 mL) was degassed with argon for 30 min. Pd(PPh$_3$)$_4$ (0.236 g, 0.204 mmol, 0.05 eq.) was added and the reaction mixture was heated to 90° C. for 16 h after which time it was allowed to cool to RT. The reaction mixture was then filtered and the filtrate was concentrated under reduced pressure. The resulting crude material was diluted with ethyl acetate (200 mL) then washed with chilled water (100 mL) and brine (50 mL). The organic layer was dried over Na$_2$SO$_4$ and concentrated under reduced pressure to obtain crude product. This material was purified by flash chromatography (over silica gel 100-200 mesh) eluting with 25% Ethyl acetate in petroleum ether to obtain pure 5-phenylpyrimidin-2-amine (200 mg; 28.5%).

Monomer Synthesis Procedure H

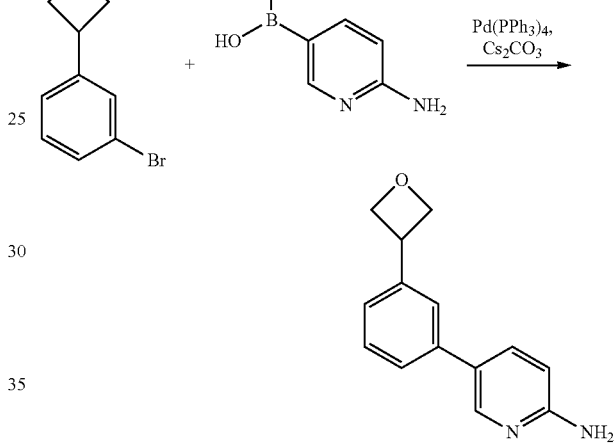

A solution of 3-(3-bromophenyl)oxetane (1 g, 4.71 mmol, 1.0 eq.), 6-aminopyridin-3-ylboronic acid (0.658 g, 4.71 mmol, 1.0 eq.), and CS$_2$CO$_3$ (4.6 g, 14.13 mmol, 3.0 eq.) in a mixture of dioxane (10 mL) and water (3 mL) was degassed with argon for 30 min. Pd(PPh$_3$)$_4$ (0.272 g, 0.235 mmol, 0.05 eq.) was added and the reaction mixture was heated to 90° C. for 16 h after which time it was allowed to cool to RT. The reaction mixture was then filtered and the filtrate was concentrated under reduced pressure. The resulting crude material was diluted with ethyl acetate (200 mL) then washed with chilled water (100 mL) and brine (50 mL). The organic layer was dried over Na$_2$SO$_4$ and concentrated under reduced pressure to obtain crude product. This material was purified by flash chromatography (over silica gel 100-200 mesh) eluting with 25% Ethyl acetate in petroleum ether to obtain pure 5-[3-(oxetan-3-yl)phenyl]pyridin-2-amine (600 mg; 56.2%).

Monomer Synthesis Procedure I

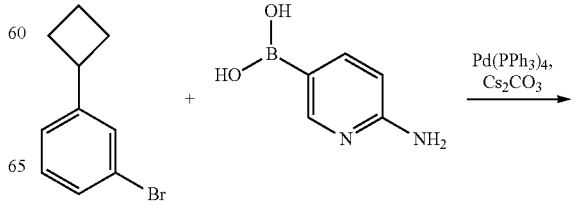

-continued

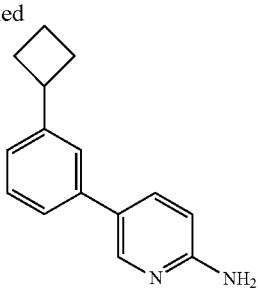

A solution of 1-bromo-3-cyclobutylbenzene (500 mg, 2.38 mmol, 1.0 eq.), 6-aminopyridin-3-ylboronic acid (0.328 g, 2.38 mmol, 1.0 eq.), and $Cs_2CO_3$ (2.32 g, 7.14 mmol, 3.0 eq.) in a mixture of dioxane (5 mL) and water (3 mL) was degassed with argon for 30 min. $Pd(PPh_3)_4$ (0.137 g, 0.119 mmol, 0.05 eq.) was added and the reaction mixture was heated to 90° C. for 16 h after which time it was allowed to cool to RT. The reaction mixture was then filtered and the filtrate was concentrated under reduced pressure. The resulting crude material was diluted with ethyl acetate (200 mL) then washed with chilled water (100 mL) and brine (50 mL). The organic layer was dried over $Na_2SO_4$ and concentrated under reduced pressure to obtain crude product. This material was purified by flash chromatography (over silica gel 100-200 mesh) eluting with 25% Ethyl acetate in petroleum ether to obtain pure 5-(3-cyclobutylphenyl)pyridin-2-amine (300 mg; 56.2%).

Monomer Synthesis Procedure J

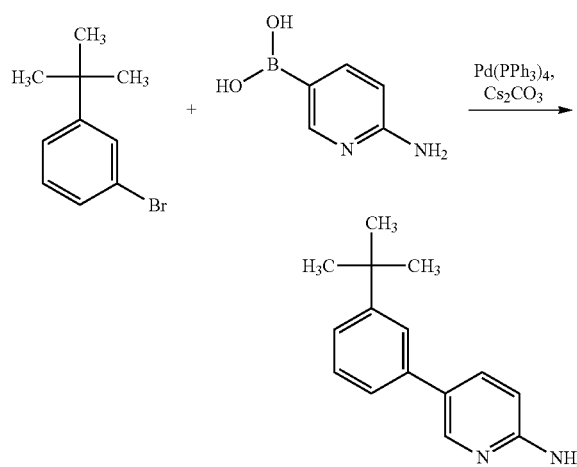

A stirred solution of 1-bromo-3-tert-butylbenzene (500 mg, 2.35 mmol, 1.0 eq.), 6-aminopyridin-3-ylboronic acid (0.325 g, 2.35 mmol, 1.0 eq.), and $CS_2CO_3$ (2.29 g, 7.05 mmol, 3.0 eq.) in a mixture of dioxane (5 mL) and water (3 mL) was degassed with argon for 30 min. $Pd(PPh_3)_4$ (0.136 g, 0.117 mmol, 0.05 eq.) was added and the reaction mixture was heated to 90° C. for 16 h after which time it was allowed to cool to RT. The reaction mixture was then filtered and the filtrate was concentrated under reduced pressure. The resulting crude material was diluted with ethyl acetate (200 mL) then washed with chilled water (100 mL) and brine (50 mL). The organic layer was dried over $Na_2SO_4$ and concentrated under reduced pressure to obtain crude product. This material was purified by flash chromatography (over silica gel 100-200 mesh) eluting with 25% Ethyl acetate in petroleum ether to obtain 5-(3-tert-butylphenyl)pyridin-2-amine (250 mg; 46.9%).

Monomer Synthesis Procedure K

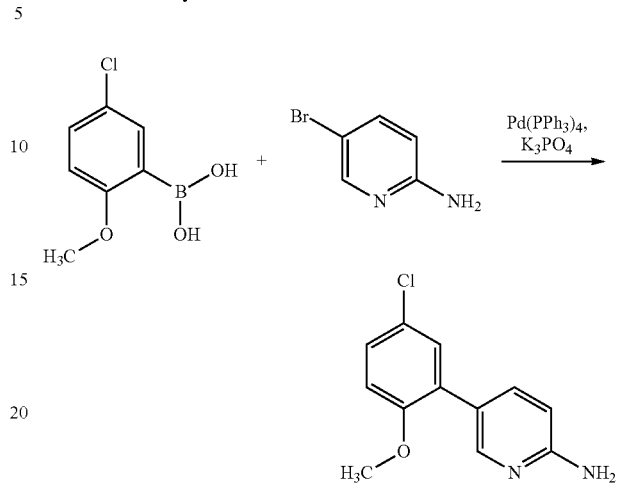

A stirred solution of 5-bromopyridin-2-amine (77 mg, 0.45 mmol, 1.0 eq.), 5-chloro-2-methoxyphenylboronic acid (100 mg, 0.54 mmol, 1.2 eq.), and $K_3PO_4$ (114 mg, 0.54 mmol, 1.2 eq.) in a mixture of toluene (20 mL) and water (10 mL) was degassed with argon for 30 min. Pd $(PPh_3)_4$ (10.4 mg 0.009 mmol 0.02 eq.) was added and the reaction mixture was heated to 80° C. for 8 h after which time it was allowed to cool to RT. The reaction mixture was then filtered and the filtrate was concentrated under reduced pressure. The resulting material was diluted with ethyl acetate (10 mL), then washed with chilled water (10 mL) and brine (10 mL). The organic layer was dried over $Na_2SO_4$ and concentrated under reduced pressure to obtain crude product. This material was purified by flash chromatography (over silica gel 100-200 mesh) eluting with 20-25% ethyl acetate in petroleum ether to obtain 5-(5-chloro-2-methoxyphenyl)pyridin-2-amine (80 mg; 59.7%).

Monomer Synthesis Procedure L

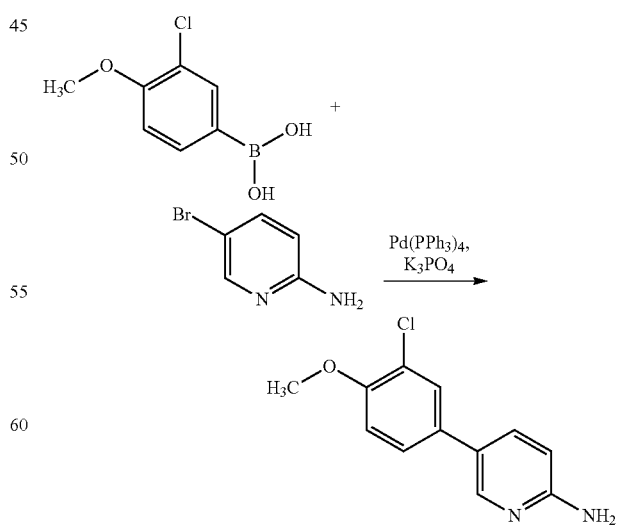

A stirred solution of 5-bromopyridin-2-amine (77 mg, 0.45 mmol, 1.0 eq.), 5-Chloro-4-methoxyphenylboronic acid (100 mg, 0.54 mmol, 1.2 eq.), and K₃PO₄ (114 mg, 0.54 mmol, 1.2 eq.) in Toluene:water (20:10 mL) was degassed with argon for 30 min. Pd (PPh₃)₄ (10.4 mg 0.009 mmol, 0.02 eq.) was added and the reaction mixture was heated to 80° C. for 8 h after which time it was allowed to cool to RT. The reaction mixture was filtered and filtrate was concentrated under reduced pressure. The remaining material was diluted with ethyl acetate (10 mL), then washed with chilled water (10 mL) and brine (10 mL). The organic layer was dried over Na₂SO₄ and concentrated under reduced pressure to obtain crude product. This material was purified by flash chromatography (over silica gel 100-200 mesh) by eluting with 20-25% ethyl acetate in petroleum ether to obtain 5-(5-chloro-4-methoxyphenyl)pyridin-2-amine (90 mg, 67.1%).

Monomer Synthesis Procedure M

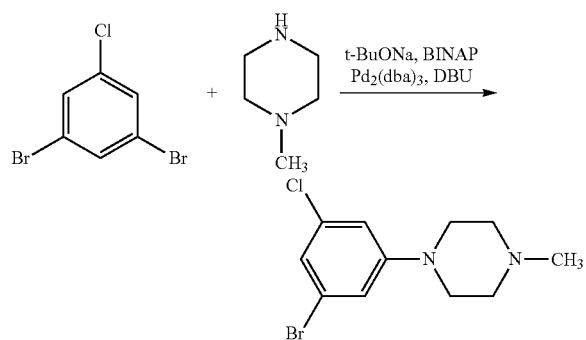

Step 1: BINAP (0.414 g, 0.667 mmol, 0.009 eq.), Pd₂(dba)₃ (0.300 g, 0.222 mmol, 0.003 eq.), DBU (9.7 g, 59.99 mmol, 0.81 eq.) and sodium t-butoxide (10.6 g, 111.1 mmol, 1.5 eq.) were added to a stirred solution of 1,3-dibromo-5-chlorobenzene (20 g, 74.1 mmol, 1.0 eq.), and N-methylpiperazine (6.7 g, 66.7 mmol, 0.9 eq.) in toluene (200 mL) under a nitrogen atmosphere. The reaction mixture was heated to 100° C. for 48 h after which time it was allowed to cool to RT. The reaction mixture was then filtered and the filtrate was concentrated under reduced pressure. The resulting crude material was diluted with ethyl acetate (200 mL) then washed with chilled water (100 mL) and brine (50 mL). The organic layer was dried over Na₂SO₄ and concentrated under reduced pressure to obtain crude product. This material was purified by flash chromatography over neutral alumina eluting with 25% ethyl acetate in petroleum ether to obtain pure 1-(3-bromo-5-chlorophenyl)-4-methylpiperazine (9.0 g; 42%).

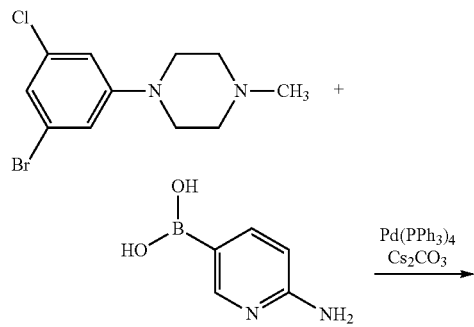

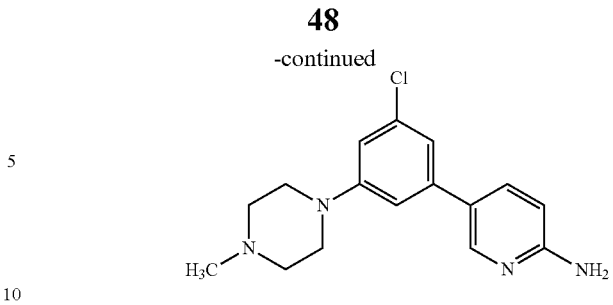

Step 2: Pd(PPh₃)₄ (0.802 g, 0.694 mmol, 0.1 eq.) and Cs₂CO₃ (3.3 g, 10.42 mmol, 1.5 eq) were added to a stirred solution of 1-(3-bromo-5-chlorophenyl)-4-methylpiperazine (2 g, 6.94 mmol, 1.0 eq.) and 6-aminopyridine-3-bornic acid (0.862 g, 0.694 mmol, 0.9 eq.) in dioxane (20 ml, previously degassed with nitrogen for 10 min). The reaction mixture was heated at 100° C. for 18 h after which time it was allowed to cool to RT. The reaction mixture was then filtered and the filtrate was diluted with ethyl acetate (100 mL) and washed with water and brine (100 mL each). The organic layer was dried over Na₂SO₄ and concentrated under reduced pressure to obtain crude product. This material was purified by flash chromatography (over silica gel 100-200 mesh) eluting with 10% methanol in DCM to afford pure 5-[5-chloro-3-(4-methylpiperazin-1-yl)phenyl]pyridin-2-amine (1.2 g; 57%).

Monomer Synthesis Procedure N

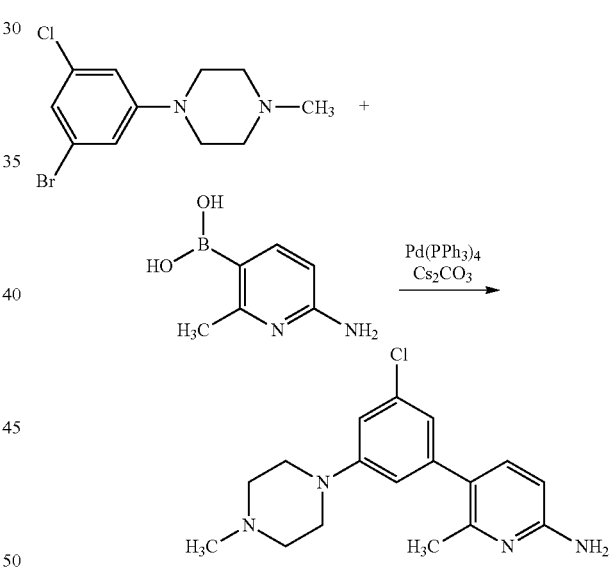

Pd(PPh₃)₄ (0.50 g, 0.454 mmol, 0.1 eq.) and Cs₂CO₃ (2.95 g, 9.08 mmol, 2.0 eq) were added to a stirred solution of 1-(3-bromo-5-chlorophenyl)-4-methylpiperazine (1.30 g, 4.54 mmol, 1.0 eq.) and 6-amino-2-methylpyridine-3-boronic acid (1.00 g g, 4.54 mmol, 1.0 eq.) in dioxane (20 mL, previously degassed with nitrogen for 10 min). The reaction mixture was heated at 80° C. for 18 h after which time it was allowed to cool to RT. The reaction mixture was then filtered and the filtrate was diluted with ethyl acetate (100 mL) and washed with water and brine (100 mL each). The organic layer was dried over Na₂SO₄ and concentrated under reduced pressure to obtain crude product. This material was purified by flash chromatography (over silica gel 100-200 mesh) eluting with 10% methanol in DCM to afford pure 5-[5-chloro-3-(4-methylpiperazin-1-yl)phenyl]-6-methyl-pyridin-2-amine (1.2 g; 85%).

Monomer Synthesis Procedure O

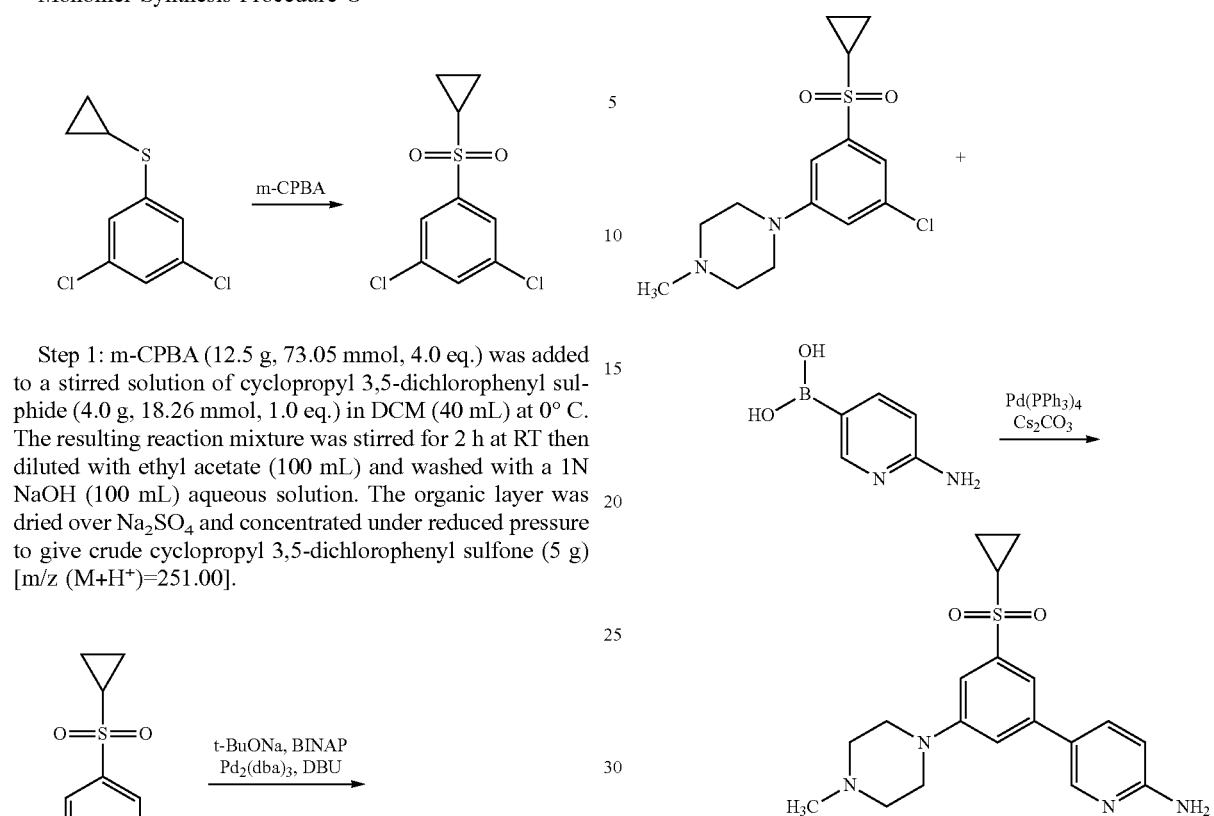

Step 1: m-CPBA (12.5 g, 73.05 mmol, 4.0 eq.) was added to a stirred solution of cyclopropyl 3,5-dichlorophenyl sulphide (4.0 g, 18.26 mmol, 1.0 eq.) in DCM (40 mL) at 0° C. The resulting reaction mixture was stirred for 2 h at RT then diluted with ethyl acetate (100 mL) and washed with a 1N NaOH (100 mL) aqueous solution. The organic layer was dried over $Na_2SO_4$ and concentrated under reduced pressure to give crude cyclopropyl 3,5-dichlorophenyl sulfone (5 g) [m/z (M+H$^+$)=251.00].

Step 2: BINAP (33 mg, 0.053 mmol, 0.009 eq.), $Pd_2(dba)_3$ (16 mg, 0.017 mmol, 0.003 eq.), DBU (784 mg, 4.840 mmol, 0.81 eq.) and sodium t-butoxide (860 mg, 8.964 mmol, 1.50 eq.) were added to a stirred solution of cyclopropyl 3,5-dichlorophenyl sulphone (1500 mg, 5.976 mmol, 1.00 eq.), and N-methylpiperazine (597 mg, 5.976 mmol, 1.00 eq.) in dioxane (20 mL) under a nitrogen atmosphere. The reaction mixture was heated to 100° C. for 16 h after which time it was allowed to cool to RT. The reaction mixture was then filtered and the filtrate was diluted with ethyl acetate (100 mL) then washed with water and brine (100 mL each). The organic layer was dried over $Na_2SO_4$ and concentrated under reduced pressure to obtain crude product. This material was purified by flash chromatography (over neutral alumina) eluting with 100% ethyl acetate to obtain pure 1-[3-chloro-5-(cyclopropylsulfonyl)phenyl]-4-methylpiperazine (1.3 g; 69%) [m/z (M+H$^+$)=315.18].

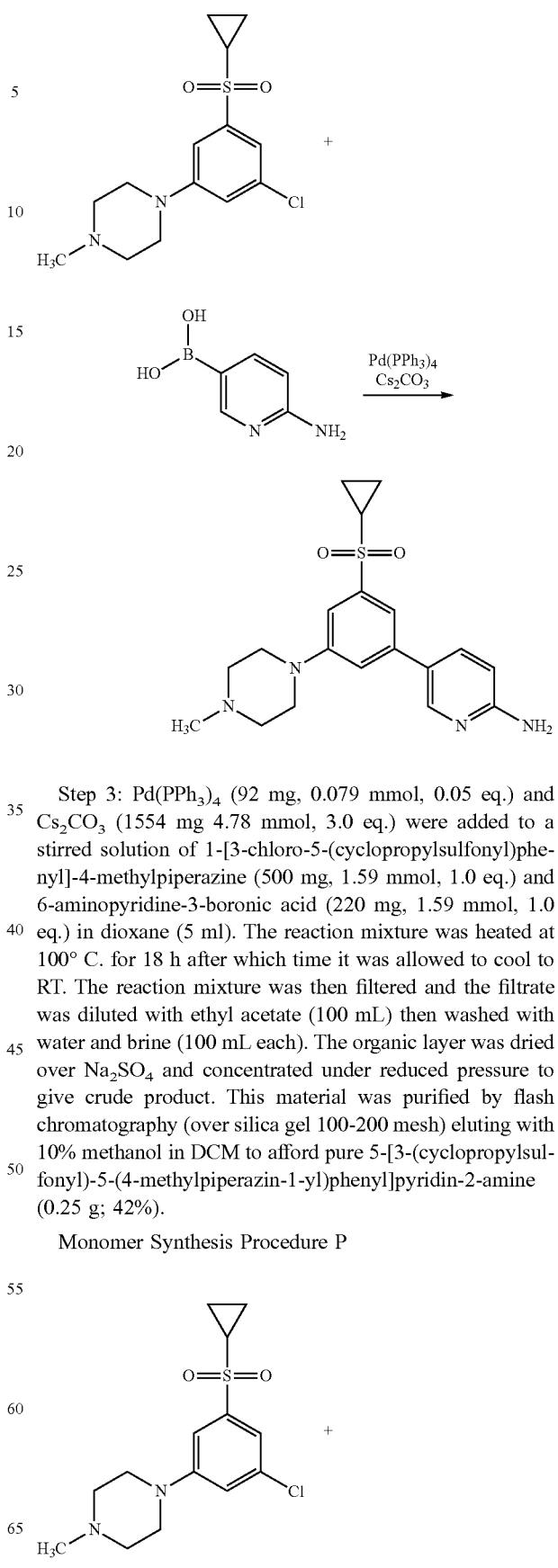

Step 3: Pd(PPh$_3$)$_4$ (92 mg, 0.079 mmol, 0.05 eq.) and $Cs_2CO_3$ (1554 mg 4.78 mmol, 3.0 eq.) were added to a stirred solution of 1-[3-chloro-5-(cyclopropylsulfonyl)phenyl]-4-methylpiperazine (500 mg, 1.59 mmol, 1.0 eq.) and 6-aminopyridine-3-boronic acid (220 mg, 1.59 mmol, 1.0 eq.) in dioxane (5 ml). The reaction mixture was heated at 100° C. for 18 h after which time it was allowed to cool to RT. The reaction mixture was then filtered and the filtrate was diluted with ethyl acetate (100 mL) then washed with water and brine (100 mL each). The organic layer was dried over $Na_2SO_4$ and concentrated under reduced pressure to give crude product. This material was purified by flash chromatography (over silica gel 100-200 mesh) eluting with 10% methanol in DCM to afford pure 5-[3-(cyclopropylsulfonyl)-5-(4-methylpiperazin-1-yl)phenyl]pyridin-2-amine (0.25 g; 42%).

Monomer Synthesis Procedure P

-continued

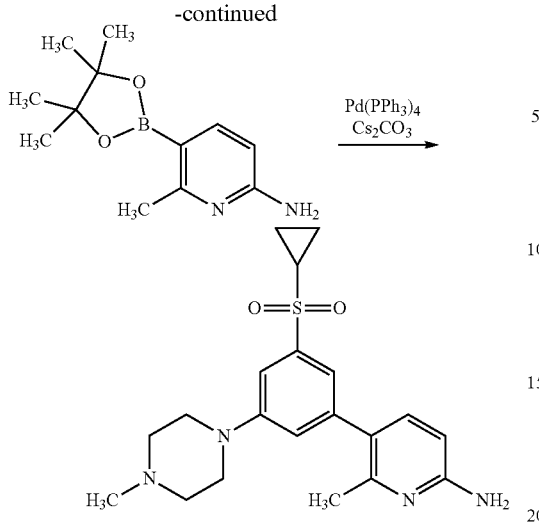

Pd(PPh₃)₄ (80 mg, 0.075 mmol, 0.1 eq.) and Cs₂CO₃ (500 mg, 1.50 mmol, 2.0 eq.) were added to a stirred solution of 1-[3-chloro-5-(cyclopropylsulfonyl)phenyl]-4-methylpiperazine (230 mg, 0.75 mmol, 1.0 eq.) and 6-methyl-5-(4,4,5,5-tetramethyl-1,3,2-dioxaborolan-2-yl)pyridin-2-amine (200 mg, 0.90 mmol, 1.2 eq.) in dioxane (5 ml). The reaction mixture was heated at 100° C. for 18 h after which time it was allowed to cool to RT. The reaction mixture was then filtered and the filtrate was diluted with ethyl acetate (100 mL) then washed with water and brine (100 mL each). The organic layer was dried over Na₂SO₄ and concentrated under reduced pressure to give crude product. This material was purified by flash chromatography (over silica gel 100-200 mesh) eluting with 10% methanol in DCM to afford pure 5-[3-(cyclopropylsulfonyl)-5-(4-methylpiperazin-1-yl)phenyl]-6-methylpyridin-2-amine (160 mg; 57%) [m/z (M+H⁺) =387.29].

Monomer Synthesis Procedure Q

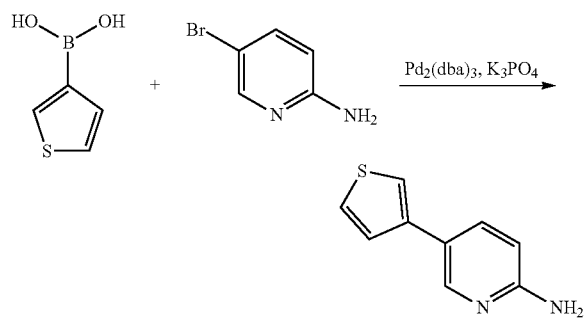

Pd₂(dba)₃ (72 mg, 0.078 mmol, 0.01 eq.) and K₃PO₄ (3.32 g, 15.63 mmol, 2.0 eq.) were added to a solution of thiophene-3-boronic acid (1.00 g, 7.815 mmol, 1.0 eq.) and 5-bromopyridin-2-amine (1.76 g, 10.159 mmol, 1.3 eq.) in n-butanol (100 mL) under an argon atmosphere. The reaction mixture was heated to 90° C. for 16 h after which time it was allowed to cool to RT. The reaction mixture was then diluted with ethyl acetate (100 mL) then washed with water and brine (100 mL each). The organic layer was dried over Na₂SO₄ and concentrated under reduced pressure to obtain crude product. This material was purified by flash chromatography (over neutral alumina) eluting with 100% ethyl acetate to obtain pure 5-(thiophen-3-yl)pyridin-2-amine (200 mg; 15%).

Monomer Synthesis Procedure R

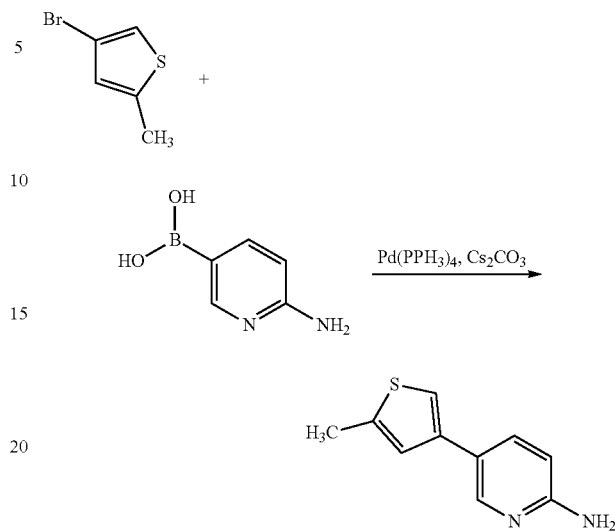

Pd(PPH₃)₄ (651 mg, 0.564 mmol, 0.1 eq.) and Cs₂CO₃ (5.50 g, 16.92 mmol, 3.0 eq.) were added to a stirred solution of 4-bromo-2-methylthiophene (1.00 g, 5.64 mmol, 1.0 eq.) and 6-aminopyridin-3-ylboronic acid (1.10 g, 8.47 mmol, 1.5 eq.) in a mixture of dioxane (10 ml) and water (3 ml) at RT under a nitrogen atmosphere. The reaction mixture was heated to 90° C. for 16 h after which time it was allowed to cool to RT. The reaction mixture was then diluted with ethyl acetate (100 mL) then washed with water and brine (100 mL each). The organic layer was dried over Na₂SO₄ and concentrated under reduced pressure to obtain crude product. This material was purified by flash chromatography (over neutral alumina) eluting with 100% ethyl acetate to obtain pure 5-(5-methylthiophen-3-yl)pyridin-2-amine (1.0 g; 46.7%).

Monomer Synthesis S

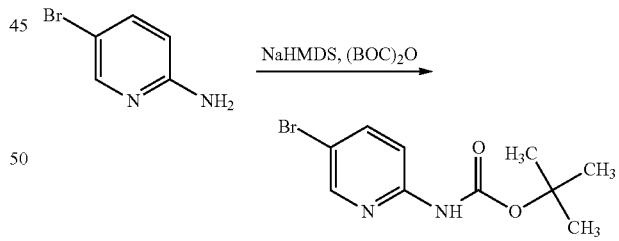

Step 1: NaHMDS (2M in THF, 361 mL, 722.5 mmol, 2.5 eq.) was added to a stirred solution of 5-bromopyridin-2-amine (50 g, 289.0 mmol, 1.0 eq.) in THF (50 ml) at 0° C. The reaction mixture was stirred at 0° C. for 30 min. followed by the addition of (Boc)₂O (82 mL, 375.7 mmol, 1.3 eq.) dissolved in THF (50 mL). The reaction mixture was stirred at RT for 16 h then quenched with ice water and extracted with ethyl acetate. The combined organic layers were dried over Na₂SO₄ and concentrated under reduced pressure to obtain crude product which was purified by trituration with petroleum ether to obtain pure tert-butyl (5-bromopyridin-2-yl)carbamate (60 g; 76%).

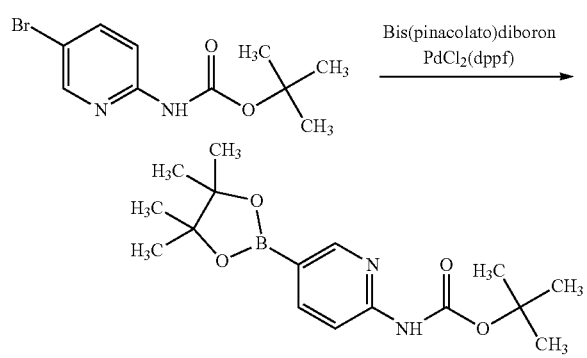

Step 2: Potassium acetate (21.50 g, 219.70 mmol, 3.0 eq.) and PdCl₂(dppf).CH₂Cl₂ (2.99 g, 3.67 mmol, 0.05 eq.) were added to a stirred solution of (5-bromopyridin-2-yl)carbamate (20.00 g, 73.26 mmol, 1.0 eq.) and bis(pinacolato)diboron (37.00 g, 146.50 mmol, 2.0 eq.) in dioxane (200 mL) under a nitrogen atmosphere at RT. The reaction mixture was heated to 100° C. for 16 h after which time it was allowed to cool to RT. The reaction mixture was then filtered and diluted with ethyl acetate (100 mL) then washed with water and brine (100 mL each). The organic layer was dried over Na₂SO₄ and concentrated under reduced pressure to obtain crude product. This material was purified by flash chromatography (over neutral alumina) eluting with 50% ethyl acetate in petroleum ether to obtain pure tert-butyl-(5-(4,4,5,5-tetramethyl-1,3,2-dioxaborolan-2-yl)pyridin-2-yl)carbamate (15.0 g; 64%).

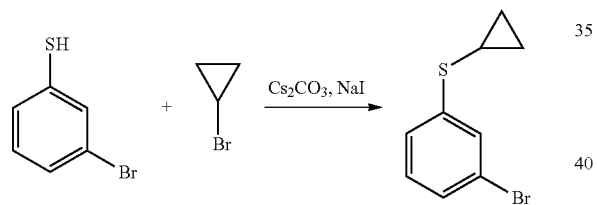

Step-3: Bromocyclopropane (13 g, 105.82 mmol, 2.0 eq.), CS₂CO₃ (51 g, 158.73 mmol, 3.0 eq.) and NaI (793 mg, 5.29 mmol, 0.1 eq.) were added to a stirred solution of 3-bromobenzenethiol (10 g, 52.91 mmol, 1.0 eq.) in DMF (100 mL) at RT. The reaction mixture was heated to 120° C. for 16 h after which time it was allowed to cool to RT. The reaction mixture was then washed with chilled water and brine (100 mL each). The organic layer was dried over Na₂SO₄ and concentrated under reduced pressure to obtain crude product. This material was purified by flash chromatography (over silica gel 100-200 mesh) eluting with 100% petroleum ether to obtain pure 1-bromo-3-(cyclopropylsulfanyl)benzene (7.0 g; 57.7%).

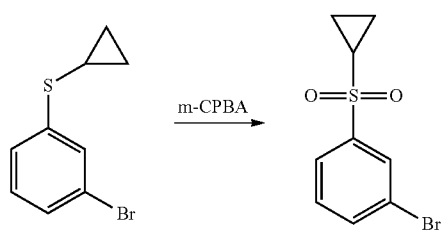 [SMILES: Brc1cccc(SC2CC2)c1 ; O=S(=O)(c1cccc(Br)c1)C1CC1]

Step 4: m-CPBA (21 g, 122.80 mmol, 4.0 eq.) was added to a stirred solution of 1-bromo-3-(cyclopropylsulfanyl)benzene (7 g, 30.70 mmol, 1.0 eq.) in DCM (200 mL) at 0° C. The reaction mixture was stirred for 16 h at RT. The reaction mixture concentrated under reduced pressure and then diluted with ethyl acetate (200 mL) and washed with a 1N NaOH aqueous solution (200 mL). The organic layer was dried over Na₂SO₄ and concentrated under reduced pressure to obtain crude 1-bromo-3-(cyclopropylsulfonyl)benzene (7.0 g).

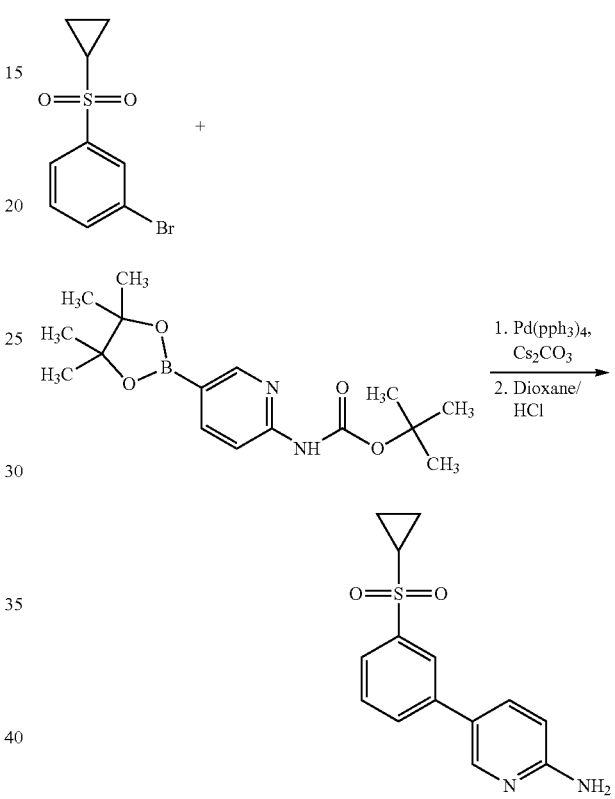

Steps 5/6: 5-(4,4,5,5-Tetramethyl-1,3,2-dioxaborolan-2-yl)pyridin-2-yl)carbamate (12.3 g, 38.60 mmol, 1.0 eq.), Pd(PPh₃)₄ (4.4 g, 3.86 mmol, 0.1 eq.) and Cs₂CO₃ (37.6 g, 115.80 mmol, 3.0 eq.) were added to a stirred solution of 1-bromo-3-(cyclopropylsulfonyl)benzene (10.0 g, 38.60 mmol, 1.0 eq.) in a mixture of dioxane (200 ml) and water (50 ml) previously degassed with nitrogen for 10 min. The reaction mixture was heated to 100° C. for 18 h after which time it was allowed to cool to RT. The reaction mixture was filtered and diluted with ethyl acetate (100 mL) then washed with water and brine (100 mL each). The organic layer was dried over Na₂SO₄ and concentrated under reduced pressure to obtain crude tert-butyl {5-[3 (cyclopropylsulfonyl)phenyl]pyridin-2-yl}carbamate (25.0 g). This material was dissolved in HCl in dioxane (4N, 50 ml) at 0° C. The reaction mixture was stirred for 16 h at RT then quenched with ice water and extracted with ethyl acetate (300 ml). The aqueous layer was basified with NaHCO₃ and extracted with ethyl acetate. The combined organic layers were washed with water and brine then dried over Na₂SO₄ and concentrated under reduced pressure to obtain crude 5-[3 (cyclopropylsulfonyl)phenyl]pyridin-2-amine (14 g) which was used without further purification.

Monomer Synthesis T

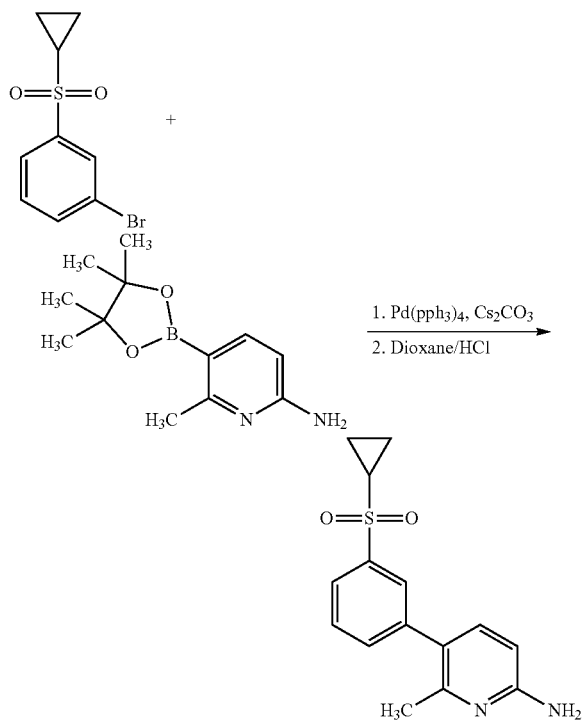

6-Methyl-5-(4,4,5,5-tetramethyl-1,3,2-dioxaborolan-2-yl)pyridin-2-amine (150 mg, 0.681 mmol, 1.0 eq.), Pd(pph₃)₄ (78 mg, 0.068 mmol, 0.1 eq.) and Cs₂CO₃ (440 mg, 1.362 mmol, 2.0 eq.) were added to a stirred solution of 1-bromo-3-(cyclopropylsulfonyl)benzene (180 mg, 0.681 mmol, 1.0 eq.) in dioxane (5 mL) previously degassed with nitrogen for 10 min. The reaction mixture was heated to 100° C. for 18 h after which time it was allowed to cool to RT. The reaction mixture was then filtered and the filtrate was diluted with ethyl acetate (100 mL) then washed with water and brine (100 mL each). The organic layer was dried over Na₂SO₄ and concentrated under reduced pressure to obtain crude product. This material was purified by flash chromatography (over neutral alumina) eluting with 10% methanol in DCM to give 5-[3-(cyclopropylsulfonyl)phenyl]-6-methylpyridin-2-amine (200 mg; 99%).

Monomer Synthesis U

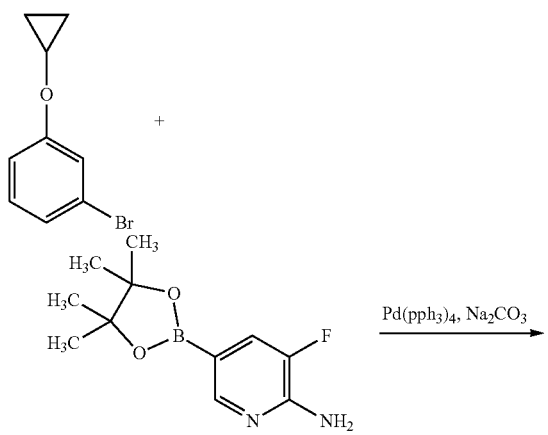

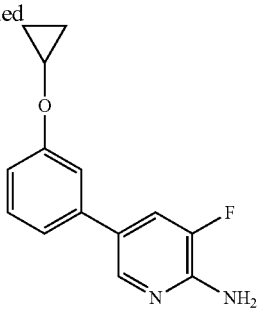

Pd(PPh₃)₄ (0.14 g, 0.12 mmol, 0.1 eq.) and Na₂CO₃ (0.53 g, 5.04 mmol, 3.6 eq.) were added to a stirred solution of 1-bromo-3-(cyclopropyloxy)benzene (0.30 g, 1.40 mmol, 1.0 eq.) and 3-fluoro-5-(4,4,5,5-tetramethyl-1,3,2-dioxaborolan-2-yl)pyridin-2-amine (0.50 g, 2.10 mmol, 1.5 eq.) in a mixture of dioxane (3 mL) and water (1.5 mL) previously degassed with nitrogen for 10 min. The reaction mixture was heated to 100° C. for 16 h after which time it was allowed to cool to RT. The reaction mixture was then filtered and the filtrate was diluted with ethyl acetate (100 mL) then washed with water and brine (100 mL each). The organic layer was dried over Na₂SO₄ and concentrated under reduced pressure to afford crude product. This material was purified by flash chromatography (over silica gel 100-200 mesh) eluting with 40% EtOAc in petroleum ether to afford pure 5-[3-(cyclopropyloxy)phenyl]-3-fluoropyridin-2-amine (250 mg; 73.5%)

Monomer Synthesis V

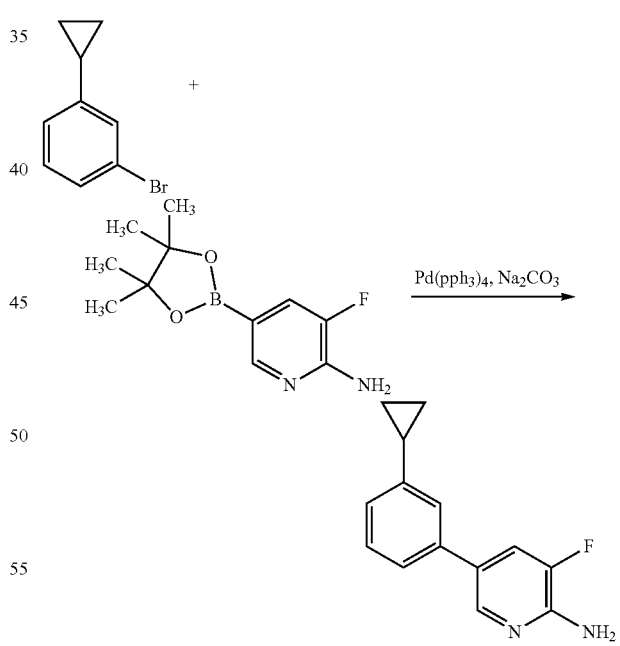

Pd(PPh₃)₄ (1.1 g, 1.03 mmol, 0.1 eq.) and Na₂CO₃ (1.6 g, 15.37 mmol, 1.5 eq.) were added to a stirred solution of 1-bromo-3-cyclopropylbenzene (2.0 g, 10.25 mmol, 1.0 eq.) and 3-fluoro-5-(4,4,5,5-tetramethyl-1,3,2-dioxaborolan-2-yl)pyridin-2-amine (2.6 g, 11.28 mmol, 1.1 eq.) in a mixture of dioxane (3 mL) and water (1.5 mL) previously degassed with argon for 30 min. The reaction mixture was heated to 80° C. for 2 h after which time it was allowed to cool to RT.

The reaction mixture was then filtered through a bed of celite and the filtrate was concentrated under reduced pressure. The residue was dissolved in ethyl acetate (100 mL) then washed with water and brine (100 mL each). The organic layer was dried over Na$_2$SO$_4$ and concentrated under reduced pressure to afford crude product. This material was purified by flash chromatography (over silica gel 100-200 mesh) eluting with 100% EtOAc to afford pure 5-(3-cyclopropylphenyl)-3-fluoropyridin-2-amine (500 mg; 21.5%)

Monomer Synthesis W

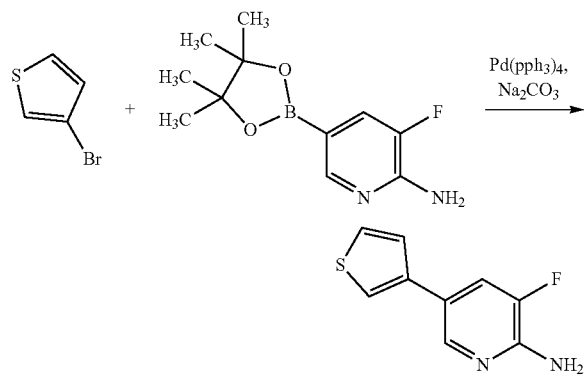

Pd(PPh$_3$)$_4$ (1.40 g, 1.22 mmol, 0.1 eq.) and Na$_2$CO$_3$ (1.94 g, 18.39 mmol, 1.5 eq.) were added to a stirred solution of 3-bromothiophene (2.00 g, 12.26 mmol, 1.0 eq.) and 3-fluoro-5-(4,4,5,5-tetramethyl-1,3,2-dioxaborolan-2-yl)pyridin-2-amine (3.20 g, 13.49 mmol, 1.1 eq.) in a mixture of dioxane (20 mL) and water (5 mL) previously degassed with argon for 30 min. The reaction mixture was heated to 80° C. for 2 h after which time it was allowed to cool to RT. The reaction mixture was then filtered and the filtrate was concentrated under reduced pressure. The residue was dissolved in ethyl acetate (100 mL) then washed with water and brine (100 mL each). The organic layer was dried over Na$_2$SO$_4$ and concentrated under reduced pressure to afford crude product. This material was purified by flash chromatography (over silica gel 100-200 mesh) eluting with 100% EtOAc to afford pure 3-fluoro-5-(thiophen-3-yl)pyridin-2-amine (1.3 g; 54.6%).

Monomer Synthesis X

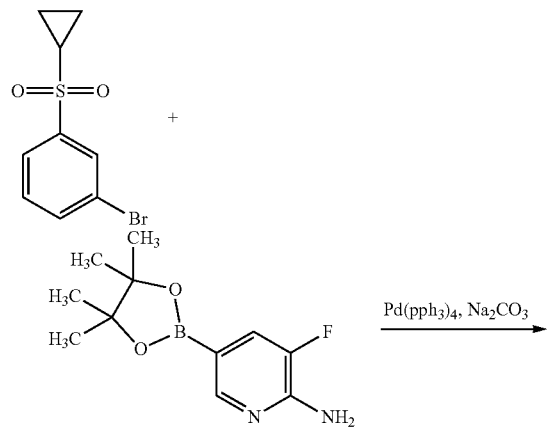

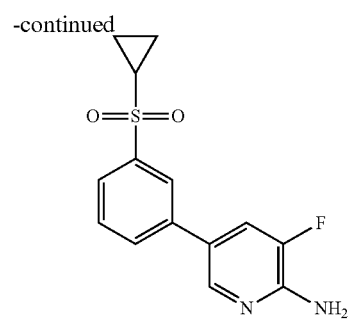

Pd(PPh$_3$)$_4$ (0.89 g, 0.77 mmol, 0.1 eq.) and Na$_2$CO$_3$ (1.20 g, 11.58 mmol, 1.5 eq.) were added to a stirred solution of 1-bromo-3-(cyclopropylsulfonyl)benzene (2.00 g, 7.72 mmol, 1.0 eq.) and 3-fluoro-5-(4,4,5,5-tetramethyl-1,3,2-dioxaborolan-2-yl)pyridin-2-amine (1.80 g, 7.72 mmol, 1.0 eq.) in a mixture of dioxane (20 mL) and water (5 mL) previously degassed with nitrogen for 10 mins. The reaction mixture was heated to 100° C. for 6 h after which time it was allowed to cool to RT. The reaction mixture was then filtered and the filtrate was diluted with ethyl acetate (100 mL) then washed with water and brine (100 mL each). The organic layer was dried over Na$_2$SO$_4$ and concentrated under reduced pressure to obtain crude product. This material was purified by flash chromatography (over silica gel 100-200 mesh) eluting with 100% ethyl acetate to yield 5-[3-(cyclopropylsulfonyl)phenyl]-3-fluoropyridin-2-amine (600 mg; 26.6%)

Synthesis of N-{5-[3-cycopropylaminol-5-(4-methylpiperazin-1-yl)phenyl]pyridin-2-yl}-2-methylpyrimidine-5-carboxamide (51)

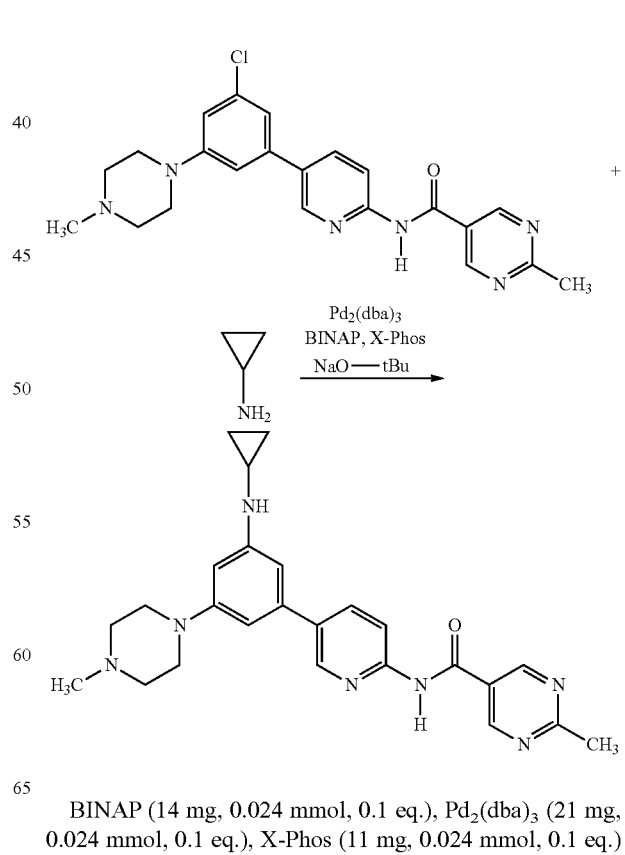

BINAP (14 mg, 0.024 mmol, 0.1 eq.), Pd$_2$(dba)$_3$ (21 mg, 0.024 mmol, 0.1 eq.), X-Phos (11 mg, 0.024 mmol, 0.1 eq.)

and NaOtBu (68 mg, 0.708 mmol, 3.0 eq.) were added to a stirred solution of N-{5-3-chloro-5-(4-methylpiperazin-1-yl)phenyl]pyridin-2-yl}-2-methylpyrimidine-5-carboxamide (100 mg, 0.236 mmol, 1.0 eq.) and cyclopropylamine (13 mg, 0.236 mmol, 1.0 eq.) in dioxane (10 mL) under a nitrogen atmosphere at RT. The reaction mixture was subsequently heated to 100° C. for 18 h after which time it was allowed to cool to RT. The reaction mixture was then filtered and the filtrate was diluted with ethyl acetate (100 mL) then washed with water and brine (100 mL each). The organic layer was dried over Na$_2$SO$_4$ and concentrated under reduced pressure to give crude product. This material was purified by flash chromatography (over silica gel100-200 mesh) eluting with 10% methanol in DCM to afford pure N-{5-[3-cycopropylaminol-5-(4-methylpiperazin-1-yl)phenyl]pyridin-2-yl}-2-methylpyrimidine-5-carboxamide (20 mg; 19.2%).

Synthesis of N-{5-[3-cyclopropropylamino-5-(4-methylpiperazin-1-yl)phenyl]-6-methylpyridin-2-yl}-2-methylpyrimidine-5-carboxamide (52)

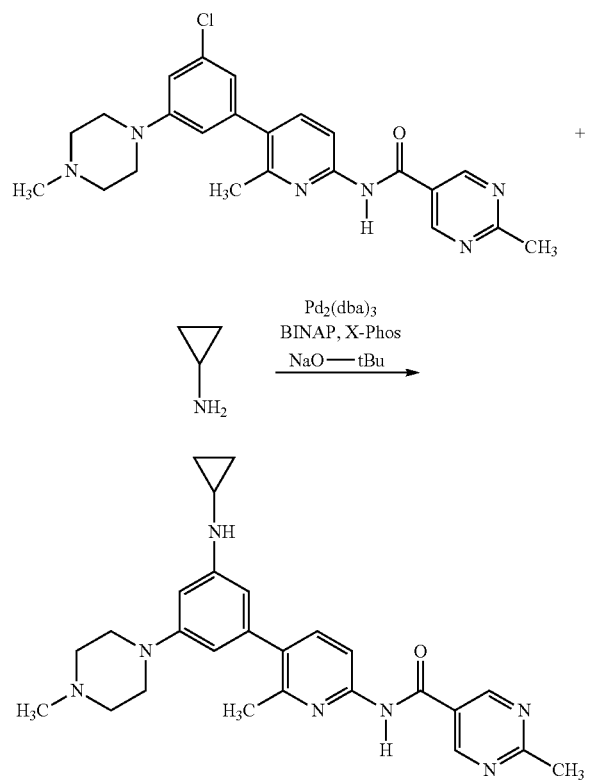

BINAP (10 mg, 0.017 mmol, 0.05 eq.), Pd$_2$(dba)$_3$ (31 mg, 0.034 mmol, 0.1 eq.), X-Phos (16 mg, 0.034 mmol, 0.1 eq.) and NaOtBu (49 mg, 0.516 mmol, 1.5 eq.) were added to a stirred solution of N-{5-[3-chloro-5-(4-methylpiperazin-1-yl)phenyl]-6-methylpyridin-2-yl}-2-methylpyrimidine-5-carboxamide (150 mg, 0.344 mmol, 1.0 eq.) and cyclopropylamine (20 mg, 0.412 mmol, 1.2 eq.) in dioxane (10 mL) under a nitrogen atmosphere at RT. The reaction mixture was subsequently heated to 100° C. for 18 h after which time it was allowed to cool to RT. The reaction mixture was then filtered and the filtrate was diluted with ethyl acetate (100 mL) then washed with water and brine (100 mL each). The organic layer was dried over Na$_2$SO$_4$ and concentrated under reduced pressure to give crude product. This material was purified by flash chromatography (over silica gel 100-200 mesh) eluting with 10% methanol in DCM to afford pure N-{5-[3-cycopropylamino-5-(4-methylpiperazin-1-yl)phenyl]pyridin-2-yl}-2-methylpyrimidine-5-carboxamide (20 mg; 12.7%).

Synthesis of N-{5-[3-cyclopropyl-5-(4-methylpiperazin-1-yl)phenyl]-6-methylpyridin-2-yl}-2-methylpyrimidine-5-carboxamide (53)

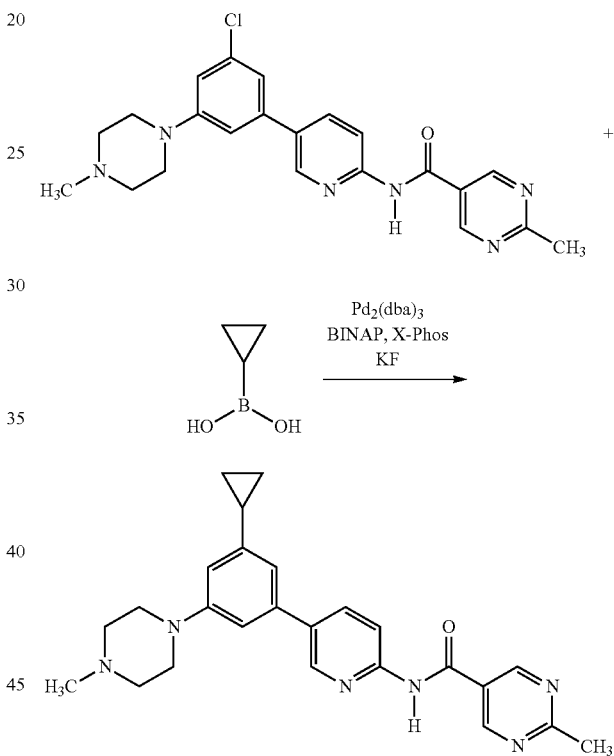

BINAP (7 mg, 0.012 mmol, 0.05 eq.) Pd$_2$(dba)$_3$ (21 mg, 0.024 mmol, 0.1 eq.), X-Phos (10 mg, 0.024 mmol, 0.1 eq.) and KF (27 mg, 0.472 mmol, 2.0 eq.) were added to a stirred solution of N-{5-[3-chloro-5-(4-methylpiper-azin-1-yl)phenyl]-6-methylpyridin-2-yl}-2-methylpyrimidine-5-carboxamide (100 mg, 0.236 mmol, 1.0 eq.) and cyclopropyl boronic acid (24 mg, 0.283 mmol, 1.2 eq.) in dioxane (10 mL) under a nitrogen atmosphere at RT. The reaction mixture was heated at 100° C. for 18 h after which time it was allowed to cool to RT. The reaction mixture was then filtered and the filtrate was diluted with ethyl acetate (100 mL) then washed with water and brine (100 mL each). The organic layer was dried over Na$_2$SO$_4$ and concentrated under reduced pressure to give crude product. This material was purified by preparative HPLC to afford pure N-{5-[3-cyclopropyl-5-(4-methylpiperazin-1-yl)phenyl]-6-methylpyridin-2-yl}-2-methylpyrimidine-5-carboxamide (20 mg; 19.8%).

Synthesis of N-{5-[3-chloro-5-(4-methylpiperazin-1-yl)phenyl]-3-fluoropyridin-2-yl}-2-methylpyrimidine-5-carboxamide (54)

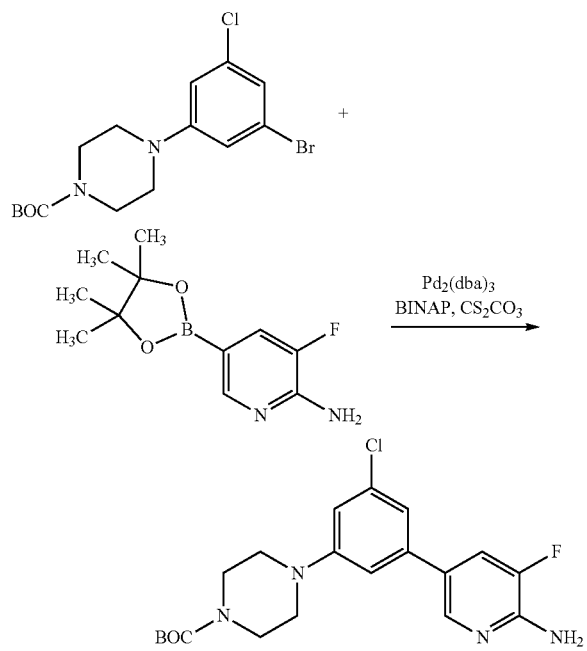

Step 1: BINAP (2.32 g, 3.70 mmol, 0.1 eq.), Pd(OAc)$_2$ (0.41 g, 1.86 mmol, 0.05 eq.) and Cs$_2$CO$_3$ (18.23 g, 55.90 mmol, 1.5 eq.) were added to a stirred solution of 1-chloro-3,5-dibromobenzene (10.00 g, 37.00 mmol, 1.0 eq.) and 6-methyl-5-(4,4,5,5-tetramethyl-1,3,2-dioxaborolan-2-yl)-3-fluoropyridin-2-amine (8.97 g, 48.10 mmol, 1.3 eq.) in toluene (200 mL). The reaction mixture was heated to 100° C. for 16 h after which time it was allowed to cool to RT. The reaction mixture was then filtered, diluted with ethyl acetate (100 mL) then washed with water and brine (100 mL each). The organic layer was dried over Na$_2$SO$_4$ and concentrated under reduced pressure to obtain crude product. This material was purified by flash chromatography (over silica gel 100-200 mesh) eluting with 5% ethyl acetate in petroleum ether to afford pure tert-butyl 4-[3-chloro-5-(5-fluoro-6-aminopyridin-3-yl)phenyl]piperazine-1-carboxylate (4.10 g; 29.4%)

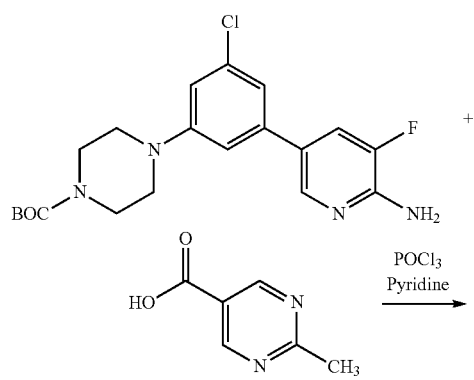

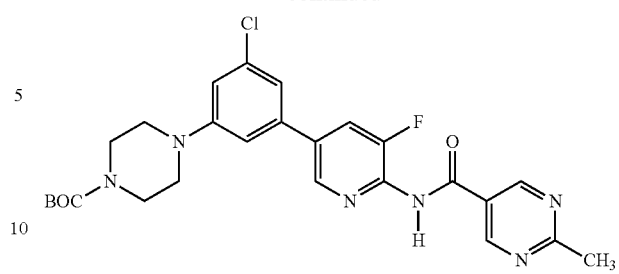

Step 2: POCl$_3$ (0.27 mL, 2.94 mmol, 3.0 eq.) was added to a stirred solution of 2-methylpyrimidine-5-carboxylic acid (136 mg, 0.98 mmol, 1.0 eq.) and tert-butyl 4-[3-chloro-5-(5-fluoro-6-aminopyridin-3-yl)phenyl]piperazine-1-carboxylate (400 mg, 0.98 mmol, 1.0 eq.) in pyridine (4 ml) at 0° C. The reaction mixture was stirred for 1 h at RT. The reaction mixture was then filtered and the filtrate was diluted with ethyl acetate (100 mL) then washed with water and brine (100 mL each). The organic layer was dried over Na$_2$SO$_4$ and concentrated under reduced pressure to obtain crude product which was purified by preparative HPLC to give pure N-{5-[3-chloro-5-(4-Boc-piperazin-1-yl)phenyl]-3-fluoropyridin-2-yl}-2-methylpyrimidine-5-carboxamide (300 mg; 58%).

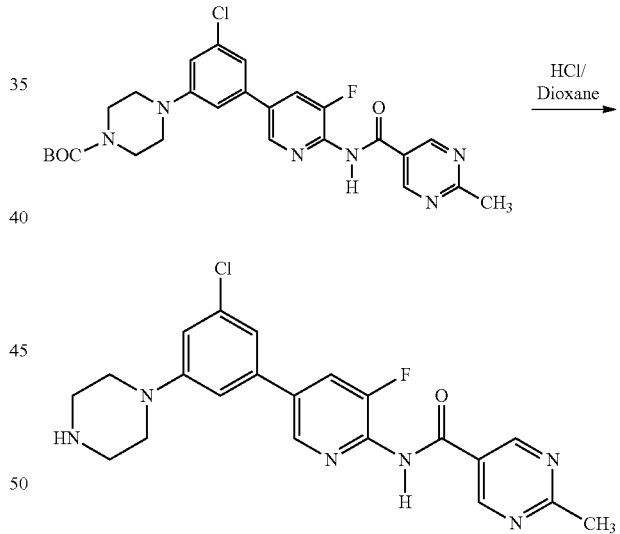

Step 3: N-{5-[3-chloro-5-(4-Boc-piperazin-1-yl)phenyl]-3-fluoropyridin-2-yl}-2-methylpyrimidine-5-carboxamide (200 mg, 0.37 mmol) was dissolved in HCl in dioxane (4N, 50 ml) and stirred for 16 h at RT. The solvent was then removed under reduced pressure and the residue was diluted with water, basified with aqeous NaHCO$_3$ and extracted with ethyl acetate (300 mL). The organic layer was separated, washed with water and brine (100 mL each) then dried over Na$_2$SO$_4$ and concentrated under reduced pressure to afford crude product. This material was triturated with hexane to afford pure N-{5-[3-cyclopropyl-5-(4-methylpiperazin-1-yl)phenyl]-6-methylpyridin-2-yl}-2-methylpyrimidine-5-carboxamide (121 mg; 75%).

Synthesis of 2-methyl-N-{5-[3-(pyrrolidin-3-ylamino)phenyl]pyridin-2-yl}pyrimidine-5-carboxamide (55)

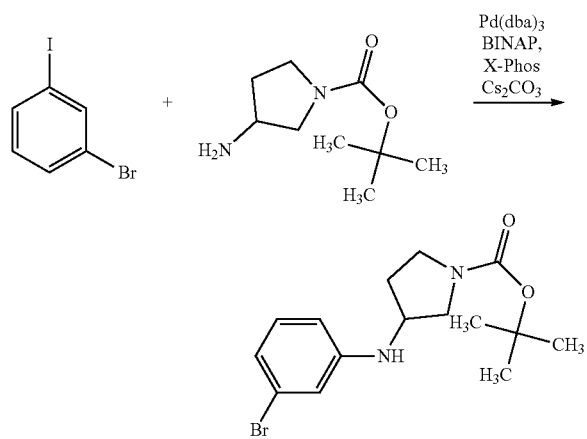

Step 1: Pd₂(dba)₂ (1.294 g, 1.413 mmol, 0.1 eq.), Xanthphos (0.818 g, 1.413 mmol, 0.1 eq.) and Cs₂CO₃ (6.890 g, 21.010 mmol, 1.5 eq.) were added to a stirred solution of 1-bromo-3-iodobenzene (4.000 g, 14.134 mmol, 1.0 eq.) and tert-butyl-3-aminopyrrolidine-1-carboxylate (2.633 g, 14.134 mmol, 1.0 eq.) in dioxane (50 mL) under argon atmosphere at RT. The reaction mixture was heated to 100° C. for 16 h after which time it was allowed to cool to RT. The reaction mixture was then filtered, diluted with ethyl acetate (100 mL) then washed with water and brine (100 mL each). The organic layer was dried over Na₂SO₄ and concentrated under reduced pressure to obtain crude product. This material was purified by flash chromatography (over silica gel 100-200 mesh) eluting with 30% ethyl acetate in petroleum ether to afford pure tert-butyl-3-[(3-bromophenyl)amino]pyrrolidine-1-carboxylate (1.0 g; 20.8%).

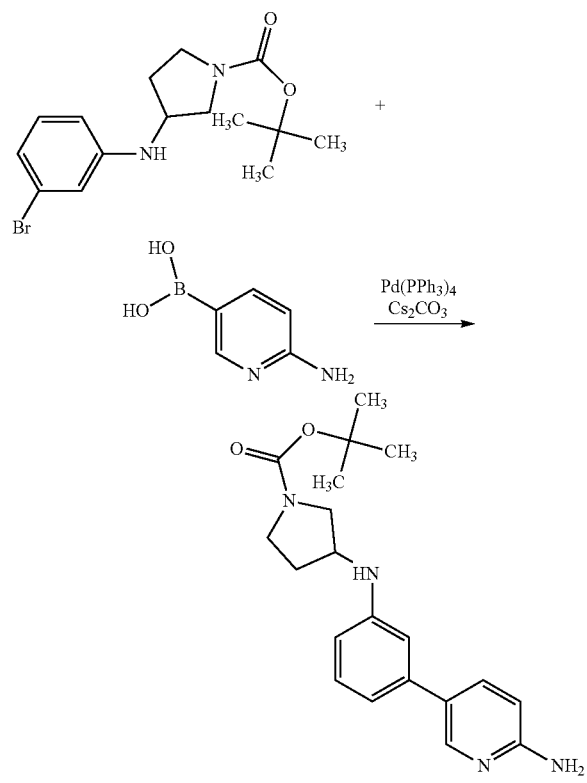

Step 2: Pd (PPh₃)₄ (169 mg, 0.147 mmol, 0.05 eq.) and Cs₂CO₃ (2.867 g, 8.823 mmol, 3.0 eq) were added to a stirred solution of tert-butyl-3-[(3-bromophenyl)amino]pyrrolidine-1-carboxylate (1.000 g, 2.941 mmol, 1.0 eq.) and 6-aminopyridin-3-ylboronic acid (0.405 g, 2.941 mmol, 1.0 eq.) in a mixture of dioxane (30 ml) and water (10 ml) at RT under a argon atmosphere. The reaction mixture was heated to 100° C. for 16 h after which time it was allowed to cool to RT. The reaction mixture was then filtered and the filtrate was concentrated under reduced pressure. The residue was diluted with ethyl acetate (100 mL) then washed with water and brine (100 mL each). The organic layer was dried over Na₂SO₄ and concentrated under reduced pressure to give crude product. This material was purified by flash chromatography (over silica gel 100-200 mesh) eluting with 40% ethyl acetate in petroleum ether to afford pure tert-butyl-3-{[3-(6-aminopyridin-3-yl)phenyl]amino}pyrrolidine-1-carboxylate (300 mg; 29%).

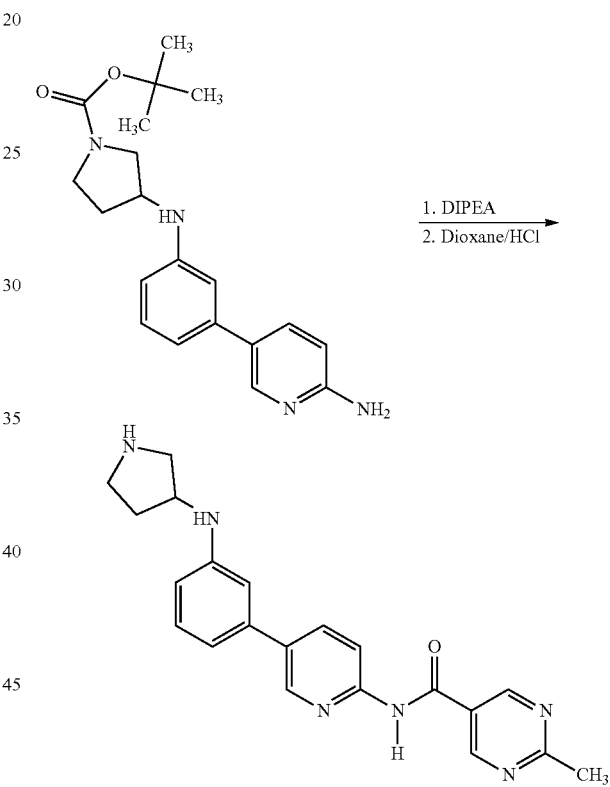

Steps 3/4: 2-Chloro-1-methylpyridinium iodide (288 mg, 11.299 mmol, 2.0 eq.) and DIPEA (0.2 mL) were added to a stirred solution of tert-butyl-3-{[3-(6-aminopyridin-3-yl)phenyl]amino}pyrrolidine-1-carboxylate (200 g, 0.565 mmol, 1.0 eq.) and 2-methyl-pyrimidine-5-carboxylic acid (78 mg, 0.565 mmol, 1.0 eq.) in THF (20 mL) at RT. The reaction mixture was stirred for 48 hours at RT then diluted with ethyl acetate (100 mL) then washed with water and brine (100 mL each). The organic layer was dried over Na₂SO₄ and concentrated under reduced pressure to obtain crude product. This material was purified by preparative HPLC then dissolved in a solution of HCl in dioxane (4N, 50 ml). After stirring for 1 hour at RT, the reaction mixture was concentrated under reduced pressure and the final product was isolated by trituration with pentane to give 2-methyl-N-{5-[3-(pyrrolidin-3-ylamino)phenyl]pyridin-2-yl}pyrimidine-5-carboxamide (55) (40 mg; 17%).

Synthesis of 2-[(2-aminoethyl)amino]-N-[5-(3-cyclopropylphenyl)pyridin-2-yl]pyrimidine-5-carboxamide (56)

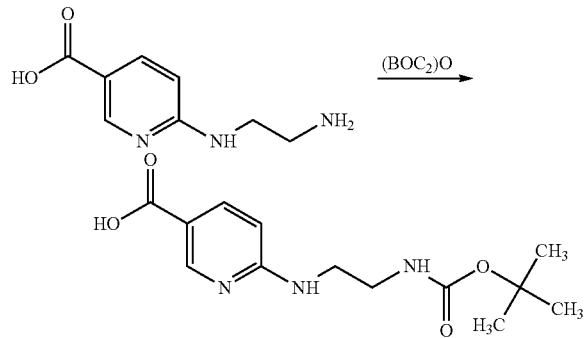

Step 1: TEA (1.116 g, 11.049 mmol, 4.0 eq.) and (Boc)₂O (1.204 g, 5.524 mmol, 2.0 eq.) were added to a stirred solution of 6-[(2-aminoethyl)amino]pyridine-3-carboxylic acid (0.500 g, 2.762 mmol, 1.0 eq.) in methanol (5 ml). The reaction mixtures was stirred for 16 hours at RT. The reaction mixture was then concentrated under reduced pressure and the residue was dissolved in a mixture of water and acetic acid (50 mL each). After extraction with ethyl acetate (150 mL), the combined organic layers were dried over Na₂SO₄ and concentrated under reduced pressure to give crude product. Trituration with 50% ethyl acetate in petroleum ether gave pure 6-({2-[(tert-butoxycarbonyl)amino]ethyl}amino)pyridine-3-carboxylic acid (200 mg; 25.7%) [m/z (M+⁺)=282.13].

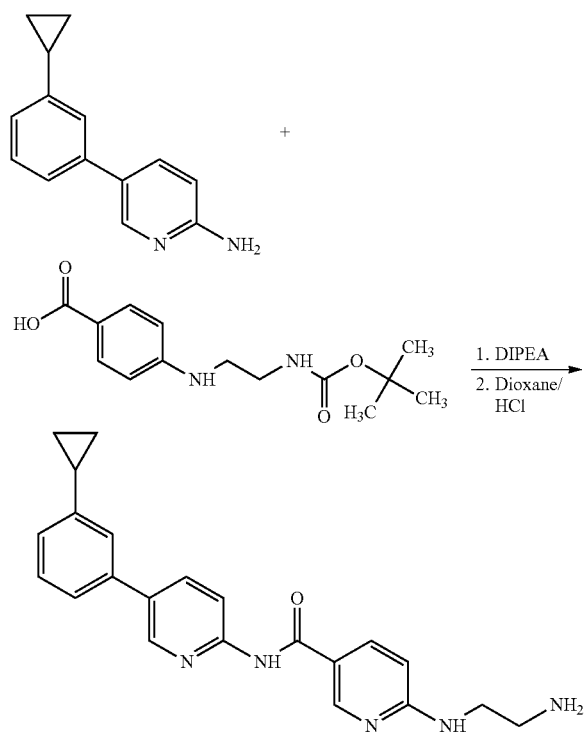

Steps 2/3: 2-Chloro-1-methylpyridinium iodide (971 mg, 3.809 mmol, 4.0 eq.) and DIPEA (0.3 ml, 1.902 mmol, 2.0 eq.) were added to a stirred solution of 5-(3-cyclopropylphenyl)pyridin-2-amine (200 mg, 0.952 mmol, 1.0 eq.) and 6-({2-[(tert-butoxycarbonyl)amino]ethyl}amino)pyridine-3-carboxylic acid (267 mg, 0.952 mmol, 1.0 eq.) in THF (30 mL). The reaction mixture was stirred for 16 hours at RT. The reaction mixture was then concentrated under reduced pressure and the resulting crude product was purified by flash chromatography (over silica gel 100-200 mesh) eluting with 30% ethyl acetate in petroleum ether. The purified material was then dissolved in a solution of HCl in dioxane (4N, 50 ml) and stirred for 1 hour at RT. The reaction mixture was then concentrated under reduced pressure to give a residue which was purified by trituration with pentane, resulting in pure 2-[(2-aminoethyl)amino]-N-[5-(3-cyclopropylphenyl)pyridin-2-yl]pyrimidine-5-carboxamide (56) (37 mg; 11.1%).

Synthesis of 2-[(2-aminoethyl)amino]-N-[5-(3-cyclopropyloxyphenyl)pyridin-2-yl]pyrimidine-5-carboxamide (58)

Steps 1/2

Steps 1/2: 2-Chloro-1-methylpyridinium iodide (679 mg, 2.66 mmol, 2.0 eq.) and DIPEA (344 mg, 463 µL, 2.66 mmol, 2.0 eq.) were added to a stirred solution of 5-[3-(cyclopropyloxy)phenyl]pyridin-2-amine (300 mg, 1.33 mmol, 1.0 eq.) and 6-({2-[(tert-butoxycarbonyl)amino]ethyl}amino)pyridine-3-carboxylic acid (373 mg, 1.33 mmol, 1.0 eq.) in THF (30 mL). The reaction mixture was stirred for 16 hours at RT. The reaction mixture was then concentrated under reduced pressure and the resulting crude product was purified by flash chromatography (over silica gel 100-200 mesh) eluting with 30% ethyl acetate in petroleum ether. The purified material was then dissolved in a solution of HCl in dioxane (4N, 50 ml) and stirred for 1 hour at RT. The reaction mixture was then concentrated under reduced pressure to give a residue which was purified by trituration with pentane, resulting in 2-[(2-aminoethyl)amino]-N-[5-(3-cyclopropyloxyphenyl)pyridin-2-yl]pyrimidine-5-carboxamide (58) (10 mg; 2.8%).

Synthesis of N-[5-(3-cyclopropylphenyl)pyridin-2-yl]-2-hydroxypyrimidine-5-carboxamide (60)

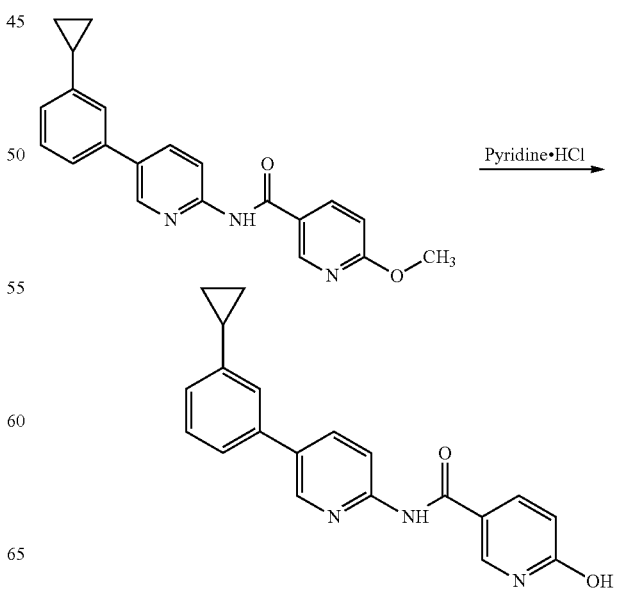

A mixture of N-[5-(3-cyclopropylphenyl)pyridin-2-yl]-2-methoxypyrimidine-5-carboxamide (250 mg, 0.722 mmol, 1.0 eq.) and pyridine hydrochloride (332 mg, 2.890 mmol, 4.0 eq.) was heated to 150° C. for 6 h after which time it was allowed to cool to RT. The reaction mixture was then diluted with ethyl acetate (100 mL) then washed with water and brine (100 mL each). The organic layer was dried over $Na_2SO_4$ and concentrated under reduced pressure to give crude product. This material was purified by preparative HPLC to give N-[5-(3-cyclopropylphenyl)pyridin-2-yl]-2-hydroxypyrimidine-5-carboxamide (60) (17 mg; 7.1%).

Synthesis of N-[5-(3-cyclopropyl-5-hydroxyphenyl)pyridin-2-yl]-2-methylpyrimidine-5-carboxamide (65)

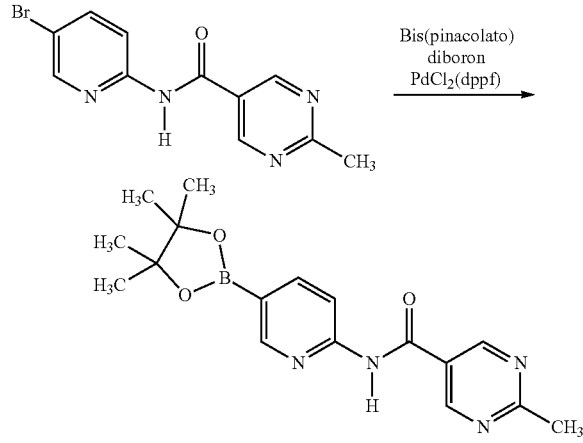

Step 1: $POCl_3$ (5.30 mL, 56.7 mmol, 3.0 eq.) was added to a stirred solution of 2-methylpyrimidine-5-carboxylic acid (2.62 g, 18.9 mmol, 1.0 eq.) and 5-bromopyridin-2-amine (3.00 g, 18.9 mmol, 1.0 eq.) in pyridine (30 mL) at 0° C. and the resulting solution was stirred for 1 h at RT. The reaction mixture was then filtered and the filtrate was diluted with ethyl acetate (100 mL) then washed with water and brine (100 mL each). The organic layer was dried over $Na_2SO_4$ and concentrated under reduced pressure to obtain N-(5-bromopyridin-2-yl)-2-methylpyrimidine-5-carboxamide (4.00 g; 71.9%).

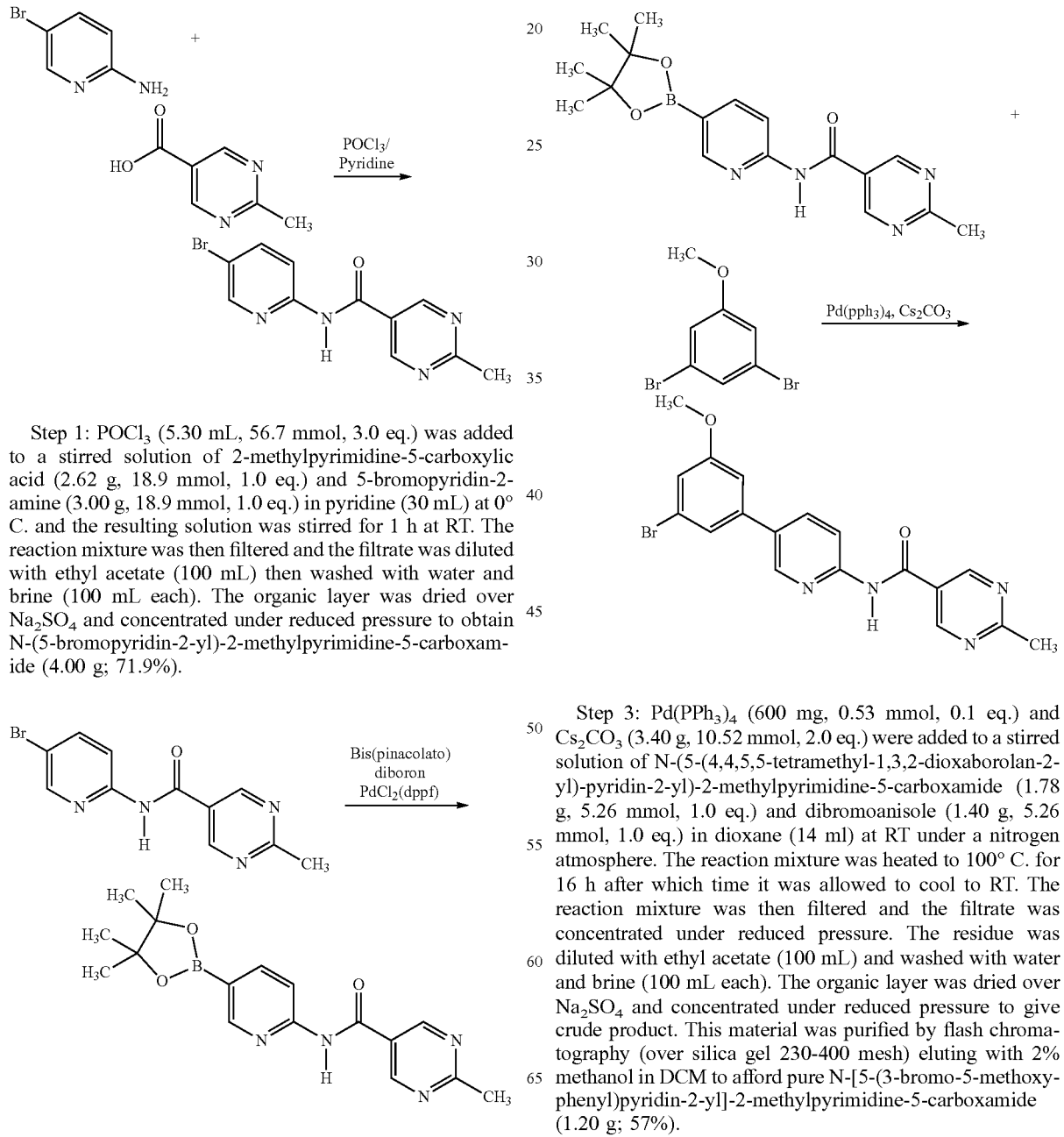

Step 2: Potassium acetate (5.30 g, 54.40 mmol, 4.0 eq.) and $PdCl_2(dppf) \cdot CH_2Cl_2$ (556 mg, 0.68 mmol, 0.05 eq.) were added to a stirred solution of N-(5-bromopyridin-2-yl)-2-methylpyrimidine-5-carboxamide (4.00 g, 13.60 mmol, 1.0 eq.) and bis(pinacolato)diboron (3.79 g, 14.90 mmol, 1.1 eq.) in dioxane (40 mL) under a nitrogen atmosphere at RT. The reaction mixture was heated to 100° C. for 16 h after which time it was allowed to cool to RT. The reaction mixture was then filtered, diluted with ethyl acetate (100 mL) and washed with water and brine (100 mL each). The organic layer was dried over $Na_2SO_4$ and concentrated under reduced pressure to give crude product. This material was purified by flash chromatography (over neutral alumina) eluting with 50% ethyl acetate in petroleum ether to obtain N-(5-(4,4,5,5-tetramethyl-1,3,2-dioxaborolan-2-yl)-pyridin-2-yl)-2-methylpyrimidine-5-carboxamide (2.00 g; 43%).

Step 3: $Pd(PPh_3)_4$ (600 mg, 0.53 mmol, 0.1 eq.) and $Cs_2CO_3$ (3.40 g, 10.52 mmol, 2.0 eq.) were added to a stirred solution of N-(5-(4,4,5,5-tetramethyl-1,3,2-dioxaborolan-2-yl)-pyridin-2-yl)-2-methylpyrimidine-5-carboxamide (1.78 g, 5.26 mmol, 1.0 eq.) and dibromoanisole (1.40 g, 5.26 mmol, 1.0 eq.) in dioxane (14 ml) at RT under a nitrogen atmosphere. The reaction mixture was heated to 100° C. for 16 h after which time it was allowed to cool to RT. The reaction mixture was then filtered and the filtrate was concentrated under reduced pressure. The residue was diluted with ethyl acetate (100 mL) and washed with water and brine (100 mL each). The organic layer was dried over $Na_2SO_4$ and concentrated under reduced pressure to give crude product. This material was purified by flash chromatography (over silica gel 230-400 mesh) eluting with 2% methanol in DCM to afford pure N-[5-(3-bromo-5-methoxyphenyl)pyridin-2-yl]-2-methylpyrimidine-5-carboxamide (1.20 g; 57%).

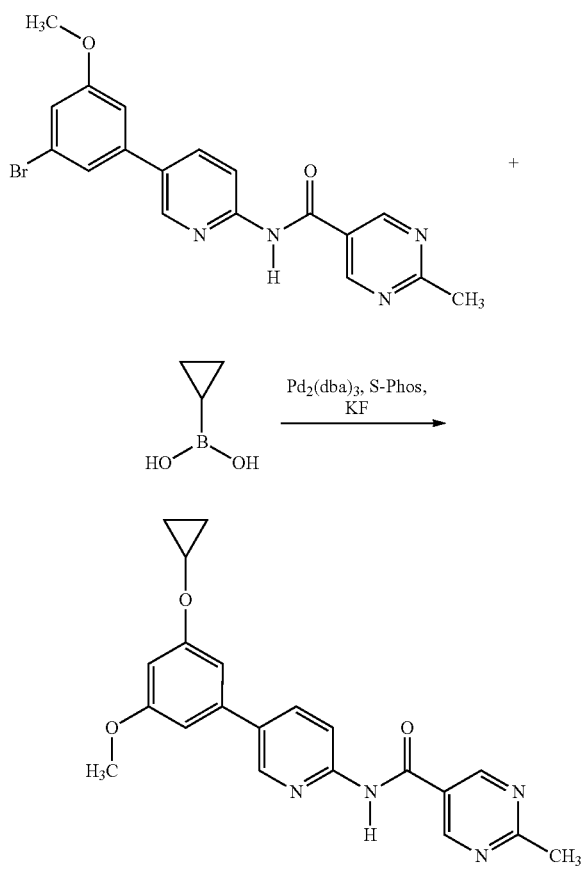

Step 4: Cyclopropylboronic acid (516 mg, 6.0 mmol, 2.0 eq.), Pd₂(dba)₃ (274 m g, 0.3 mmol, 0.1 eq.), S-Phos (123 mg, 0.3 mmol, 0.1 eq.) and KF (522 mg, 9.0 mmol, 3.0 eq.) were added to a stirred solution of N-[5-(3-bromo-5-methoxyphenyl)pyridin-2-yl]-2-methylpyrimidine-5-carboxamide (1200 mg, 3.0 mmol, 1.0 eq.) in dioxane (20 mL). The reaction mixture was heated to 100° C. for 16 h after which time it was allowed to cool to RT. The reaction mixture was then filtered, diluted with ethyl acetate (100 mL) and washed with water and brine (100 mL each). The organic layer was dried over Na₂SO₄ and concentrated under reduced pressure to afford crude N-{5-[3-(cyclopropyloxy)-5-methoxyphenyl]pyridin-2-yl}-2-methylpyrimidine-5-carboxamide (600 mg) which was used without further purification.

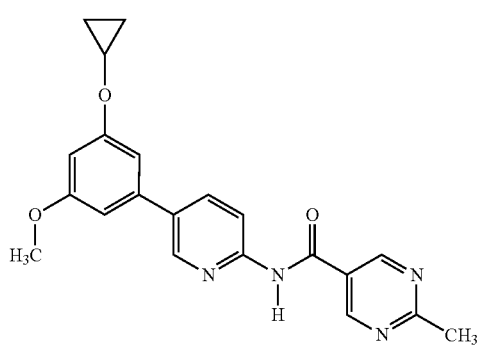

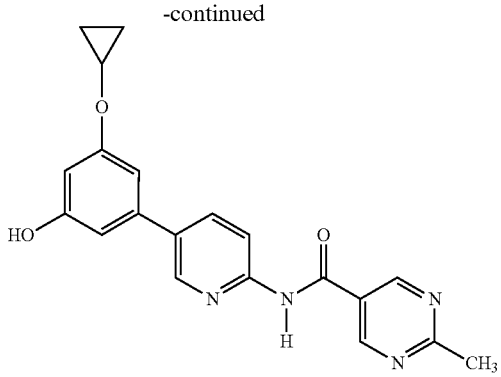

Step 5: BBr₃ (689 mg, 2.77 mmol, 2.0 eq.) was added drop-wise to a stirred solution of N-{5-[3-(cyclopropyloxy)-5-methoxyphenyl]pyridin-2-yl}-2-methylpyrimidine-5-carboxamide (500 mg, 1.38 mmol, 1.0 eq.) in DCM (5 ml) at −78° C. The reaction mixture was stirred for 2 h at −78° C. then quenched with aqueous NaHCO₃. The reaction mixture was then extracted with ethyl acetate. The organic layer was washed with water and brine then dried over Na₂SO₄ and concentrated under reduced pressure to afford crude product which was purified by preparative HPLC to give N-[5-(3-cyclopropyl-5-hydroxyphenyl)pyridin-2-yl]-2-methylpyrimidine-5-carboxamide (65) (35 mg; 7.3%).

Synthesis of N-{5-[3-(cyclopropylamino)phenyl]-3-fluoropyridin-2-yl}-2-methylpyrimidine-5-carboxamide (69)

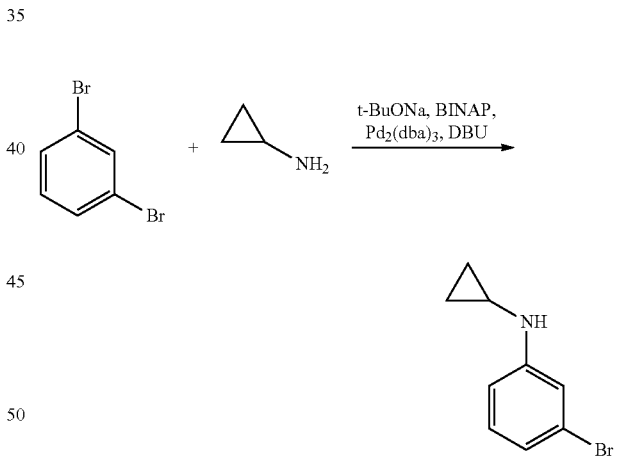

Step 1: BINAP (237 mg, 0.381 mmol, 0.009 eq.), Pd₂(dba)₃, (116 mg, 0.127 mmol, 0.003 eq.), DBU (5.5 g, 33.890 mmol, 0.8 eq.) and sodium tert-butoxide (6.1 g, 63.550 mmol, 1.5 eq.) were added to a stirred solution of 1,3-dibromobenzene (10.0 g, 42.37 mmol, 1.0 eq.) and cyclopropylamine (2.5 g, 42.37 mmol, 1.0 eq.) in toluene (50 mL) under a nitrogen atmosphere. The reaction mixture was heated to 100° C. for 16 h after which time it was allowed to cool to RT. The reaction mixture was then filtered, diluted with ethyl acetate (100 mL) and washed with water and brine (100 mL each). The organic layer was dried over Na₂SO₄ and concentrated under reduced pressure. The resulting crude material was purified by flash chromatography (over silica gel 100-200 mesh) eluting with 10% ethyl acetate in petroleum ether to obtain pure 3-bromo-N-cyclopropylaniline (2.0 g; 22.2%).

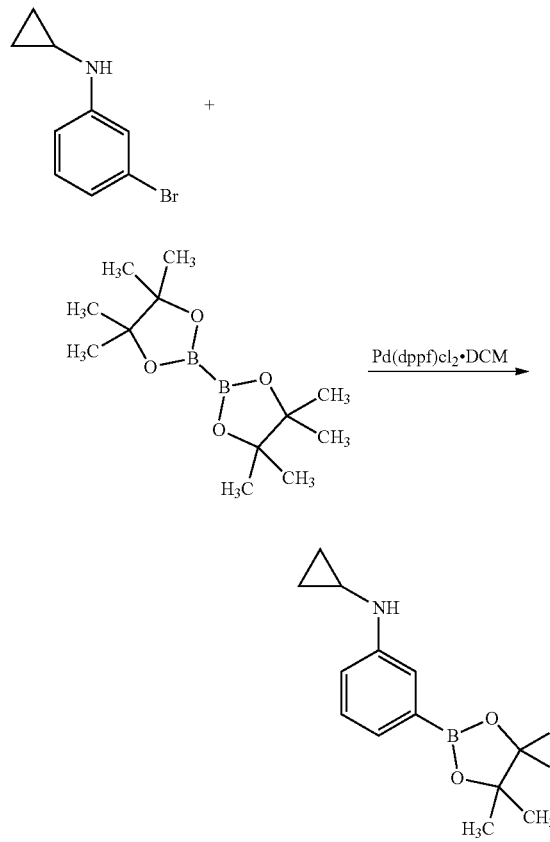

Step 2: Bis(pinacolato)diboron (1.3 g, 5.209 mmol, 1.10 eq.), potassium acetate (1.4 g, 14.208 mmol, 3.00 eq.) and Pd(dppf)Cl₂.CH₂Cl₂ (38 mg, 0.047 mmol, 0.01 eq.) were added to a stirred solution of 3-bromo-N-cyclopropylaniline (1.0 g, 4.736 mmol, 1.00 eq.) in dioxane (200 mL). The reaction mixture was heated to 90° C. for 3 h after which time it was allowed to cool to RT. The reaction mixture was then filtered, diluted with ethyl acetate (100 mL) and washed with water and brine (100 mL each). The organic layer was dried over Na₂SO₄ and concentrated under reduced pressure to obtain crude product. This material was purified by flash chromatography (over silica gel 100-200 mesh) eluting with 10% ethyl acetate in petroleum ether to obtain pure 3-(4,4,5,5-tetramethyl-1,3,2-dioxaborolan-2-yl)-N-cyclopropylaniline (1.0 g; 81.4%).

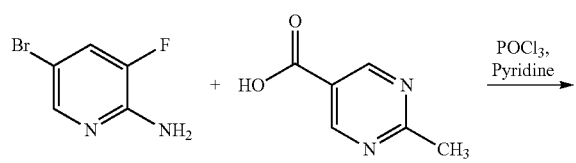

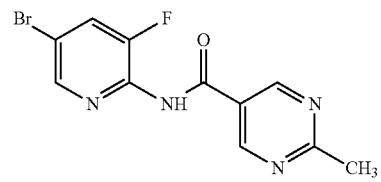

Step 3: POCl₃ (0.4 mL, 4.04 mmol, 3.0 eq.) was added to a stirred solution of 2-methylpyrimidine-5-carboxylic acid (500 mg, 3.68 mmol, 1.0 eq.) and 5-bromo-3-fluoropyridin-2-amine (700 mg, 3.68 mmol, 1.0 eq.) in pyridine (10 ml) at 0° C. The reaction mixture was stirred for 1 h at RT after which time it was poured into ice water. The resulting solid was dried to afford N-(5-bromo-3-fluoropyridin-2-yl)-2-methylpyrimidine-5-carboxamide (700 mg; 61.4%)

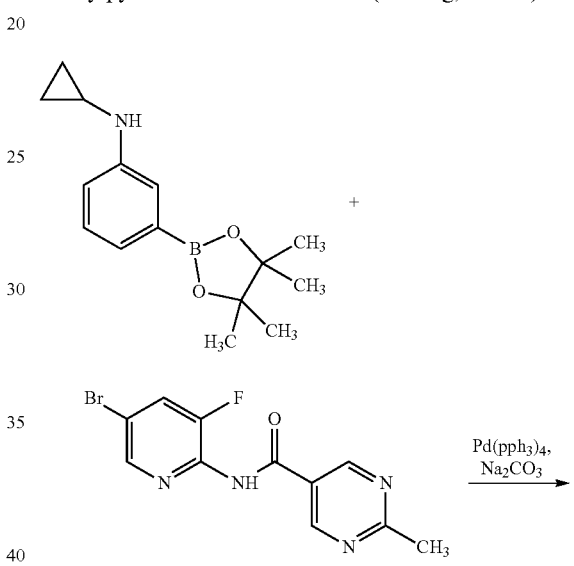

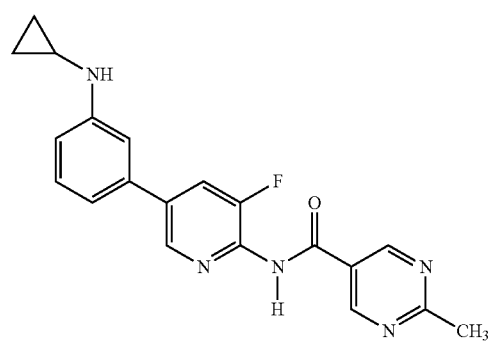

Step 4: Pd(PPh₃)₄ (177 mg, 0.154 mmol, 0.1 eq.) and Na₂CO₃ (244 mg, 2.310 mmol, 1.5 eq.) were added to a stirred solution of 3-(4,4,5,5-tetramethyl-1,3,2-dioxaborolan-2-yl)-N-cyclopropylaniline (400 mg, 1.540 mmol, 1.0 eq.) and N-(5-bromo-3-fluoropyridin-2-yl)-2-methylpyrimidine-5-carboxamide (478 mg, 1.540 mmol, 1.0 eq.) in a mixture of dioxane (20 ml) and water (5 ml) previously degassed with argon for 30 min. The reaction mixture was heated to 80° C. for 5 h after which time it was allowed to cool to RT. The reaction mixture was then filtered and the filtrate was concentrated under reduced pressure. The crude residue was dissolved in ethyl acetate then washed with water brine. The organic layer was dried over Na₂SO₄ and concentrated under reduced pressure to obtain crude product which was purified by preparative HPLC to yield N-{5-[3-(cyclopropylamino)phenyl]-3-fluoropyridin-2-yl}-2-methylpyrimidine-5-carboxamide (68) (120 mg; 21.4%).

TABLE I

| Compound ID | Structure | Chemical Name/ ¹H-NMR (CDCl₃, 400 MHz) |
| --- | --- | --- |
| 1 | 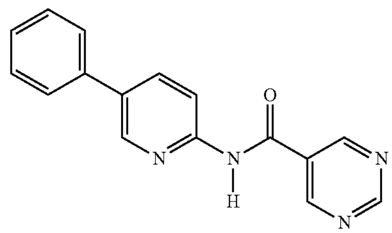 [SMILES: O=C(Nc1ccc(-c2ccccc2)cn1)c1cncnc1] | N-(biphenyl-4-yl)pyrimidine-5-carboxamide/δ 9.36 (s, 2H), 9.31 (s, 1H), 9.50 (m, 2H), 8.15 (dd, 1H, J = 9.0, 2.2 Hz), 7.52 (d, 2H, J = 7.6 Hz), 7.44 (t, 2H, J = 7.4 Hz), 7.39 (q, 1H, J = 7.4 Hz) |
| 2 | 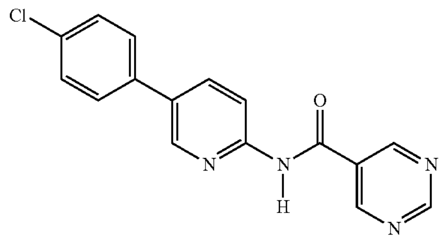 [SMILES: O=C(Nc1ccc(-c2ccc(Cl)cc2)cn1)c1cncnc1] | N-[5-(4-chlorophenyl)pyridin-2-yl]pyrimidine-5-carboxamide/ND |
| 3 | 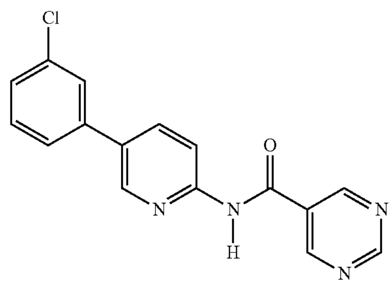 [SMILES: O=C(Nc1ccc(-c2cccc(Cl)c2)cn1)c1cncnc1] | N-[5-(3-chlorophenyl)pyridin-2-yl]pyrimidine-5-carboxamide/ δ 9.35 (s, 1H), 9.29 (s, 2H), 8.50 (d, 1H, J = 2.0 Hz), 8.41 (d, 1H, J = 8.8 Hz), 7.95 (dd, 1H, J = 8.4, 2.4 Hz), 7.53 (m, 1H), 7.43-7.33 (m, 3H) |
| 4 | 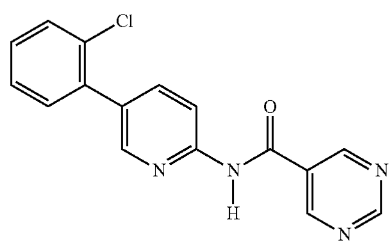 [SMILES: O=C(Nc1ccc(-c2ccccc2Cl)cn1)c1cncnc1] | N-[5-(2-chlorophenyl)pyridin-2-yl]pyrimidine-5-carboxamide/ND |
| 5 | 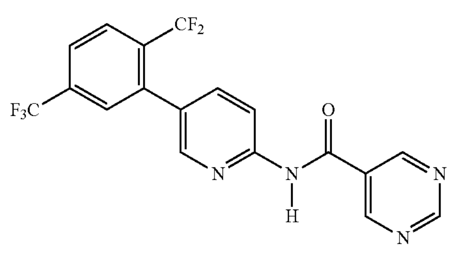 | N-[5-(2-chlorophenyl)pyridin-2-yl]pyrimidine-5-carboxamide/ δ 9.35 (s, 1H), 9.31 (s, 2H), 8.45 (d, 1H, J = 8.8 Hz), 8.27 (s, 1H), 7.91 (d, 1H, J = 8.4 Hz), 7.79 (d, 2H, J = 8.8 Hz), 7.58 (s, 1H) |
| 6 | 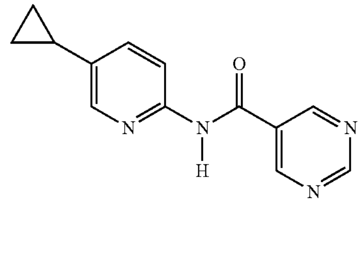 [SMILES: O=C(Nc1ccc(C2CC2)cn1)c1cncnc1] | N-(5-cyclopropylpyridin-2-yl)pyrimidine-5-carboxamide/ δ 9.37 (s, 1H), 9.27 (s, 2H), 9.00 (bs, 1H), 8.25 (d, 1H, J = 8.8 Hz), 8.09 (d, 1H, J = 2.0 Hz), 7.45 (dd, 1H, J = 8.6, 2.2 Hz), 1.90 (m, 1H, 4.4 Hz), 1.03 (m, 2H), 0.71 (m, 2H) |

TABLE I-continued

| Compound ID | Structure | Chemical Name/ ¹H-NMR (CDCl₃, 400 MHz) |
|---|---|---|
| 7 | 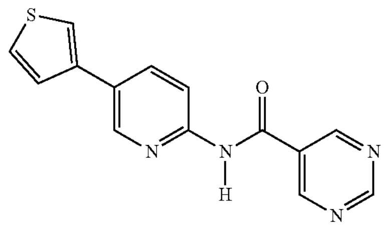 [SMILES: O=C(Nc1ccc(-c2ccsc2)cn1)c1cncnc1] | N-[5-(thiophen-3-yl)pyridin-2-yl]pyrimidine-5-carboxamide/ δ 9.40 (s, 1H), 9.34 (s, 2H), 8.54 (d, 1H, J = 1.6 Hz), 8.48 (d, 1H, J = 8.8 Hz), 8.07 (dd, 1H, J = 8.8, 2.4 Hz), 7.52 (m, 1H), 7.47 (dd, 1H, J = 5.0, 3.0 Hz), 7.37 (dd, 1H, J = 5.0, 1.4 Hz) |
| 8 | 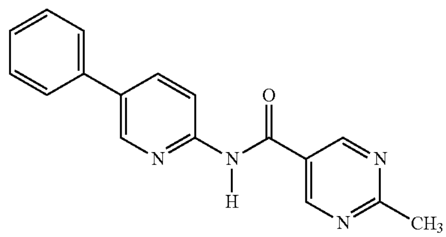 [SMILES: Cc1ncc(C(=O)Nc2ccc(-c3ccccc3)cn2)cn1] | 2-methyl-N-(5-phenylpyridin-2-yl)pyrimidine-5-carboxamide/ δ 9.19 (s, 2H), 8.96 (bs, 1H), 8.53 (d, 1H, J = 2.0 Hz), 8.45 (d, 1H, J = 8.8 Hz), 8.03 (dd, 1H, J = 8.4, 2.4 Hz), 7.57 (m, 2H), 7.48 (t, 2H, J = 7.6 Hz), 7.40 (tt, 1H, J = 7.4, 2.4 Hz), 2.83 (s, 3H) |
| 9 | 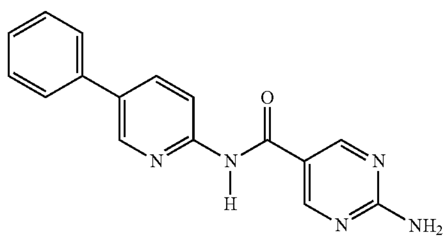 [SMILES: Nc1ncc(C(=O)Nc2ccc(-c3ccccc3)cn2)cn1] | 2-amino-N-(5-phenylpyridin-2-yl)pyrimidine-5-carboxamide δ 8.95 (bs, 1H), 8.84 (bs, 1H), 8.45 (d, 1H, J = 2.0 Hz), 8.41 (d, 1H, J = 8.8 Hz), 8.01 (dd, 1H, J = 8.8, 2.4 Hz), 7.51 (d, 2H, J = 7.2 Hz), 7.43 (t, 2H, J = 7.4 Hz), 7.35 (m, 1H), 3.32 (m, 1H), 3.02 (m, 3H) |
| 10 | 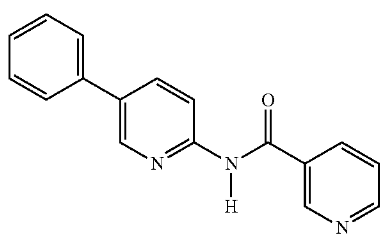 [SMILES: O=C(Nc1ccc(-c2ccccc2)cn1)c1cccnc1] | N-(5-phenylpyridin-2-yl)pyridine-3-carboxamide/ δ 9.19 (d, 1H, J = 2.0 Hz), 8.95 (bs, 1H), 8.80 (dd, 1H, J = 4.8, 1.60 Hz), 8.51 (d, 1H, J = 2.0 Hz), 8.46 (d, 1H, J = 8.0 Hz), 8.27 (dt, 1H, J = 8.0, 2.0 Hz), 8.01 (dd, 1H, J = 8.6, 2.2 Hz), 7.56 (m, 2H), 7.46 (m, 3H), 7.39 (m, 1H) |
| 11 | 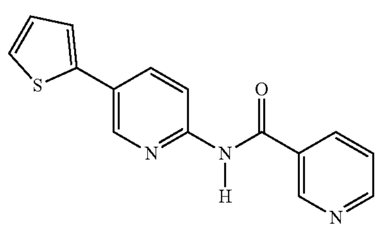 [SMILES: O=C(Nc1ccc(-c2cccs2)cn1)c1cccnc1] | N-[5-(thiophen-2-yl)pyridin-2-yl]pyridine-3-carboxamide/ δ 9.19 (d, 1H, J = 0.8 Hz), 9.02 (bs, 1H), 8.81 (dd, 1H, J = 4.8, 0.8 Hz), 8.80 (dd, 1H, J = 4.8, 1.60 Hz), 8.54 (d, 1H, J = 2.0 Hz), 8.45 (d, 1H, J = 8.8 Hz), 8.29 (dt, 1H, J = 8.4, 2.0 Hz), 8.01 (dd, 1H, J = 8.8, 2.4 Hz), 7.47 (dd, 1H, J = 8.0, 4.8 Hz), 7.34 (m, 2H), 7.11 (dd, 1H, J = 5.0, 3.8 Hz) |
| 12 | 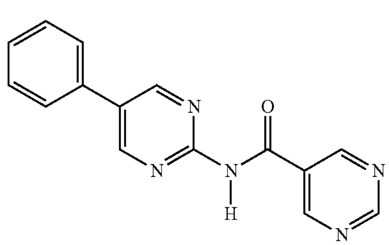 [SMILES: O=C(Nc1ncc(-c2ccccc2)cn1)c1cncnc1] | N-(5-phenylpyrimidin-2-yl)pyrimidine-5-carboxamide/ δ 9.29 (s, 1H), 9.24 (s, 2H), 8.82 (s, 2H), 7.51 -7.39 (m, 5H) |

TABLE I-continued

| Compound ID | Structure | Chemical Name/ ¹H-NMR (CDCl₃, 400 MHz) |
|---|---|---|
| 13 | 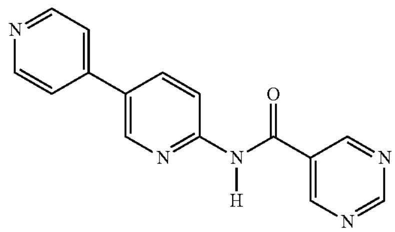 [SMILES: O=C(Nc1ccc(-c2ccncc2)cn1)c1cncnc1] | N-(3,4'-bipyridin-6-yl)pyrimidine-5-carboxamide/ND |
| 14 | 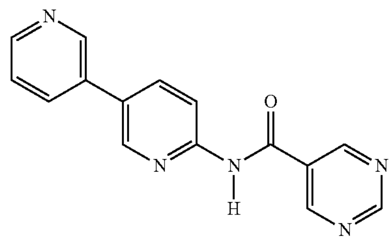 [SMILES: O=C(Nc1ccc(-c2cccnc2)cn1)c1cncnc1] | N-(3,3'-bipyridin-6-yl)pyrimidine-5-carboxamide/ND |
| 15 | 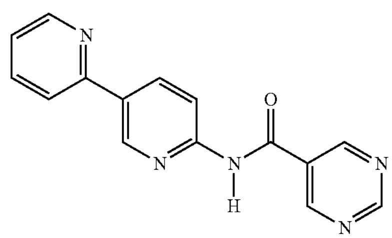 [SMILES: O=C(Nc1ccc(-c2ccccn2)cn1)c1cncnc1] | N-(3,2'-bipyridin-6-yl)pyrimidine-5-carboxamide/ND |
| 16 | 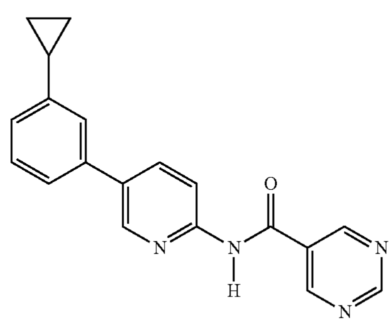 [SMILES: O=C(Nc1ccc(-c2cccc(C3CC3)c2)cn1)c1cncnc1] | N-[5-(3-cyclopropylphenyl)pyridin-2-yl]pyrimidine-5-carboxamide/ δ 9.40 (s, 1H), 9.32 (s, 2H), 9.15 (bs, 1H), 8.52 (d, 1H, J = 2.0 Hz), 7.46 (d, 1H, J = 8.8 Hz), 8.04 (dd, 1H, J = 8.8, 2.4 Hz), 7.38-7.32 (m, 2H), 7.27 (s, 1H), 7.09 (dt, 1H, J = 7.2, 1.4 Hz), 1.97 (qui, 1H, 4.2 Hz), 1.01 (m, 2H), 0.74 (m, 2H) |
| 17 | 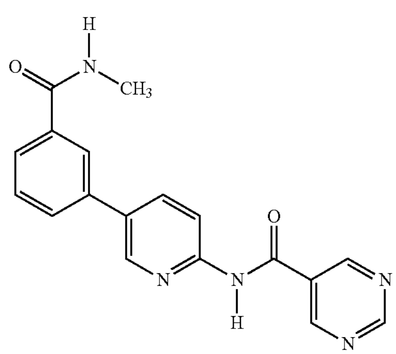 [SMILES: CNC(=O)c1cccc(-c2ccc(NC(=O)c3cncnc3)nc2)c1] | N-{5-[3-(methylcarbamoyl)phenyl]pyridin-2-yl}pyrimidine-5-carboxamide/ δ 9.29 (s, 1H), 9.26 (s, 2H), 9.53 (d, 1H, J = 2.0 Hz), 8.35 (d, 1H, J = 8.8 Hz), 7.99 (m, 2H), 7.71 (d, 1H, J = 7.2 Hz), 7.64 (d, 1H, J = 7.6 Hz), 7.47 (t, 1H, J = 7.8 Hz), 2.94 (s, 3H) |

TABLE I-continued

| Compound ID | Structure | Chemical Name/ ¹H-NMR (CDCl₃, 400 MHz) |
|---|---|---|
| 18 | 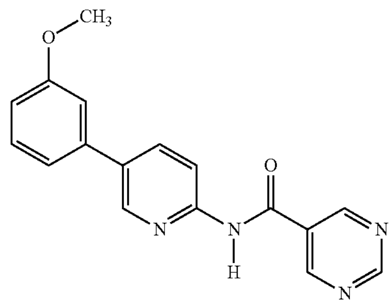 [SMILES: COc1cccc(-c2ccc(NC(=O)c3cncnc3)nc2)c1] | N-[5-(3-methoxyphenyl)pyridin-2-yl]pyrimidine-5-carboxamide/ δ 9.35 (s, 1H), 9.28 (s, 2H), 9.50 (d, 1H, J = 1.6 Hz), 8.37 (d, 1H, J = 8.8 Hz), 7.96 (dd, 1H, J = 8.8, 2.4 Hz), 7.35 (t, 1H, J = 8.0 Hz), 7.12 (d, 1H, J = 7.6 Hz), 7.05 (t, 1H, J = 2.2 Hz), 6.90 (dd, 1H, J = 8.0, 1.6 Hz), 3.93 (s, 3H) |
| 19 | 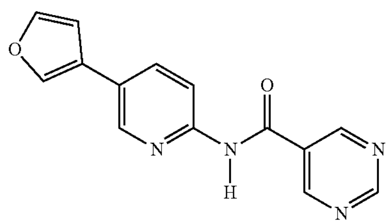 [SMILES: O=C(Nc1ccc(-c2ccoc2)cn1)c1cncnc1] | N-[5-(furan-3-yl)pyridin-2-yl]pyrimidine-5-carboxamide/ δ 9.34 (s, 1H), 9.31 (s, 2H), 8.98 (bs, 1H), 8.44 (d, 1H, J = 1.6 Hz), 8.40 (d, 1H, J = 8.8 Hz), 7.92 (dd, 1H, J = 8.8, 2.4 Hz), 7.77 (s, 1H), 7.50 (s, 1H), 6.68 (s, 1H) |
| 20 | 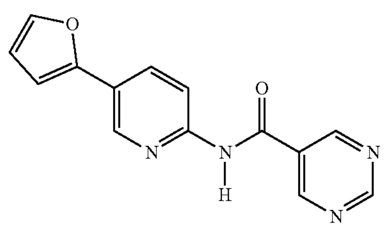 [SMILES: O=C(Nc1ccc(-c2ccco2)cn1)c1cncnc1] | N-[5-(furan-2-yl)pyridin-2-yl]pyrimidine-5-carboxamide/ δ 9.32 (s, 1H), 9.28 (s, 2H), 8.59 (d, 1H, = 2.4 Hz), 8.36 (d, 1H, J = 8.8 Hz), 8.01 (dd, 1H, J = 8.8, 2.8 Hz), 7.47 (d, 1H, J = 1.6 Hz), 6.68 (d, 1H, J = 3.2 Hz), 6.47 (dd, 1H, J = 3.2, 1.6 Hz) |
| 21 | 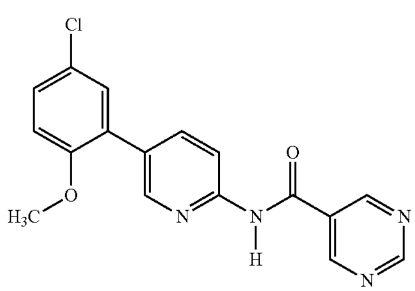 [SMILES: COc1ccc(Cl)cc1-c1ccc(NC(=O)c2cncnc2)nc1] | N-[5-(5-chloro-2-methoxyphenyl)pyridin-2-yl]pyrimidine-5-carboxamide/ND |
| 22 | 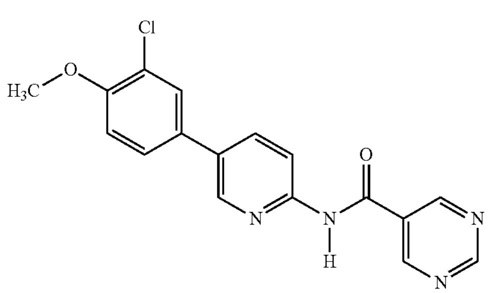 [SMILES: COc1ccc(-c2ccc(NC(=O)c3cncnc3)nc2)cc1Cl] | N-[5-(3-chloro-4-methoxyphenyl)pyridin-2-yl]pyrimidine-5-carboxamide/ND |

TABLE I-continued

| Compound ID | Structure | Chemical Name/ ¹H-NMR (CDCl₃, 400 MHz) |
| --- | --- | --- |
| 23 | 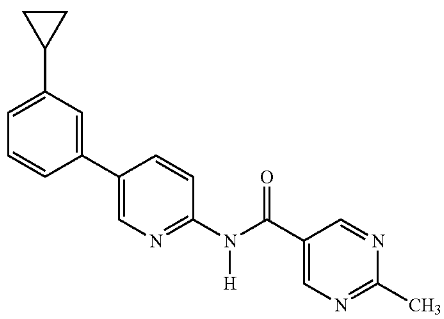 | N-[5-(3-cyclopropylphenyl)pyridin-2-yl]-2-methylpyrimidine-5-carboxamide/δ 9.21 (s, 2H), 9.12 (bs, 1H), 8.50 (d, 1H, J = 2.0 Hz), 8.46 (d, 1H, J = 8.4 Hz), 8.03 (dd, 1H, J = 8.6, 2.2 Hz), 7.38-7.32 (m, 2H), 7.27 (m, 1H), 7.08 (m, 1H), 2.83 (s, 3H), 1.96 (qui, 1H, J = 4.2 Hz), 1.02 (m, 2H), 0.75 (m, 2H) |
| 24 | 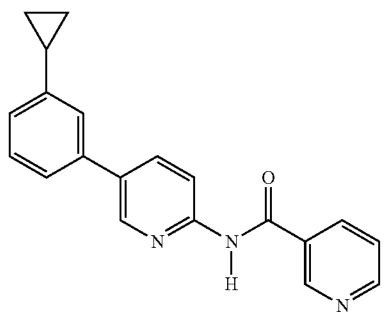 [SMILES: O=C(Nc1ccc(-c2cccc(C3CC3)c2)cn1)c1cccnc1] | N-[5-(3-cyclopropylphenyl)pyridin-2-yl]pyridine-3-carboxamide/δ 9.14 (s, 1H), 8.72 (m, 1H), 8.47 (d, 1H, J = 2.0 Hz), 8.35 (d, 1H, J = 8.4 Hz), 8.30 (dt, 1H, J = 6.4, 2.0 Hz), 7.96 (dd, 1H, J = 8.8, 2.0 Hz), 7.27 (m, 1H), 7.48 (dd, 1H, J = 8.0, 4.8 Hz), 7.30 (m, 1H), 7.02 (m, 1H), 1.92 (qui, 1H, J = 4.2 Hz), 0.97 (m, 2H), 0.71 (m, 2H) |
| 25 | 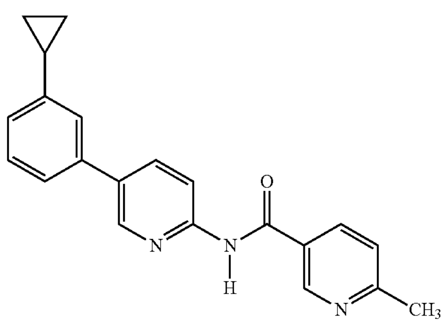 [SMILES: Cc1ccc(C(=O)Nc2ccc(-c3cccc(C4CC4)c3)cn2)cn1] | N-[5-(3-cyclopropylphenyl)pyridin-2-yl]-6-methylpyridine-3-carboxamide/δ 9.06 (d, 1H, J = 2.0 Hz), 8.86 (bs, 1H), 8.49 (d, 1H, J = 2.0 Hz), 8.44 (d, 1H, J = 8.8 Hz), 8.16 (dd, 1H, J = 8.2, 2.2 Hz), 7.98 (dd, 1H, J = 8.8, 2.4 Hz), 7.37-7.27 (m, 4H), 7.07 (dt, 1H, J = 6.8, 2.2 Hz), 2.64 (s, 1H), 1.96 (qui, 1H, J = 4.2 Hz), 1.01 (m, 2H), 0.75 (m, 2H) |
| 26 | 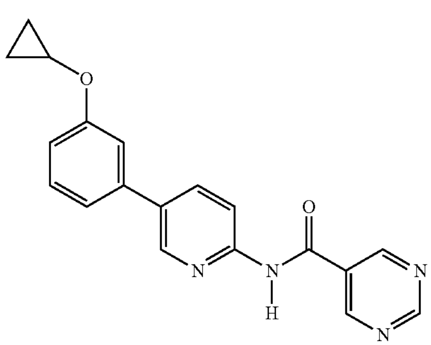 [SMILES: O=C(Nc1ccc(-c2cccc(OC3CC3)c2)cn1)c1cncnc1] | N-{5-[3-(cyclopropyloxy)phenyl]pyridin-2-yl}pyrimidine-5-carboxamide/ δ 9.40 (s, 1H), 9.34 (s, 2H), 8.52 (d, 1H, J = 2.0 Hz), 8.50 (d, 1H, J = 8.8 Hz), 8.07 (dd, 1H, J = 8.8, 2.4 Hz), 7.40 (t, 1H, J = 7.8 Hz), 7.21 (m, 1H), 7.16 (m, 1H), 7.12 (dd, 1H, J = 8.2, 1.8 Hz), 3.79 (qui, 1H, J = 2.8 Hz), 0.81 (m, 4H) |

TABLE I-continued

| Compound ID | Structure | Chemical Name/ ¹H-NMR (CDCl₃, 400 MHz) |
|---|---|---|
| 27 | 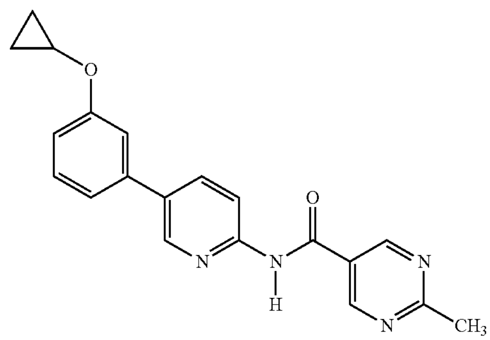 [SMILES: Cc1ncc(C(=O)Nc2ccc(-c3cccc(OC4CC4)c3)cn2)cn1] | N-{5-[3-(cyclopropyloxy)phenyl]pyridin-2-yl}-2-methylpyrimidine-5-carboxamide/δ 9.16 (s, 2H), 8.48 (d, 1H, J = 2.4 Hz), 8.31 (d, 1H, J = 8.8 Hz), 7.97 (dd, 1H, J = 8.8, 2.0 Hz), 7.34 (t, 1H, J = 7.8 Hz), 7.17 (m, 1H), 7.12 (m, 1H), 7.05 (dd, 1H, J = 8.2, 2.6 Hz), 3.79 (qui, 1H, J = 2.8 Hz), 2.78 (s, 3H), 0.76 (m, 4H) |
| 28 | 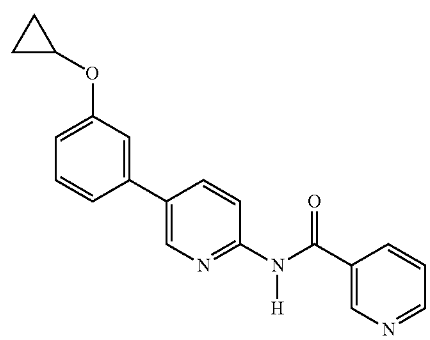 [SMILES: O=C(Nc1ccc(-c2cccc(OC3CC3)c2)cn1)c1cccnc1] | N-{5-[3-(cyclopropyloxy)phenyl]pyridin-2-yl}pyridine-3-carboxamide/ δ 9.11 (s, 1H), 8.70 (m, 1H), 8.47 (d, 1H, J = 1.2 Hz), 8.35 (m, 1H), 8.27 (d, 1H, J = 8.8 Hz), 8.00 (dd, 1H, J = 8.6, 2.2 Hz), 7.52 (dd, 1H, J = 7.8, 5.4 Hz), 7.32 (t, 1H, J = 8.0 Hz), 7.16 (m, 1H), 7.11 (m, 1H), 7.04 (m, 1H), 3.73 (qui, 1H, J = 2.8 Hz), 0.74 (m, 4H) |
| 29 | 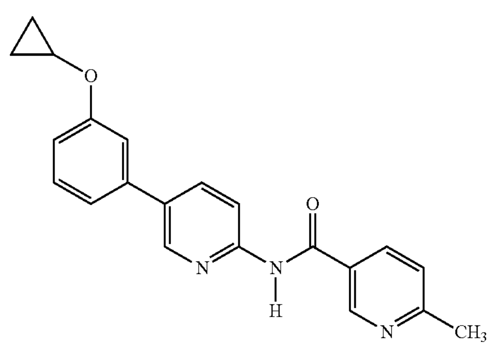 [SMILES: Cc1ccc(C(=O)Nc2ccc(-c3cccc(OC4CC4)c3)cn2)cn1] | N-{5-[3-(cyclopropyloxy)phenyl]pyridin-2-yl}-6-methylpyridine-3-carboxamide/δ 9.07 (d, 1H, J = 2.0 Hz), 8.93 (bs, 1H), 8.51 (d, 1H, J = 2.4 Hz), 8.46 (d, 1H, J = 8.4 Hz), 8.18 (dd, 1H, J = 8.2, 2.2 Hz), 8.00 (dd, 1H, J = 8.8, 2.8 Hz), 7.38 (t, 1H, J = 7.8 Hz), 7.31 (d, 1H, J = 8.0 Hz), 7.21 (t, 1H, J = 1.8 Hz), 7.16 (d, 1H, J = 7.6 Hz), 7.09 (m, 1H), 3.79 (qui, 1H, J = 4.5 Hz), 2.65 (s, 3H), 0.81 (m, 4H) |
| 30 | 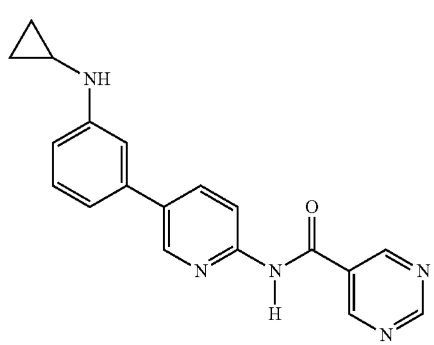 [SMILES: O=C(Nc1ccc(-c2cccc(NC3CC3)c2)cn1)c1cncnc1] | N-{5-[3-(cyclopropylamino)phenyl]pyridin-2-yl}pyrimidine-5-carboxamide/ δ 9.32 (s, 1H), 9.29 (s, 2H), 8.49 (m, 1H), 8.37 (d, 1H, J = 8.8 Hz), 7.97 (dd, 1H, J = 8.4, 2.0 Hz), 7.24 (m, 1H), 6.92 (s, 1H), 6.88 (d, 1H, J = 7.2 Hz), 6.79 (m, 1H), 2.42 (qui, 1H, J = 3.2 Hz), 0.72 (m, 2H), 0.50 (m, 2H) |

TABLE I-continued

| Compound ID | Structure | Chemical Name/ ¹H-NMR (CDCl₃, 400 MHz) |
|---|---|---|
| 31 | 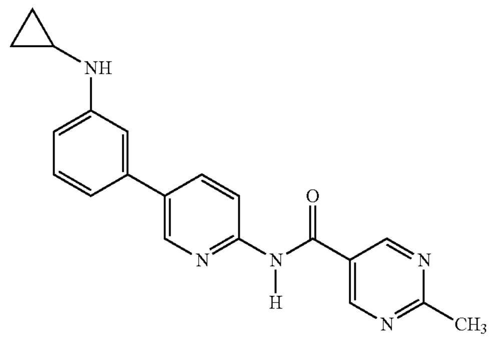 | N-{5-[3-(cyclopropylamino)phenyl]pyridin-2-yl}-2-methylpyrimidine-5-carboxamide/δ 9.18 (s, 2H), 8.47 (m, 1H), 8.35 (d, 1H, J = 8.4 Hz), 7.97 (dd, 1H, J = 8.8, 2.4 Hz), 7.23 (t, 1H, J = 7.6 Hz), 6.91 (m, 1H), 6.87 (d, 1H, J = 7.2 Hz), 6.78 (m, 1H), 2.79 (s, 3H), 2.41 (qui, 1H, J = 3.4 Hz), 0.71 (m, 2H), 0.50 (m, 2H) |
| 32 | 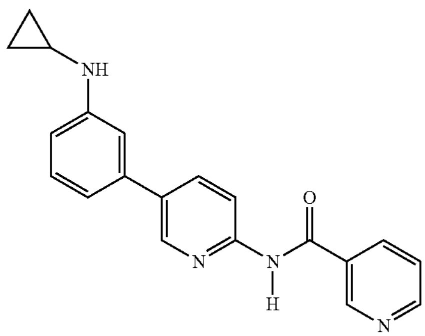 [SMILES: O=C(Nc1ccc(-c2cccc(NC3CC3)c2)cn1)c1cccnc1] | N-{5-[3-(cyclopropylamino)phenyl]pyridin-2-yl}pyridine-3-carboxamide/ δ 9.17 (s, 1H), 8.80 (d, 1H, J = 4.4 Hz), 8.77 (m, 1H), 8.52 (d, 1H, J = 2.0 Hz), 8.42 (d, 1H, J = 8.4 Hz), 8.26 (m, 1H), 7.98 (dd, 1H, J = 8.6, 2.2 Hz), 7.47 (dd, 1H, J = 8.2, 4.6 Hz), 7.27 (t, 1H, J = 7.8 Hz), 6.93 (m, 2H), 6.81 (m, 1H), 2.47 (qui, 1H, J = 3.2 Hz), 0.75 (m, 2H), 0.54 (m, 2H) |
| 33 | 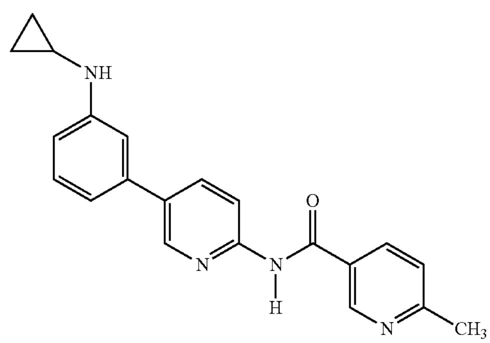 [SMILES: Cc1ccc(C(=O)Nc2ccc(-c3cccc(NC4CC4)c3)cn2)cn1] | N-{5-[3-(cyclopropylamino)phenyl]pyridin-2-yl}-6-methylpyridine-3-carboxamide/δ 9.06 (s, 1H), 8.84 (m, 1H), 8.47 (m, 1H), 8.41 (d, 1H, J = 8.8 Hz), 8.14 (d, 1H, J = 7.2 Hz), 7.95 (m, 1H), 7.28 (t, 2H, J = 6.8 Hz), 6.92 (m, 1H), 6.79 (m, 1H), 2.63 (s, 3H), 2.47 (m, 1H), 0.76 (m, 2H), 0.54 (m, 2H) |
| 34 | 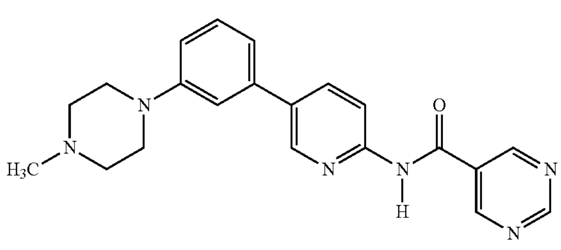 [SMILES: CN1CCN(c2cccc(-c3ccc(NC(=O)c4cncnc4)nc3)c2)CC1] | N-{5-[3-(4-methylpiperazin-1-yl)phenyl]pyridin-2-yl}pyrimidine-5-carboxamide/δ 9.39 (s, 1H), 9.27 (s, 2H), 8.68 (bs, 1H), 8.51 (d, 1H, J = 2.0 Hz), 8.38 (d, 1H, J = 8.4 Hz), 7.97 (dd, 1H, J = 8.6, 2.2 Hz), 7.36 (t, 1H, J = 8.2 Hz), 7.07 (m, 1H), 7.04 (d, 1H, J = 7.6 Hz), 6.96 (dd, 1H, J = 8.0, 2.0 Hz), 3.31 (m, 4H), 2.64 (m, 4H), 2.39 (s, 3H) |
| 35 | 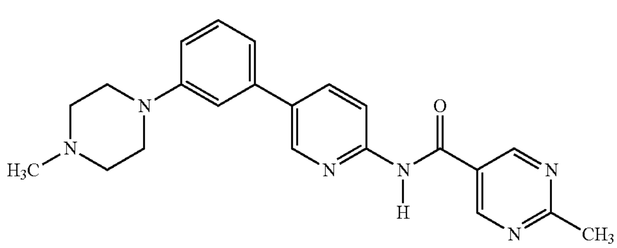 | N-{5-[3-(4-methylpiperazin-1-yl)phenyl]pyridin-2-yl}-2-methylpyrimidine-5-carboxamide/ δ 9.15 (s, 2H), 8.45 (d, 1H, J = 1.6 Hz), 8.32 (d, 1H, J = 8.8 Hz), 7.91 (dd, 1H, J = 8.0, 2.2 Hz), 7.33 (t, 1H, J = 8.0 Hz), 7.11 (d, 1H, J = 7.2 Hz), 7.04 (m, 1H), 6.91 (m, 1H), 3.20 (m, 4H), 3.18 (m, 4H), 2.84 (s, 3H), 2.76 (s, 3H) |

TABLE I-continued

| Compound ID | Structure | Chemical Name/ ¹H-NMR (CDCl₃, 400 MHz) |
|---|---|---|
| 36 | 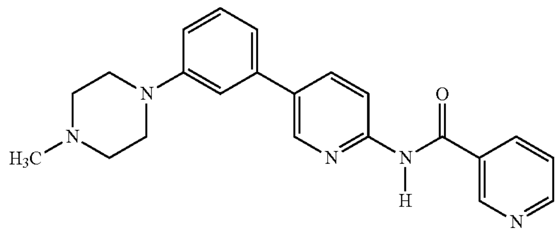 [SMILES: CN1CCN(c2cccc(-c3ccc(NC(=O)c4cccnc4)nc3)c2)CC1] | N-{5-[3-(4-methylpiperazin-1-yl)phenyl]pyridin-2-yl}pyridine-3-carboxamide/δ 9.17 (d, 1H, J = 1.2 Hz), 8.80 (dd, 1H, J = 4.4, 1.2 Hz), 8.64 (bs, 1H), 8.51 (d, 1H, J = 1.2 Hz), 8.41 (d, 1H, J = 8.8 Hz), 8.24 (m, 1H), 7.95 (dd, 1H, J = 8.6, 2.2 Hz), 7.46 (dd, 1H, J = 8.0, 5.2 Hz), 7.37 (t, 1H, J = 8.0 Hz), 7.09 (m, 2H), 6.95 (dd, 1H, J = 8.8, 1.6 Hz), 3.45 (m, 4H), 2.91 (m, 4H), 2.58 (s, 3H) |
| 37 | 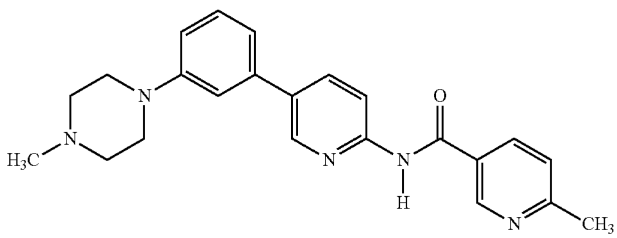 | N-{5-[3-(4-methylpiperazin-1-yl)phenyl]pyridin-2-yl}-6-methylpyridine-3-carboxamide/ δ 9.04 (s, 1H), 8.62 (s, 1H), 8.49 (d, 1H, J = 1.6 Hz), 8.40 (d, 1H, J = 8.8 Hz), 8.12 (dd, 1H, J = 8.2, 2.2 Hz), 7.95 (dd, 1H, J = 8.8, 2.4 Hz), 7.35 (t, 1H, J = 7.8 Hz), 7.29 (d, 1H, J = 8.0 Hz), 7.07 (m, 1H), 7.04 (d, 1H, J = 7.6 Hz), 6.95 (m, 1H), 3.31 (m, 4H), 2.64 (m, 7H), 2.39 (s, 3H) |
| 38 | 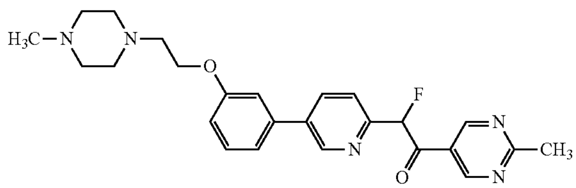 | N-{-5-[3-(2-(4-methylpiperazin-1-yl)ethoxy)phenyl]pyridin-2-yl}-2-methylpyrimidine-5-carboxamide/ δ 9.16 (s, 2H), 8.65 (bs, 1H), 8.51 (d, 1H, J = 2.0 Hz), 8.38 (d, 1H, J = 8.4 Hz), 7.96 (dd, 1H, J = 8.6, 2.2 Hz), 7.36 (t, 1H, J = 8.0 Hz), 7.14 (d, 1H, J = 7.6 Hz), 7.09 (m, 1H), 6.92 (dd, 1H, J = 8.0, 2.0 Hz), 4.16 (t, 2H, J = 5.8 Hz), 2.84 (t, 2H, J = 5.8 Hz), 2.83 (s, 3H), 2.65 (m, 4H), 2.50 (n, 4H), 2.30 (s, 3H) |
| 39 | 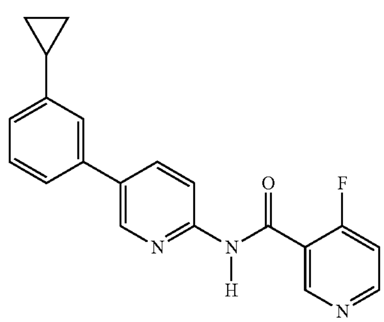 [SMILES: O=C(Nc1ccc(-c2cccc(C3CC3)c2)cn1)c1cnccc1F] | N-[5-(3-cyclopropylphenyl)pyridin-2-yl]-4-fluoropyridine-3-carboxamide/δ 9.07 (d, 1H, J = 12.0 Hz), 8.68 (d, 1H, J = 2.0 Hz), 8.64 (d, 1H, J = 4.8 Hz), 8.54 (d, 1H, J = 1.6 Hz), 8.40 (d, 1H, J = 8.4 Hz), 8.00 (t, 1H, J = 5.6 Hz), 7.96 (dd, 1H, J = 8.4, 2.0 Hz), 7.34 (m, 2H), 7.27 (m, 1H), 7.07 (m, 1H), 1.96 (qui, 1H, J = 4.5 Hz), 1.01 (m, 2H), 0.74 (m, 2H) |
| 40 | 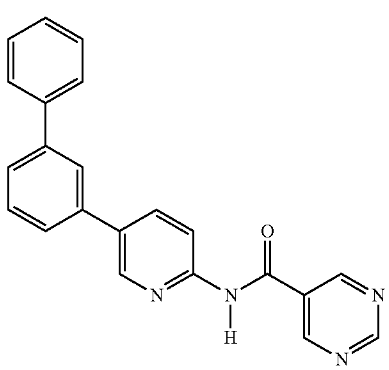 [SMILES: O=C(Nc1ccc(-c2cccc(-c3ccccc3)c2)cn1)c1cncnc1] | N-[5-(biphenyl-3-yl)pyridin-2-yl]pyrimidine-5-carboxamide/ δ 9.32 (s, 1H), 9.30 (s, 2H), 8.57 (d, 1H, J = 1.6 Hz), 8.42 (d, 1H, J = 8.4 Hz), 8.05 (dd, 1H, J = 8.6, 2.2 Hz), 7.73 (m, 1H), 7.59 (m, 3H), 7.51 (d, 2H, J = 5.2 Hz), 7.43 (t, 2H, J = 7.4 Hz), 7.34 (t, 2H, J = 7.4 Hz) |

TABLE I-continued

| Compound ID | Structure | Chemical Name/ ¹H-NMR (CDCl₃, 400 MHz) |
|---|---|---|
| 41 | 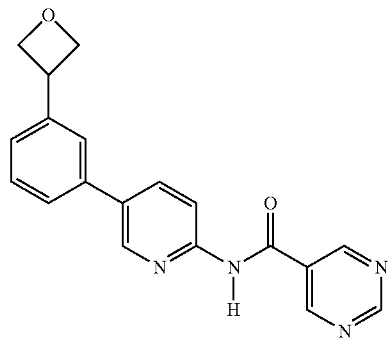 [SMILES: O=C(Nc1ccc(-c2cccc(C3COC3)c2)cn1)c1cncnc1] | N-{5-[3-(oxetan-3-yl)phenyl]pyridin-2-yl}pyrimidine-5-carboxamide/δ 11.2 (br s), 9.36 (s, 1H), 9.31 (s, 1H), 8.78 (d, 1H, J = 1.6 Hz), 8.25 (m, 2H), 7.75 (bs, 1H), 7.65 (m, 1H), 7.49 (m, 2H), 4.9 (q, 2H, J = 6.8 Hz), 4.72 (q, 2H, J = 6.8 Hz), 4.35 (qui, 1H, J = 8 Hz) |
| 42 | 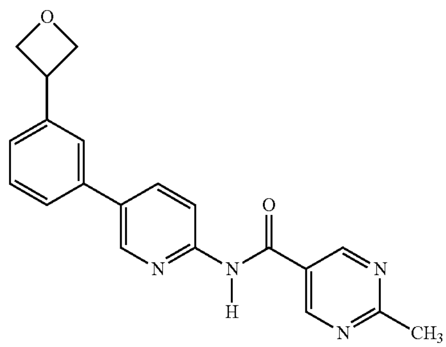 [SMILES: Cc1ncc(C(=O)Nc2ccc(-c3cccc(C4COC4)c3)cn2)cn1] | 2-methyl-N-{5-[3-(oxetan-3-yl)phenyl]pyridin-2-yl}pyrimidine-5-carboxamide/ND |
| 43 | 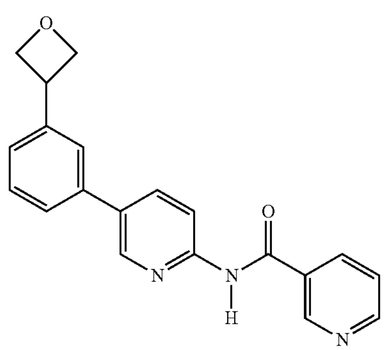 [SMILES: O=C(Nc1ccc(-c2cccc(C3COC3)c2)cn1)c1cccnc1] | N-{5-[3-(oxetan-3-yl)phenyl]pyridin-2-yl}pyridine-3-carboxamide/ND |
| 44 | 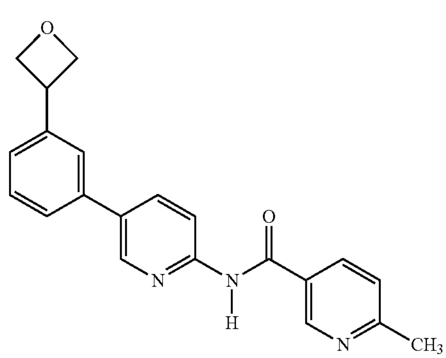 [SMILES: Cc1ccc(C(=O)Nc2ccc(-c3cccc(C4COC4)c3)cn2)cn1] | 6-methyl-N-{5-[3-(oxetan-3-yl)phenyl]pyridin-2-yl}pyridine-3-carboxamide/ND |

TABLE I-continued

| Compound ID | Structure | Chemical Name/ $^1$H-NMR (CDCl$_3$, 400 MHz) |
|---|---|---|
| 45 | 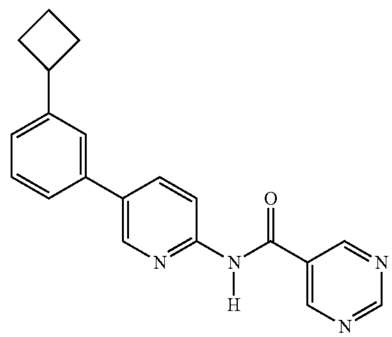 [SMILES: O=C(Nc1ccc(-c2cccc(C3CCC3)c2)cn1)c1cncnc1] | N-[5-(3-cyclobutylphenyl)pyridin-2-yl]pyrimidine-5-carboxamide/ δ 9.36 (s, 1H), 9.30 (s, 1H), 8.72 (bd, 1H, J = 2.0 Hz), 8.23 (m, 2H), 7.55 (m, 2H), 7.46 (t, J = 8 Hz), 7.30 (d, J = 7.6 Hz), 3.61 (qui, 1H, J = 8.8 Hz), 2.32 (m, 2H), 2.18 (m, 2H), 2.03 (m, 1H), 1.85 (m, 1H) |
| 46 | 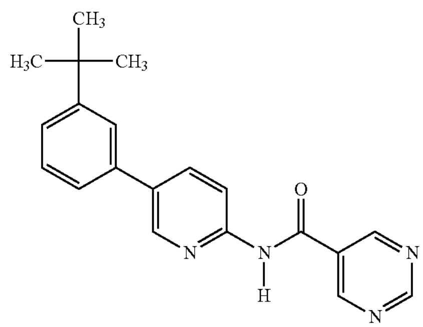 [SMILES: CC(C)(C)c1cccc(-c2ccc(NC(=O)c3cncnc3)nc2)c1] | N-[5-(3-tert-butylphenyl)pyridin-2-yl]pyrimidine-5-carboxamide/ δ 11.4 (bs, 1H) 9.36 (s, 1H), 9.31 (s, 1H), 8.72 (bd, 1H, J = 2.0 Hz), 8.28 (m, 1H), 8.20 (m, 1H), 7.71 (bs, 1H), 7.53 (m, 1H), 7.44 (m, 2H), 1.37 (s, 9H) |
| 47 | 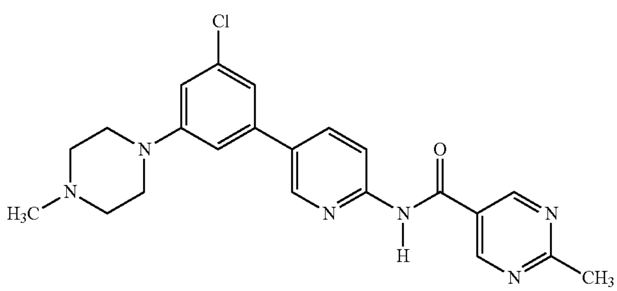 | N-{5-[3-chloro-5-(4-methylpiperazin-1-yl)phenyl]pyridin-2-yl}-2-methylpyrimidine-5-carboxamide/ ND |
| 48 | 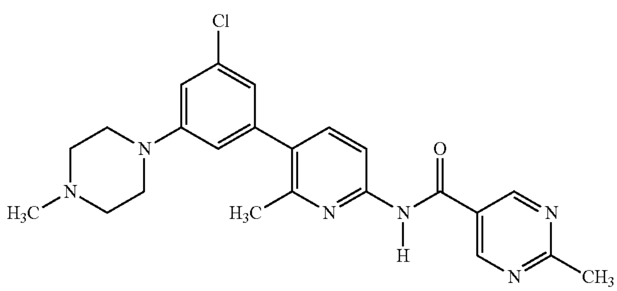 | N-{5-[3-chloro-5-(4-methylpiperazin-1-yl)phenyl]-6-methylpyridin-2-yl}-2-methylpyrimidine-5-carboxamide/ ND |

TABLE I-continued

| Compound ID | Structure | Chemical Name/ ¹H-NMR (CDCl₃, 400 MHz) |
|---|---|---|
| 49 | 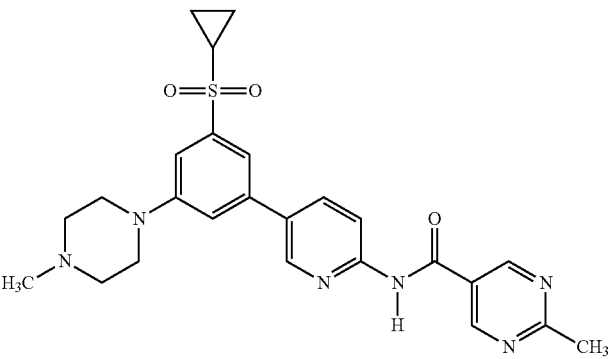 | N-{5-[3-cyclopropylsulfonyl-5-(4-methylpiperazin-1-yl)phenyl]pyridin-2-yl}-2-methylpyrimidine-5-carboxamide/ δ 11.39 (s, 1H), 9.22 (s, 1H), 8.81 (s, 1H), 8.29 (m, 2H), 7.54 (d, 2H, J = 9.6 Hz), 7.33 (s, 1H), 3.32 (m, 4H), 3.00 (m, 1H), 2.71 (s, 3H), 2.50 (bs, 4H), 2.24 (s, 3H), 1.17 (m, 2H), 1.04 (m, 2H) |
| 50 | 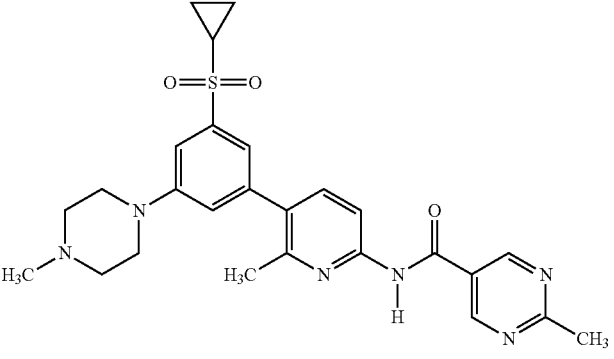 | N-{5-[3-cyclopropylsulfonyl-5-(4-methylpiperazin-1-yl)phenyl]-6-methylpyridin-2-yl}-2-methylpyrimidine-5-carboxamide/ δ 11.15 (s, 1H), 9.22 (s, 2H), 8.12 (d, 1H, J = 8.4 Hz), 7.78 (d, 1H, J = 8.4 Hz), 7.34 (s, 1H), 7.27 (s, 1H), 7.22 (s, 1H), 3.33 (m, 4H), 2.92 (m, 1H), 2.73 (s, 3H), 2.55 (m, 4H), 2.45 (s, 3H), 2.28 (s, 3H), 1.16 (m, 2H), 1.10 (m, 2H) |
| 51 | 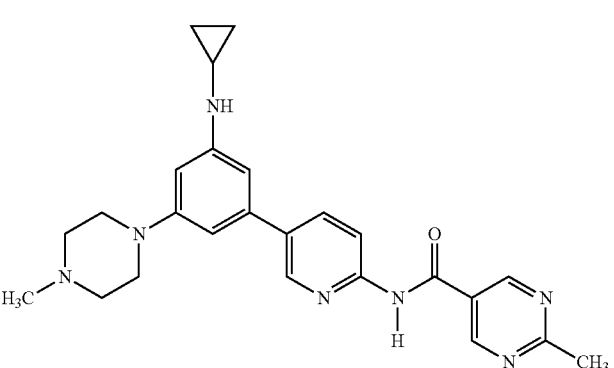 | N-{5-[3-cycopropylamino-5-(4-methylpiperazin-1-yl)phenyl]pyridin-2-yl}-2-methylpyrimidine-5-carboxamide/ δ 9.20 (s, 2H), 8.62 (d, 1H, J = 2.0 Hz), 8.22 (d, 1H, J = 8.8 Hz), 8.08 (dd, 1H, J = 8.4 Hz, J = 2.9 Hz), 6.49 (d, 2H, J = 6.0 Hz), 6.32 (s, 1H), 3.17 (m, 4H), 2.72 (s, 3H), 2.47 (m, 4H), 2.39 (m, 1H), 2.23 (s, 3H) 1.24 (s, 1H), 0.71 (m, 2H), 0.39 (m, 2H) |
| 52 | 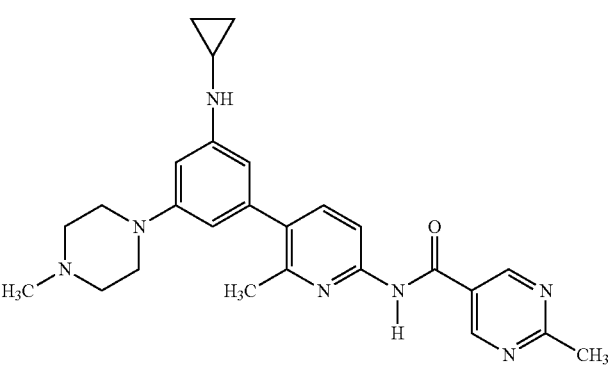 | N-{5-[3-cyclopropylamino-5-(4-methylpiperazin-1-yl)phenyl]-6-methylpyridin-2-yl}-2-methylpyrimidine-5-carboxamide/ δ 9.21 (s. 2H), 8.04 (d, 1H, J = 8.4 Hz), 7.63 (d, 1H, J = 8.4 Hz), 6.27 (s, 1H), 6.16 (s, 2H), 6.02 (s, 1H), 3.17 (bs, 1H), 3.10 (bs 4H), 2.71 (s, 3H), 2.44 (bs, 7H), 2.21 (bs, 3H), 1.23 (s, 1H), 0.67 (m, 2H), 0.37 (m,2H). |

TABLE I-continued

| Compound ID | Structure | Chemical Name/ ¹H-NMR (CDCl₃, 400 MHz) |
|---|---|---|
| 53 | 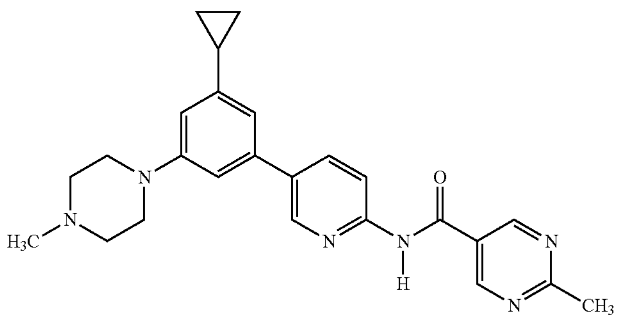 | N-{5-[3-cyclopropyl-5-(4-methylpiperazin-1-yl)phenyl]-6-methylpyridin-2-yl}-2-methylpyrimidine-5-carboxamide/ 11.31 (s, 1H), 9.22 (s, 2H), 8.70 (s, 1H), 8.43 (bs, 3H), 8.24 (d, 1H, J = 8.8 Hz), 8.15 (dd, 1H, J = 8.8 Hz, J = 2.4 Hz), 7.0 (s, 1H), 6.81 (s, 1H), 6.68 (s, 1H) 3.21 (m, 4H), 2.71 (s, 3H), 2.48 (m, 4H), 2.23 (s, 3H) 1.93 (m, 1H), 0.93 (m, 2H), 0.76 (m, 2H) |
| 54 | 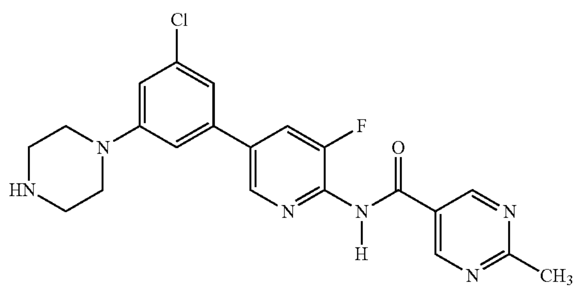 [SMILES: Cc1ncc(C(=O)Nc2ncc(-c3cc(Cl)cc(N4CCNCC4)c3)cc2F)cn1] | N-{5-[3-chloro-5-(piperazin-1-yl)phenyl]-3-Fluoropyridin-2-yl}-2-methylpyrimidine-5-carboxamide/ δ 9.22 (s, 2H), 8.70 (s, 1H), 8.27 (d, 1H, J = 11.6 Hz), 7.24 (m, 2H), 6.99 (s, 1H), 3.23 (bs, 4H), 2.85 (bs, 4H), 2.75 (s, 3H) |
| 55 | 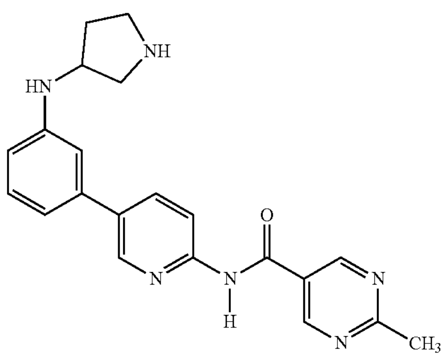 [SMILES: Cc1ncc(C(=O)Nc2ccc(-c3cccc(NC4CCNC4)c3)cn2)cn1] | 2-methyl-N-{5-[3-(pyrrolidin-3-ylamino)phenyl]pyridin-2-yl}pyrimidine-5-carboxamide/ δ 11.41 (s, 1H), 9.31 (bs, 1H), 9.24 (s, 1H), 8.68 (d, 1H, J = 2.4 Hz), 8.27 (d, 1H, J = 8.8 Hz), 8.16 (dd, 1H, J = 8.8 Hz, J = 2.2 Hz), 7.26 (t, 1H, J = 8.0 Hz), 6.99 (d, 1H, J = 8.0 Hz), 6.94 (s, 1H), 6.69 (d, 1H, J = 8.0 Hz), 4.23 (m, 1H), 3.45 (m, 1H), 3.34 (m, 1H), 3.30 (m, 1H), 3.08 (m, 1H), 2.72 (s, 3H), 2.25 (m, 1H), 1.92 (m, 1H) |
| 56 | 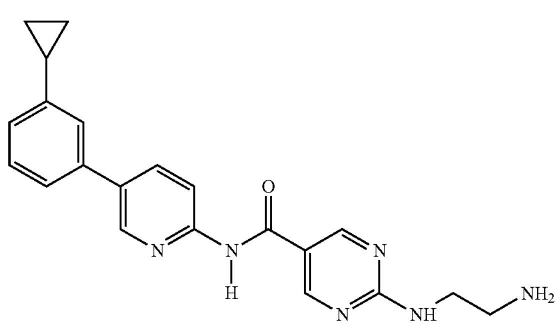 [SMILES: NCCNc1ncc(C(=O)Nc2ccc(-c3cccc(C4CC4)c3)cn2)cn1] | 2-[(2-aminoethyl)amino]-N-[5-(3-cyclopropylphenyl)pyridin-2-yl]pyrimidine-5-carboxamide/ δ 8.68 (dd, 2H, J = 21.0 Hz, J = 2.0 Hz), 8.22 (d, 1H, J = 8.8 Hz), 8.12 (dd, 1H, J = 8.8 Hz, J = 2.4 Hz), 8.03 (dd, 1H, J = 8.8 Hz, J = 2.4 Hz), 7.47 (d, 1H, J = 7.6), 7.35 (m, 2H), 7.09 (d, 1H, J = 7.2 Hz), 3.47 (m, 2H), 2.88 (m, 2H), 2.02 (m, 1H), 1.8 (bs, 4H), 1.00 (m, 2H), 0.77 (m, 2H) |

TABLE I-continued

| Compound ID | Structure | Chemical Name/ ¹H-NMR (CDCl₃, 400 MHz) |
|---|---|---|
| 57 | 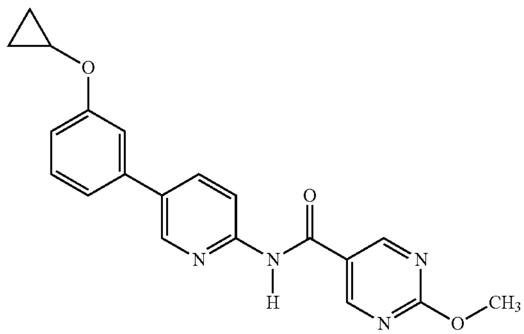 [SMILES: COc1ncc(C(=O)Nc2ccc(-c3cccc(OC4CC4)c3)cn2)cn1] | N-{5-[3-(cyclopropyloxy)phenyl]pyridin-2-yl}-2-methoxypyrimidine-5-carboxamide/δ 9.15 (s, 1H), 8.71 (d, 1H, J = 1.6 Hz), 8.25 (d, 2H, J = 8.4 Hz), 8.18 (dd, 1H, J = 8.8 Hz, J = 2.4 Hz), 7.45 (t, 1H, J = 8.0 Hz), 7.36 (m, 2H), 7.12 (dd, 1H, J = 8.4 Hz, J = 2.0 Hz), 4.02 (s, 3H), 3.95 (m, 1H), 0.83 (m, 2H), 0.69 (m, 2H) |
| 58 | 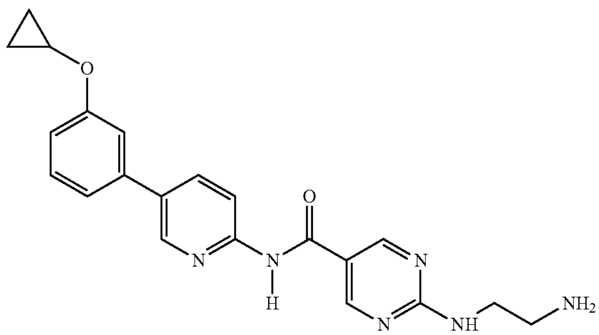 [SMILES: NCCNc1ncc(C(=O)Nc2ccc(-c3cccc(OC4CC4)c3)cn2)cn1] | 2-[(2-aminoethyl)amino]-N-[5-(3-cyclopropyloxyphenyl)pyridin-2-yl]pyrimidine-5-carboxamide/ δ 8.69 (dd, 2H, J = 19.6 Hz, J = 2.0 Hz), 8.23 (d, 1H, J = 8.8 Hz), 8.13 (dd, 1H, J = 8.8 Hz, J = 2.4 Hz), 8.03 (dd, 1H, J = 8.8 Hz, J = 1.6 Hz), 7.44 (t, 1H, J = 8.0 Hz), 7.33 (m, 2H), 7.10 (m, 1H), 6.57 (d, 1H, J = 8.8 Hz), 3.94 (m, 1H), 3.46 (m, 2H), 2.86 (m, 2H), 0.83 (m, 2H), 0.69 (m, 2H) |
| 59 | 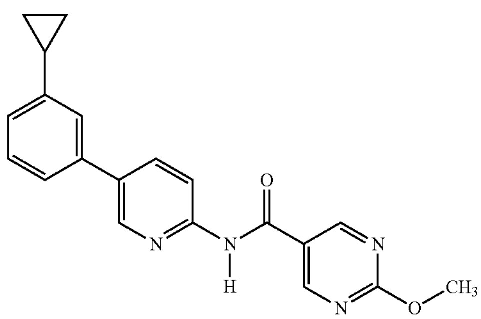 [SMILES: COc1ncc(C(=O)Nc2ccc(-c3cccc(C4CC4)c3)cn2)cn1] | N-[5-(3-cyclopropylphenyl)pyridin-2-yl]-2-methoxypyrimidine-5-carboxamide/δ 11.19, (bs, 1H), 9.17 (s, 2H), 8.72 (d, 1H, J = 2.4 Hz), 8.26 (d, 1H, J = 8.8 Hz), 8.17 (dd, 1H, J = 8.4 Hz, J = 2.4 Hz), 7.49 (d, 1H, J = 8.0 Hz), 7.43 (s, 1H), 7.36 (t, 1H, J = 7.2 Hz), 7.1 (d, 1H, J = 7.6 Hz), 4.0 (s, 3H), 2.0 (m, 1H), 0.97 (m, 1H), 0.79 (m, 1H) |
| 60 | 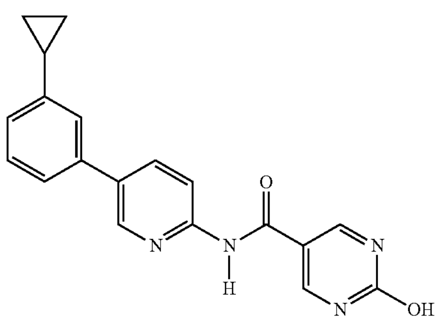 [SMILES: O=C(Nc1ccc(-c2cccc(C3CC3)c2)cn1)c1cnc(O)nc1] | N-[5-(3-cyclopropylphenyl)pyridin-2-yl]-2-hydroxypyrimidine-5-carboxamide/δ 9.89 (s, 1H), 8.69 (m, 1H), 8.58 (m, 1H), 8.37 (bs, 1H), 8.15 (m, 2H), 7.41 (m, 2H), 7.08 (m, 1H), 2.01 (m, 1H), 1.00 (m, 2H), 0.77 (m, 2H) |
| 61 | 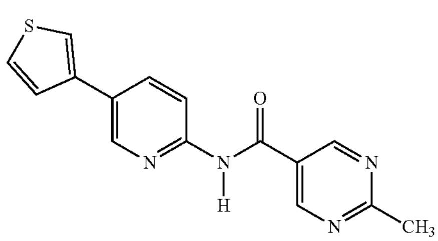 [SMILES: Cc1ncc(C(=O)Nc2ccc(-c3ccsc3)cn2)cn1] | 2-methyl-N-[5-(thiophen-3-yl)pyridin-2-yl]pyrimidine-5-carboxamide/δ 9.20 (s, 2H), 8.81 (s, 1H), 8.22 (d, 2H, J = 1.6 Hz), 7.99 (m, 1H), 7.66 (m, 2H), 2.73 (s, 3H) |

TABLE I-continued

| Compound ID | Structure | Chemical Name/ ¹H-NMR (CDCl₃, 400 MHz) |
|---|---|---|
| 62 | 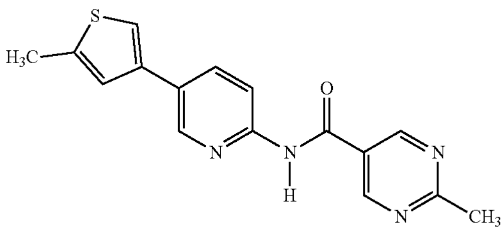 | 2-methyl-N-[5-(5-methylthiophen-3-yl)pyridin-2-yl]pyrimidine-5-carboxamide/δ 11.21 (s, 1H), 9.20 (s, 2H), 8.75 (d, 1H, J = 1.6 Hz), 8.22 (d, 1H, J = 8.8 Hz), 8.16 (dd, 1H, J = 8.8 Hz, J = 2.4 Hz), 7.73 (d, 1H, J = 1.2 Hz), 7.35 (s, 1H) 2.71 (s, 3H), 2.50 (s, 3H) |
| 63 | 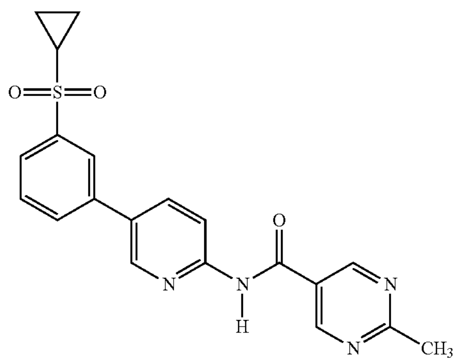 [SMILES: Cc1ncc(C(=O)Nc2ccc(-c3cccc(S(=O)(=O)C4CC4)c3)cn2)cn1] | N-{5-[3-(cyclopropylsulfonyl)phenyl]pyridin-2-yl}-2-methylpyrimidine-5-carboxamide/δ 11.42 (s, 1H), 9.23 (s, 2H), 8.85 (d, 1H, J = 1.2 Hz), 8.32 (m, 2H), 8.30 (bs, 1H), 8.14 (d, 1H, J = 8.0 Hz), 7.92 (d, 1H, J = 8.0 Hz), 7.70 (t, 1H, J = 8.0 Hz), 2.96 (q 1H, J = 3.6 Hz), 2.74 (s, 3H), 1.21 (m, 2H), 1.11 (m, 2H) |
| 64 | 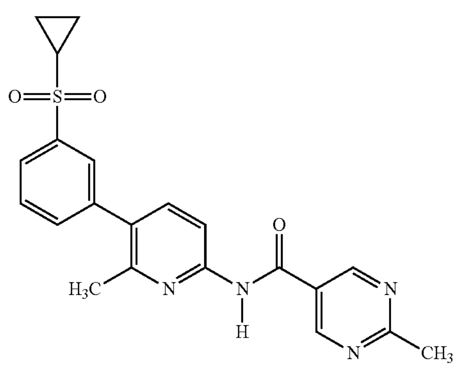 [SMILES: Cc1ncc(C(=O)Nc2ccc(-c3cccc(S(=O)(=O)C4CC4)c3)c(C)n2)cn1] | N-{5-[3-(cyclopropylsulfonyl)phenyl]-6-methylpyridin-2-yl}-2-methylpyrimidine-5-carboxamide/ δ 11.33 (bs, 1H), 9.21 (s, 2H), 8.16 (d, 1H, J = 8.1 Hz), 7.92 (m, 2H), 7.79 (m, 3H), 2.95 (m 1H), 2.71 (s, 3H), 2.46 (s, 3H), 1.17 (m, 2H), 1.07 (m, 2H) |
| 65 | 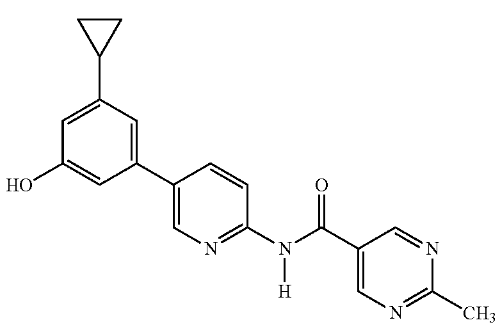 [SMILES: Cc1ncc(C(=O)Nc2ccc(-c3cc(O)cc(C4CC4)c3)cn2)cn1] | N-[5-(3-cyclopropyl-5-hydroxyphenyl)pyridin-2-yl]-2-methylpyrimidine-5-carboxamide/ δ 11.30 (s, 1H), 9.45 (s, 1H), 9.21 (s, 2H), 8.65 (d, 1H, J = 2.4 Hz) 8.25 (d, 1H, J = 2.4 Hz), 8.10 (dd, 1H, J = 8.4 Hz, J = 2.4 Hz), 6.86 (m, 2H), 6.49 (s, 1H), 2.73 (s 3H), 1.92 (m, 1H), 0.97 (m, 2H), 0.72 (m, 2H) |

TABLE I-continued

| Compound ID | Structure | Chemical Name/ ¹H-NMR (CDCl₃, 400 MHz) |
|---|---|---|
| 66 | 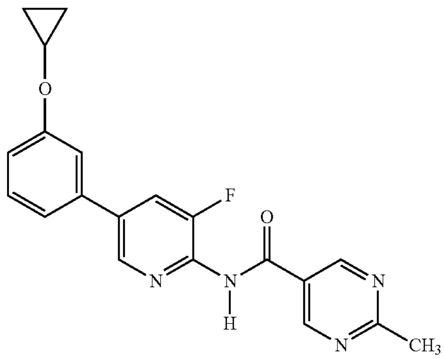 [SMILES: Cc1ncc(C(=O)Nc2ncc(-c3cccc(OC4CC4)c3)cc2F)cn1] | N-{5-[3-(cyclopropyloxy)phenyl]-3-fluoropyridin-2-yl}-2-methylpyrimidine-5-carboxamide/ δ δ 11.20 (s, 1H), 9.22 (s, 2H), 8.68 (s, 1H), 8.21 (dd, 1H, J = 11.2 Hz, J = 2.2 Hz), 7.44 (m, 3H), 7.15 (d, 1H, J = 8.4 Hz), 3.97 (q, 1H, J = 3.2 Hz), 2.75 (s, 3H), 0.85 (m, 2H), 0.69 (m, 2H) |
| 67 | 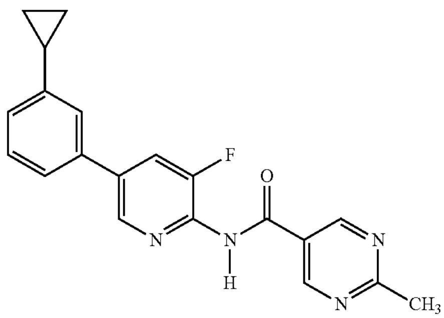 | N-[5-(3-cyclopropylphenyl)-3-fluoropyridin-2-yl]-2-methylpyrimidine-5-carboxamide/ δ 11.18 (s, 1H), 9.22 (s, 2H), 8.67 (s, 1H), 8.21 (dd, 1H, J = 11.2 Hz, J = 2.2 Hz), 7.56 (d, 1H, J = 8.0 Hz), 7.49 (s, 1H), 7.39 (t, 1H, J = 7.2 Hz), 7.16 (d, 1H, J = 8.0 Hz), 2.73 (s, 3H), 2.01 (q, 1H, J = 2.4 Hz), 1.00 (m, 2H), 0.82 (m, 2H) |
| 68 | 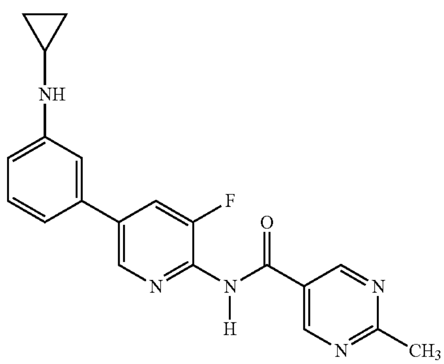 | N-{5-[3-(cyclopropylamino)phenyl]-3-fluoropyridin-2-yl}-2-methylpyrimidine-5-carboxamide/ δ 11.16 (s, 1H), 9.22 (s, 2H), 8.56 (s, 1H), 8.06 (dd, 1H, J = 11.2 Hz, J = 2.0 Hz), 7.23 (t, 1H, J = 8.0 Hz), 7.03 (s, 1H), 6.97 (d, 1H, J = 7.2 Hz), 6.78 (dd, 1H, J = 7.6 Hz, J = 1.2 Hz), 6.26 (s, 1H), 2.73 (s, 3H), 2.41 (m, 1H), 0.73 (m, 2H), 0.41 (m, 2H) |
| 69 | 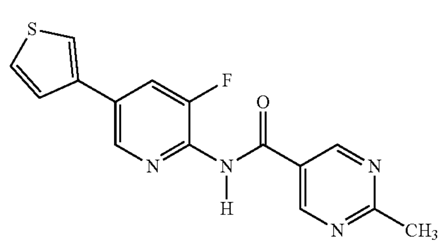 | N-[3-fluoro-5-(thiophen-3-yl)pyridin-2-yl]-2-methylpyrimidine-5-carboxamide/ δ 11.15 (s, 1H), 9.22 (s, 2H), 8.77 (s, 1H), 8.27 (dd, 1H, J = 11.2 Hz, J = 2.0 Hz), 8.18 (t, 1H, J = 2.0 Hz), 7.74 (d, 2H, J = 2.0 Hz), 2.73 (s, 3H) |

TABLE I-continued

| Compound ID | Structure | Chemical Name/ ¹H-NMR (CDCl₃, 400 MHz) |
|---|---|---|
| 70 | 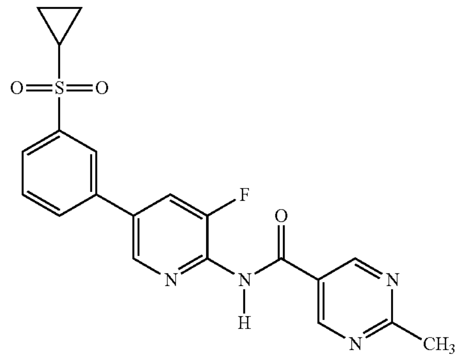 [SMILES: Cc1ncc(C(=O)Nc2ncc(-c3cccc(S(=O)(=O)C4CC4)c3)cc2F)cn1] | N-{5-[3-(cyclopropylsulfonyl)phenyl]-3-fluoropyridin-2-yl}-2-methylpyrimidine-5-carboxamide/ δ 11.28 (s, 1H), 9.23 (s, 2H), 8.79 (s, 1H), 8.37 (dd, 1H, J = 11.6 Hz, J = 2.0 Hz), 8.29 (s, 1H), 8.19 (d, 1H, J = 7.6 Hz), 7.96 (d, 1H, J = 8.0 Hz), 7.81 (t, 1H, J = 8.0 Hz), 3.02 (m, 1H), 2.74 (s, 3H), 1.20 (m, 2H), 1.08 (m, 2H) |

TABLE II

| Compound ID | Monomer Synthesis Procedure | Carboxylic acid A | General Coupling Procedure | Yield (%) | Observed Exact Mass (M + H) |
|---|---|---|---|---|---|
| 1 | NA | pyrimidine-5-carboxylic acid | 1 | 40 | 277.3 |
| 2 | NA | pyrimidine-5-carboxylic acid | 1 | 17.2 | 311.0 |
| 3 | NA | pyrimidine-5-carboxylic acid | 1 | 50 | 311.1 |
| 4 | NA | pyrimidine-5-carboxylic acid | 1 | 13.9 | 311.2 |
| 5 | NA | pyrimidine-5-carboxylic acid | 1 | 27.3 | 413.2 |
| 6 | NA | pyrimidine-5-carboxylic acid | 1 | 42.7 | 241.2 |
| 7 | NA | pyrimidine-5-carboxylic acid | 1 | 13.2 | 283.2 |
| 8 | NA | 2-methyl-pyrimidine-5-carboxylic acid | 2 | 16 | 291.0 |
| 9 | NA | 2-methyl-pyrimidine-5-carboxylic acid | 1 | 8.4 | 306.0 |
| 10 | NA | pyrimidine-3-carboxylic acid | 1 | 58 | 276.0 |
| 11 | NA | pyrimidine-3-carboxylic acid | 1 | 18 | 281.9 |
| 12 | G | pyrimidine-5-carboxylic acid | 1 | 50 | 277.9 |
| 13 | NA | pyrimidine-5-carboxylic acid | 1 | 63 | 277.1 |
| 14 | NA | pyrimidine-5-carboxylic acid | 1 | 19 | 277.1 |
| 15 | NA | pyrimidine-5-carboxylic acid | 1 | 18 | 277.1 |
| 16 | A | pyrimidine-5-carboxylic acid | 2 | 9.7 | 317.0 |
| 17 | NA | pyrimidine-5-carboxylic acid | 2 | 15 | 334.0 |
| 18 | NA | pyrimidine-5-carboxylic acid | 2 | 18 | 307.0 |
| 19 | NA | pyrimidine-5-carboxylic acid | 1 | 16 | 266.9 |
| 20 | NA | pyrimidine-5-carboxylic acid | 1 | 28 | 267.0 |
| 21 | K | pyrimidine-5-carboxylic acid | 1 | 8.4 | 340.9 |
| 22 | L | pyrimidine-5-carboxylic acid | 1 | 58 | 340.9 |
| 23 | A | 2-methyl-pyrimidine-5-carboxylic acid | 2 | 25.4 | 331.0 |
| 24 | A | pyrimidine-3-carboxylic acid | 2 | 26.6 | 316.0 |
| 25 | A | 6-methyl-pyridine-3-carboxylic acid | 2 | 28.8 | 330.0 |
| 26 | B | pyrimidine-5-carboxylic acid | 2 | 31.5 | 333.0 |
| 27 | B | 2-methyl-pyrimidine-5-carboxylic acid | 2 | 32.6 | 347.0 |
| 28 | B | pyridine-3-carboxylic acid | 2 | 30.8 | 332.0 |
| 29 | B | 6-methyl-pyridine-3-carboxylic acid | 2 | 29.6 | 346.0 |
| 30 | C | pyrimidine-5-carboxylic acid | 2 | 27.2 | 332.0 |
| 31 | C | 2-methyl-pyrimidine-5-carboxylic acid | 2 | 13 | 346.0 |
| 32 | C | pyridine-3-carboxylic acid | 2 | 13.6 | 331.0 |
| 33 | C | 6-methyl-pyridine-3-carboxylic acid | 2 | 23 | 345.0 |
| 34 | D | pyrimidine-5-carboxylic acid | 3 | 17.9 | 375.0 |
| 35 | D | 2-methyl-pyrimidine-5-carboxylic acid | 3 | 20.7 | 389.0 |
| 36 | D | pyridine-3-carboxylic acid | 3 | 32.3 | 374.0 |
| 37 | D | 6-methyl-pyridine-3-carboxylic acid | 3 | 27.7 | 388.0 |
| 38 | E | 2-methyl-pyrimidine-5-carboxylic acid | 2 | 31 | 433.0 |
| 39 | A | 4-fluoropyridine-3-carboxylic acid | 2 | 25.3 | 334.0 |
| 40 | F | pyrimidine-5-carboxylic acid | 2 | 34.4 | 353.0 |
| 41 | H | pyrimidine-5-carboxylic acid | 4 | 27.2 | 333.0 |
| 42 | H | 2-methyl-pyrimidine-5-carboxylic acid | 4 | 26.1 | 347.0 |
| 43 | H | pyridine-3-carboxylic acid | 4 | 17.1 | 332.0 |

TABLE II-continued

| Compound ID | Monomer Synthesis Procedure | Carboxylic acid A | General Coupling Procedure | Yield (%) | Observed Exact Mass (M + H) |
|---|---|---|---|---|---|
| 44 | H | 6-methyl-pyridine-3-carboxylic acid | 4 | 21.9 | 346.0 |
| 45 | I | pyrimidine-5-carboxylic acid | 2 | 20.4 | 331.0 |
| 46 | J | pyrimidine-5-carboxylic acid | 2 | 20.4 | 333.0 |
| 47 | M | 2-methyl-pyrimidine-5-carboxylic acid | 5 | 27.2 | 423.36 |
| 48 | N | 2-methyl-pyrimidine-5-carboxylic acid | 5 | 4.3 | 437.26 |
| 49 | O | 2-methyl-pyrimidine-5-carboxylic acid | 5 | 9.5 | 493.3 |
| 50 | P | 2-methyl-pyrimidine-5-carboxylic acid | 5 | 13 | 507.5 |
| 51 | NA | NA | NA | NA | 444.34 |
| 52 | NA | NA | NA | NA | 458.34 |
| 53 | NA | NA | NA | NA | 429.5 |
| 54 | NA | NA | NA | NA | 425.08 |
| 55 | NA | NA | NA | NA | 375.5 |
| 56 | NA | NA | NA | NA | 374.13 |
| 57 | B | 2-methoxy-pyrimidine-5-carboxylic acid | 5 | 12.5 | 363.08 |
| 58 | NA | NA | NA | NA | 390.11 |
| 59 | A | 2-methoxy-pyrimidine-5-carboxylic acid | 5 | 4.8 | 347.14 |
| 60 | NA | NA | NA | NA | 331.05 |
| 61 | Q | 2-methyl-pyrimidine-5-carboxylic acid | 2 | 38.9 | 297.2 |
| 62 | R | 2-methyl-pyrimidine-5-carboxylic acid | 2 | 14 | 311.2 |
| 63 | S | 2-methyl-pyrimidine-5-carboxylic acid | 5 | 34.7 | 395.24 |
| 64 | T | 2-methyl-pyrimidine-5-carboxylic acid | 5 | 32 | 409.13 |
| 65 | NA | NA | NA | NA | 347.2 |
| 66 | U | 2-methyl-pyrimidine-5-carboxylic acid | 5 | 26.5 | 365.21 |
| 67 | V | 2-methyl-pyrimidine-5-carboxylic acid | 5 | 21.8 | 349.24 |
| 68 | NA | NA | NA | NA | 356.2 |
| 69 | W | 2-methyl-pyrimidine-5-carboxylic acid | 5 | 13.1 | 315.2 |
| 70 | X | 2-methyl-pyrimidine-5-carboxylic acid | 5 | 32.7 | 413.19 |

Tubulin Polymerization Assay

The Tubulin Polymerization Assay uses porcine neuronal tubulin and measurements are based on fluorescence enhancement due to the incorporation of a fluorescent reporter into microtubules as polymerization occurs. The assay generates a polymerization curve representing the three phases of microtubule formation (nucleation, growth and equilibrium). $IC_{50}$ values for tested compounds can be generated from the observed polymerization curves.

Procedure: All compounds dilutions (in DMSO) were prepared prior to the following steps. A Molecular Devices M2 plate reader was set to 37° C. Once the internal temperature of the plate reader reached 37° C. a 96 well plate (Corning Costar, at. #3686) was placed in the fluorimeter and allowed to warm to 37° C. for 30 minutes. A total of 10 mg of porcine tubulin was resuspended in 8 mL of Polymerization Buffer [Buffer 1 (80 mM PIPES pH 6.9, 2.0 mM MgCl2, 0.5 mM EGTA, 1.0 mM GTP and 10 µM fluorescent reporter) supplemented with 20% glycerol] to generate a 2.0 mg/ml tubulin stock and this was kept on ice. The 50×compound stocks in 100% DMSO were spotted 1 µl/well in duplicate into the wells of the 96-well plate at 37° C. and allowed to re-warm for 5 minutes at 37° C. During this incubation the 2.0 mg/ml tubulin stock was placed in a disposable plastic trough and allowed to warm briefly at room temperature. To initiate the reaction, 50 µl/well of 2.0 mg/ml tubulin in Polymerization Buffer was added to each well using a multi-channel pipettor and the fluorescence measurements were started immediately.

Data analysis: The fluorescence data acquired for tested compounds was analyzed as follows. The maximal velocity ($V_{max}$) of tubulin polymerization was determined using linear regression of the averaged fluorescence data at each time point using GraphPad Prism 5.0 software. The $V_{max}$ determinations for each compound at each concentration were then normalized to reactions that contained DMSO (2% final concentration) but no test compounds. This converted the data to % Activity, which refers to the percent of the $V_{max}$ of an uninhibited reaction. The concentration response curves were then plotted as the % Activity versus the Log 10 of the compound concentration in micromolar and fit by non-linear regression to a 4-parameter sigmoidal dose-response equation using GraphPad Prism 5.0 software to determine the IC50 for each compound.

Results from selected compounds tested are shown in Table III and correspond to compounds identified in Tables I and II as well as two comparative compounds, namely vinblastine and vincristine.

TABLE III

| Compound | $IC_{50}$ (µM) |
|---|---|
| 1 | 1.4 |
| 3 | 1.45 |
| 16 | 0.48 |
| 23 | 0.89 |
| 27 | 0.68 |
| 31 | 0.32 |
| 44 | 0.30 |
| 61 | 0.26 |
| 63 | 0.24 |
| 64 | 0.12 |
| 66 | 3.84 |
| 67 | 2.42 |
| 68 | 1.98 |
| 69 | 2.35 |
| 70 | 0.01 |
| Vinblastine | 0.2 |
| Vincristine | 0.68 |

Cell Viability Assay Protocol

Cells were trypsinized, counted, and re-seeded into a 384-well tissue culture plate at 1000 cells per well in 25 mL media. Cells were incubated at 37° C. in an atmosphere of 5% $CO_2$ for 24 hours. Experimental compounds, initially dissolved in DMSO and diluted further in media were added to the wells and incubated for 72 hours. Cell viability was measured using the ATPlite 1 step Luminescence Detection Assay system (Perkin Elmer) as described in the Assay kit instructions. Results with selected compounds are shown in Table IV.

Cell Culture Lines and Media: (1) A2780 cells were cultured in RPMI media with 10% FBS and 1% antibiotics. Cells were typically split every 3-5 days at a 1:10 dilution; (2) PC3 cells were cultured in RPMI media with 10% FBS and 1% antibiotics. Cells were typically split every 3-5 days at a 1:4 dilution; (3) MCF-7 cells were grown in K-12F media with 10% FBS and 1% antibiotics. Cells were typically split every 3-5 days at a 1:10 dilution.

TABLE IV

| Compound ID | Cell Viability % inhibition A2780 (20 uM Cpd) | Cell Viability % inhibition A2780 (4 uM Cpd) | Cell Viability % inhibition MCF-7 (20 uM Cpd) | Cell Viability % inhibition MCF-7 (4 uM Cpd) | Cell Viability % inhibition PC3 (20 uM Cpd) | Cell Viability % inhibition PC3 (4 uM Cpd) |
|---|---|---|---|---|---|---|
| 1 | 93.6 | 84.2 | 68.4 | 46.1 | 72.2 | 59.1 |
| 2 | 65.2 | 19.5 | ND | ND | 17.4 | 4.9 |
| 3 | 90.2 | 84.8 | 56.8 | 50.6 | 68.3 | 60.9 |
| 4 | 87.5 | 79.7 | ND | ND | 44.2 | 36.0 |
| 5 | 17.0 | 13.6 | ND | ND | 15.3 | 2.3 |
| 6 | 76.4 | 75.5 | ND | ND | 29.9 | 27.0 |
| 7 | 90.9 | 81.3 | ND | ND | 41.8 | 44.1 |
| 8 | 90.8 | 89.8 | 74.5 | 68.7 | 71.7 | 71.6 |
| 9 | 90.64 | 92.49 | 75.49 | 70.94 | 76.68 | 70.68 |
| 10 | 95.25 | 92.73 | 86.43 | 61.35 | 87.26 | 71.83 |
| 11 | 97.8 | 85.0 | 88.9 | 58.6 | 83.8 | 70.0 |
| 12 | 91.3 | 82.7 | 69.8 | 53.7 | 69.2 | 59.7 |
| 13 | 47.2 | 9.3 | 0.2 | 4.5 | 17.5 | 19.2 |
| 14 | 71.4 | 51.2 | 30.3 | 19.1 | 43.3 | 23.9 |
| 15 | 73.4 | 68.8 | 25.6 | 34.5 | 48.2 | 40.8 |
| 16 | 92.1 | 90.4 | 78.4 | 70.2 | 77.7 | 73.7 |
| 17 | 91.7 | 84.5 | 75.5 | 56.3 | 81.7 | 62.8 |
| 18 | 91.5 | 88.5 | 75.4 | 58.8 | 76.5 | 66.2 |
| 19 | 91.8 | 83.2 | 69.6 | 56.4 | 75.2 | 62.2 |
| 20 | 91.1 | 84.0 | 61.2 | 56.3 | 69.4 | 59.9 |
| 21 | 62.4 | 70.4 | ND | ND | 15.3 | 22.8 |
| 22 | 67.9 | 69 | ND | ND | 11.5 | 20.7 |
| 23 | 80.3 | 71.5 | ND | ND | 66.2 | 53.7 |
| 24 | 72.2 | 73.4 | ND | ND | 67.5 | 53.1 |
| 25 | 81.1 | 70.6 | ND | ND | 63.4 | 50.3 |
| 26 | 79.9 | 76 | ND | ND | 67.5 | 59.3 |
| 27 | 77.4 | 77.3 | ND | ND | 69.6 | 58.3 |
| 28 | 74.2 | 77 | ND | ND | 65.6 | 58.9 |
| 29 | 83.1 | 74.4 | ND | ND | 69.5 | 60.5 |
| 30 | 78.7 | 77.4 | ND | ND | 71.9 | 63.4 |
| 31 | 71.2 | 70.9 | ND | ND | 43.7 | 51.8 |
| 32 | 77 | 71.9 | ND | ND | 57.6 | 57.3 |
| 33 | 74.8 | 69.5 | ND | ND | 54.9 | 56.1 |
| 34 | 49.4 | 51.6 | ND | ND | 30.3 | 19.8 |
| 35 | 75.9 | 54.6 | ND | ND | 58.8 | 39.6 |
| 36 | 55.5 | 51.3 | ND | ND | 42.5 | 24.3 |
| 37 | 70.8 | 59.2 | ND | ND | 61 | 35.4 |
| 38 | 68.7 | 51.7 | ND | ND | 61.2 | 39.9 |
| 39 | 58.7 | 55.6 | ND | ND | 28.7 | 19.2 |
| 40 | 72 | 61 | ND | ND | 52.5 | 48.3 |
| 41 | 88.9 | 74.7 | ND | ND | 80.9 | 74.5 |
| 42 | 85.2 | 85 | ND | ND | 84.5 | 80.3 |
| 43 | 86.7 | 82.6 | ND | ND | 84.5 | 75.1 |
| 44 | 86.1 | 86.5 | ND | ND | 84.6 | 81.8 |
| 45 | 86.4 | 87.6 | ND | ND | 83.3 | 80.8 |
| 46 | 71.8 | 71.1 | ND | ND | 67.6 | 68.5 |
| 47 | 95.5 | 88.7 | 64.6 | 40.6 | 78.6 | 63.2 |
| 48 | 88.8 | 79.2 | 47.8 | 36.5 | 67.0 | 72.0 |
| 49 | 59.5 | 16.9 | 48.3 | 28.1 | 39.7 | 19.4 |
| 50 | 62.6 | 7.3 | 40.7 | 10.0 | 54.7 | 39.2 |
| 51 | 76.0 | 6.8 | 49.5 | 22.9 | 65.7 | 17.3 |
| 52 | 69.5 | 8.0 | 22.2 | −1.6 | 52.5 | 35.0 |
| 53 | 74.8 | 15.1 | 39.6 | 11.3 | 67.1 | 12.3 |
| 54 | 64.6 | −6.4 | 42.6 | 23.8 | 34.8 | 0.2 |
| 55 | 87.4 | 80.3 | ND | ND | 82.2 | 81.1 |
| 56 | 97.6 | 88.0 | ND | ND | 97.4 | 81.4 |
| 57 | 89.8 | 88.3 | ND | ND | 89.0 | 85.1 |
| 58 | 91.1 | 86.6 | ND | ND | 93.6 | 77.7 |
| 59 | 90.4 | 87.8 | ND | ND | 88.5 | 82.6 |
| 60 | 83.7 | 77.1 | ND | ND | 80.6 | 48.8 |
| 61 | 89.7 | 86.5 | 72.9 | 73.3 | 70.6 | 58.3 |
| 62 | 89.9 | 85.2 | 67.0 | 59.4 | 65.1 | 54.8 |
| 63 | 88.0 | 85.6 | 65.1 | 59.1 | 67.6 | 61.4 |
| 64 | 81.5 | 80.0 | 74.5 | 73.5 | 62.7 | 59.4 |
| 65 | 89.8 | 85.9 | ND | ND | 82.2 | 80.5 |
| 66 | 88.4 | 89.0 | 76.0 | 75.0 | 70.6 | 66.0 |
| 67 | 87.9 | 87.1 | 63.7 | 60.0 | 61.6 | 56.0 |
| 68 | 89.0 | 87.1 | 59.3 | 54.3 | 64.4 | 58.4 |

TABLE IV-continued

| Compound ID | Cell Viability % inhibition A2780 (20 uM Cpd) | Cell Viability % inhibition A2780 (4 uM Cpd) | Cell Viability % inhibition MCF-7 (20 uM Cpd) | Cell Viability % inhibition MCF-7 (4 uM Cpd) | Cell Viability % inhibition PC3 (20 uM Cpd) | Cell Viability % inhibition PC3 (4 uM Cpd) |
|---|---|---|---|---|---|---|
| 69 | 90.1 | 84.7 | 61.3 | 56.2 | 64.5 | 57.6 |
| 70 | 87.8 | 86.3 | 66.1 | 61.1 | 65.0 | 58.4 |

The invention claimed is:

1. A compound or salt of formula III

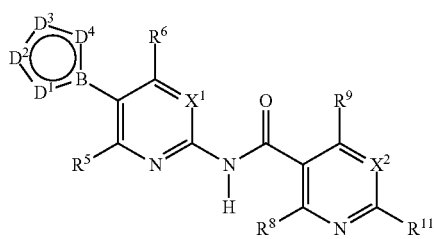

wherein
$X^1$ is selected from N and $CR^7$;
$X^2$ is selected from N and $CR^{10}$;
each of $D^1$, $D^2$, $D^3$, and $D^4$ is selected from $CR^1$, $CR^2$, $CR^3$, $CR^4$, N, O, and S;
B is C;
each of $R^1$, $R^2$, $R^3$, and $R^4$ is independently selected from —H, halogen, substituted or unsubstituted $C_{1-8}$ alkyl, substituted or unsubstituted $C_{3-6}$ cycloalkyl, substituted or unsubstituted $C_{2-8}$ alkenyl, substituted or unsubstituted $C_{2-8}$ alkynyl, —CN, —NO$_2$, —C(O)R$^A$, —CO$_2$R$^A$, —C(O)NR$^A$R$^B$, —OR$^A$, —OC(O)R$^A$, —OC(O)NR$^A$R$^B$, —NR$^C$C(O)R$^A$, —NR$^C$C(O)NR$^A$R$^B$, —NR$^A$R$^B$, —NR$^C$CO$_2$R$^A$, —NR$^C$S(O)$_2$R$^A$, —SR$^A$, —S(O)R$^A$, —S(O)$_2$R$^A$, —S(O)$_2$NR$^A$R$^B$, substituted or unsubstituted $C_{6-10}$ aryl, and substituted or unsubstituted 3- to 10-membered heterocyclyl;
each of $R^6$, $R^7$, $R^{10}$, and $R^{11}$ is independently selected from —H, halogen, substituted or unsubstituted $C_{1-8}$ alkyl, substituted or unsubstituted $C_{2-8}$ alkenyl, substituted or unsubstituted $C_{2-8}$ alkynyl, —CN, —NO$_2$, —C(O)R$^A$, —CO$_2$R$^A$, —C(O)NR$^A$R$^B$, —OR$^A$, —OC(O)R$^A$, —OC(O)NR$^A$R$^B$, —NR$^C$C(O)R$^A$, —NR$^C$C(O)NR$^A$R$^B$, —NR$^A$R$^B$, —NR$^C$CO$_2$R$^A$, —NR$^C$S(O)$_2$R$^A$, —SR$^A$, —S(O)R$^A$, —S(O)$_2$R$^A$, —S(O)$_2$NR$^A$R$^B$, substituted or unsubstituted $C_{6-10}$ aryl, substituted or unsubstituted 5- to 10-membered heteroaryl, and substituted or unsubstituted 3- to 10-membered heterocyclyl;
$R^5$ is selected from —H, halogen, substituted or unsubstituted $C_{1-8}$ alkyl, substituted or unsubstituted $C_{2-8}$ alkenyl, substituted or unsubstituted $C_{2-8}$ alkynyl, —CN, —NO$_2$, —C(O)R$^A$, —CO$_2$R$^A$, —C(O)NR$^A$R$^B$, —OR$^A$, —OC(O)R$^A$, —OC(O)NR$^A$R$^B$, —NR$^C$C(O)R$^A$, —NR$^C$C(O)NR$^A$R$^B$, —NR$^C$CO$_2$R$^A$, —NR$^C$S(O)$_2$R$^A$, —SR$^A$, —S(O)R$^A$, —S(O)$_2$R$^A$, —S(O)$_2$NR$^A$R$^B$, substituted or unsubstituted $C_{6-10}$ aryl, substituted or unsubstituted 5- to 10-membered heteroaryl, and substituted or unsubstituted 3- to 10-membered heterocyclyl;
each of $R^8$ and $R^9$ is independently selected from —H, halogen, —OR$^A$, —NH$_2$, —NO$_2$, —O(CO)R$^A$, —O(CO)NR$^A$R$^B$, —SH, and —SR$^A$;
each of $R^A$, $R^B$, and $R^C$, when present, is independently selected from —H, halogen, substituted or unsubstituted $C_{1-8}$ alkyl, substituted or unsubstituted $C_{3-6}$ cycloalkyl, substituted or unsubstituted $C_{2-8}$ alkenyl, substituted or unsubstituted $C_{2-8}$ alkynyl, —CN, =O, —NO$_2$, —OR', —OC(O)R', —CO$_2$R', —C(O)R', —C(O)NR'R", —OC(O)NR'R", —NR'''C(O)R', —NR'''C(O)NR'R", —NR'R", —NR'''CO$_2$R', —SR', —S(O)R', —S(O)$_2$R', —S(O)$_2$NR'R", —NR'S(O)$_2$R", substituted or unsubstituted $C_{6-10}$ aryl, substituted or unsubstituted 5- to 10-membered heteroaryl and substituted or unsubstituted 3- to 10-membered heterocyclyl;
R', R", and R'" are each independently selected from —H, unsubstituted $C_{1-4}$ alkyl, and substituted or unsubstituted $C_{3-6}$ cycloalkyl or R' and R" together with the atoms which they substitute form a substituted or unsubstituted 5-, 6-, or 7-membered ring;
provided that when B and $D^1$ are N, then $D^2$ and $D^4$ cannot be C-pyridin-3-yl or C-trifluoromethyl.

2. A compound or salt selected from the group consisting of:

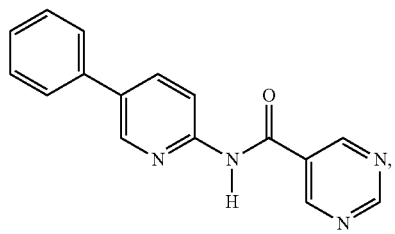

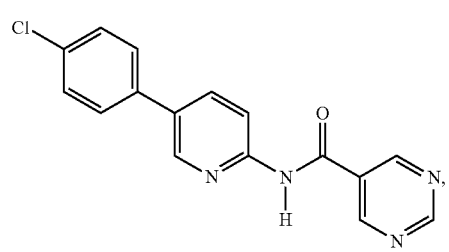

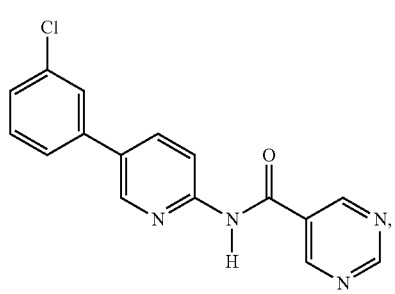

-continued
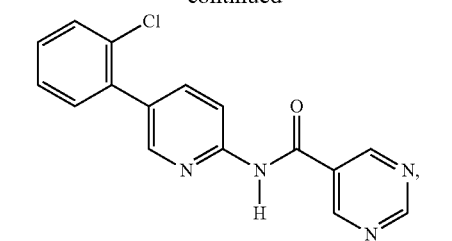
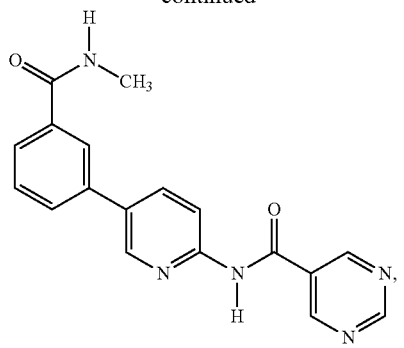
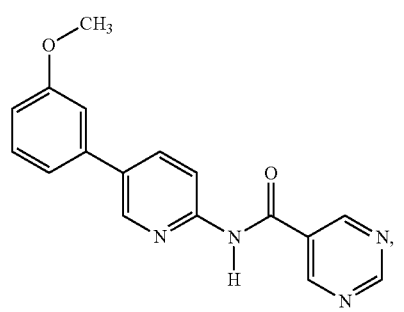
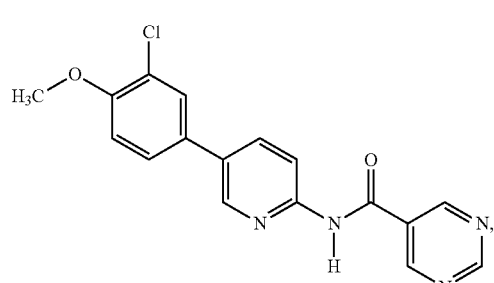
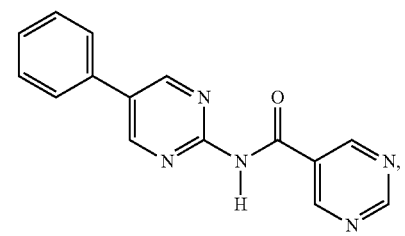
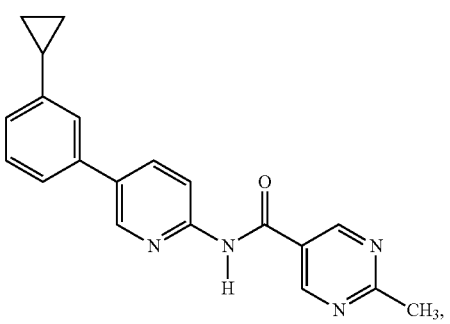
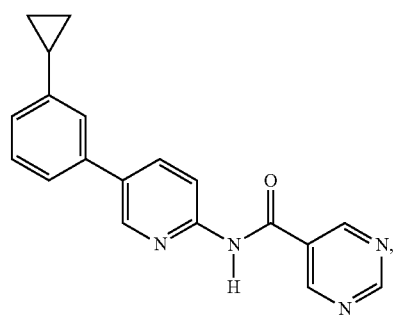

113
-continued
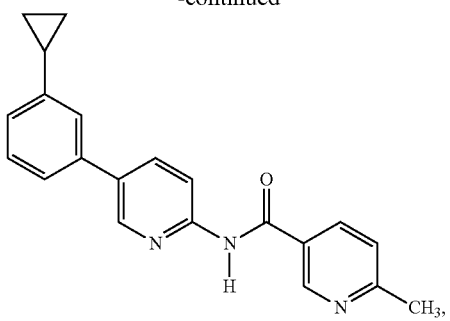
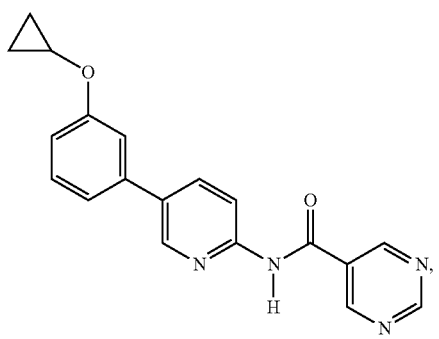
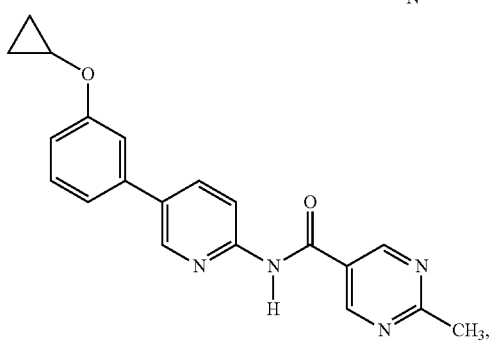
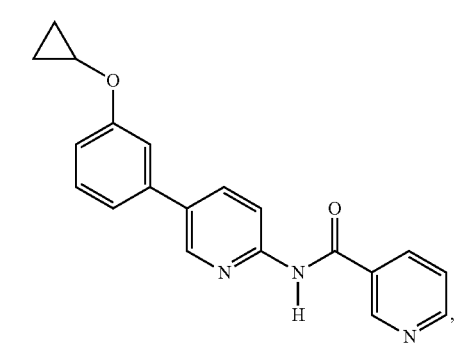
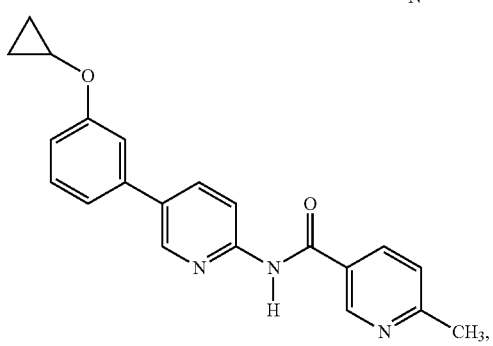
114
-continued
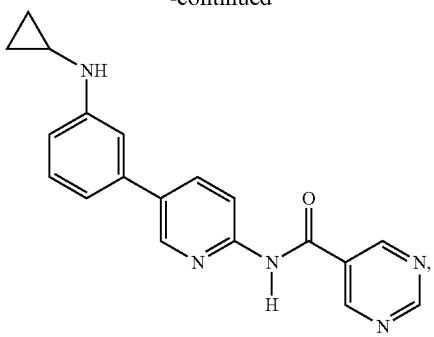
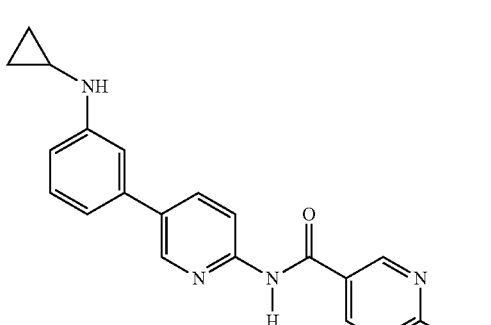
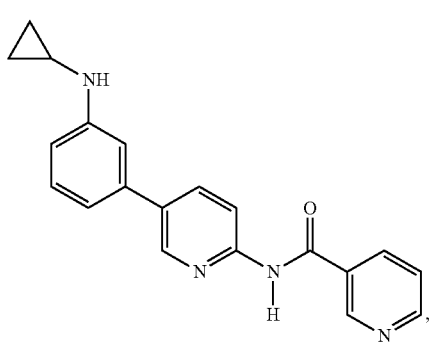
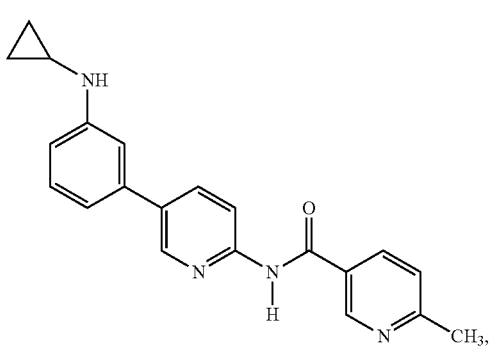
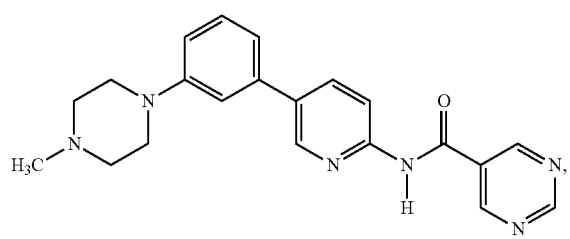

-continued
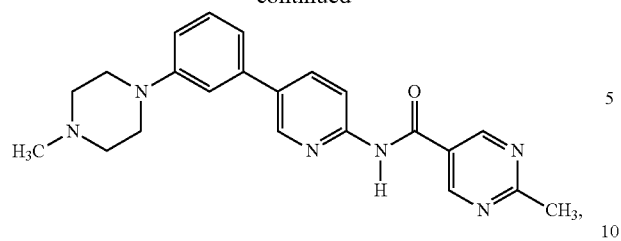
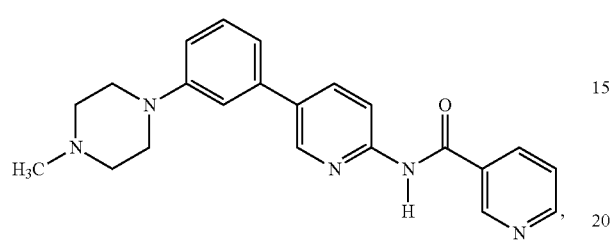
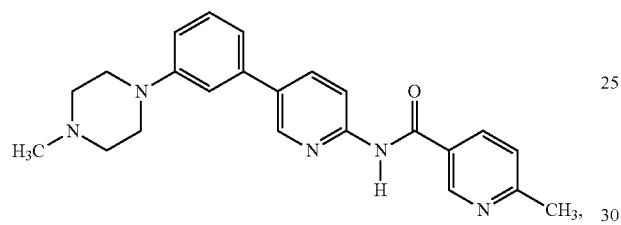
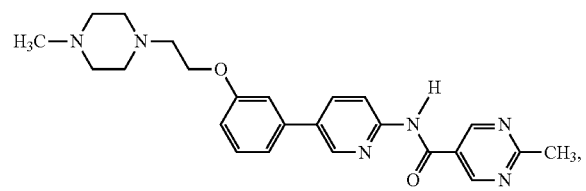
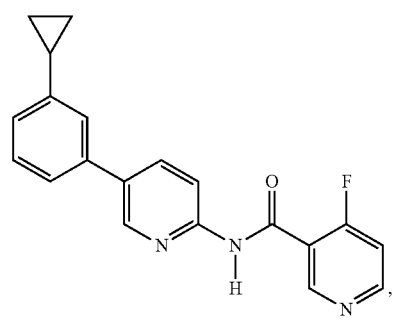
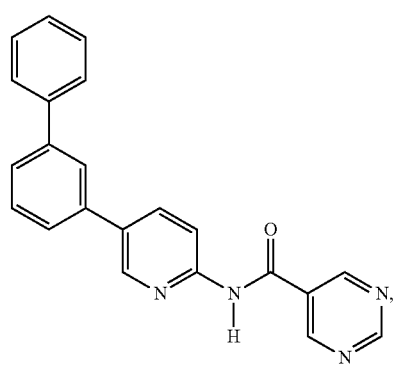
-continued
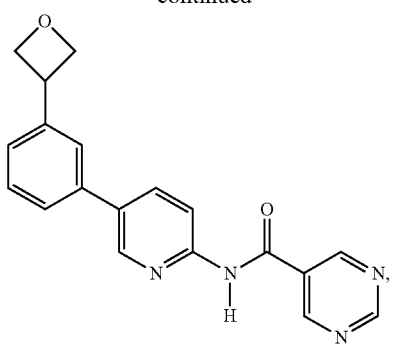
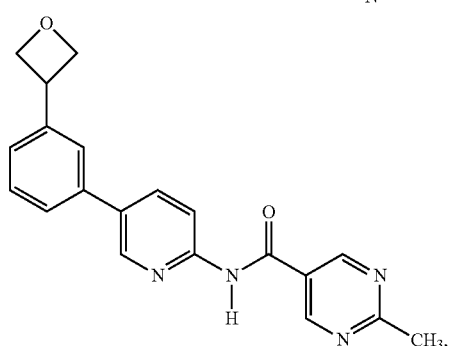
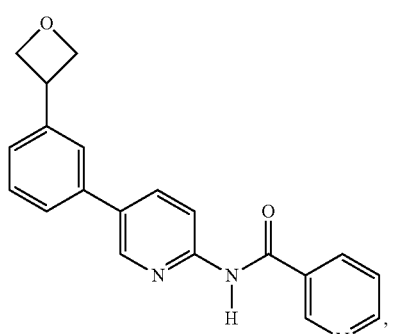
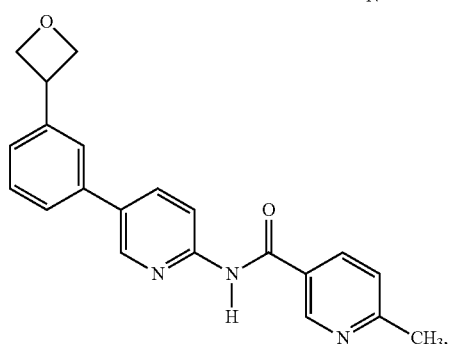
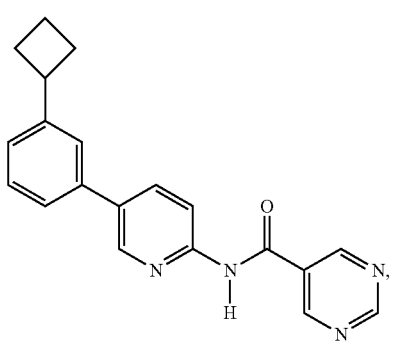

117
-continued
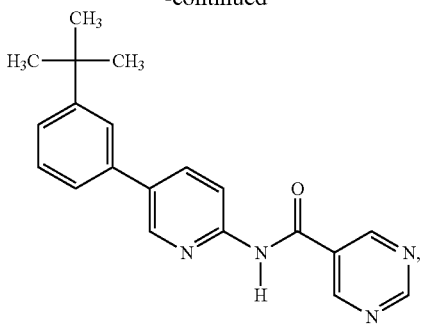
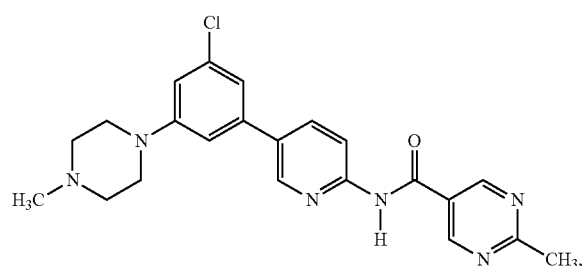
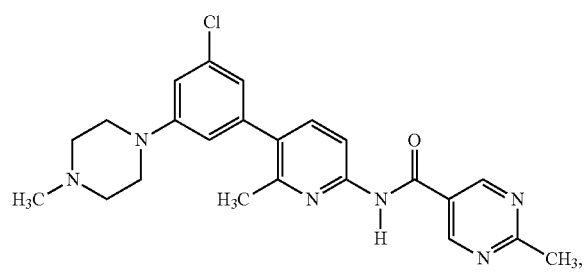
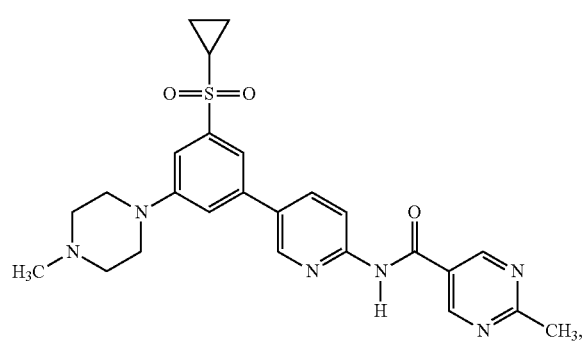
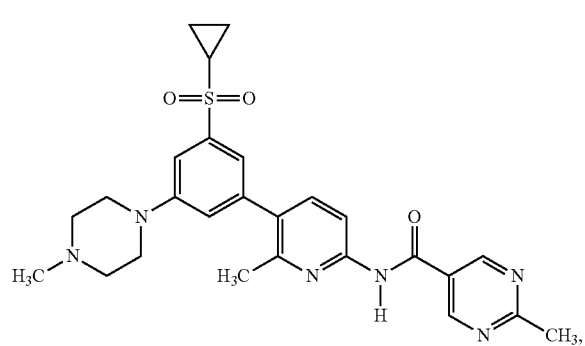
118
-continued
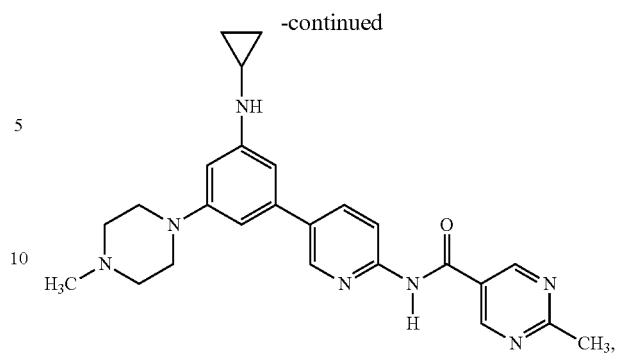
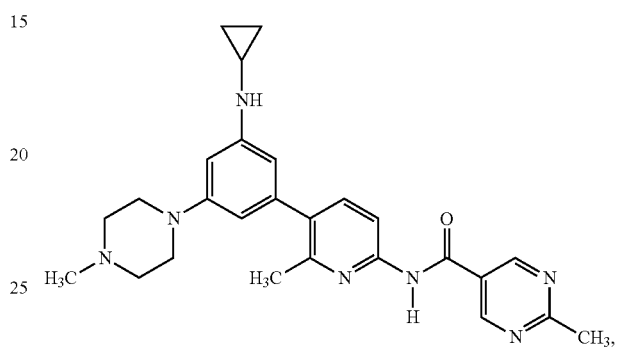
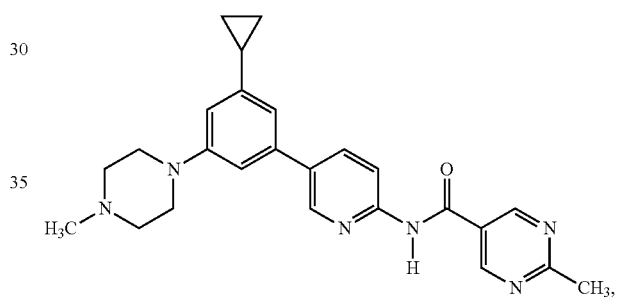
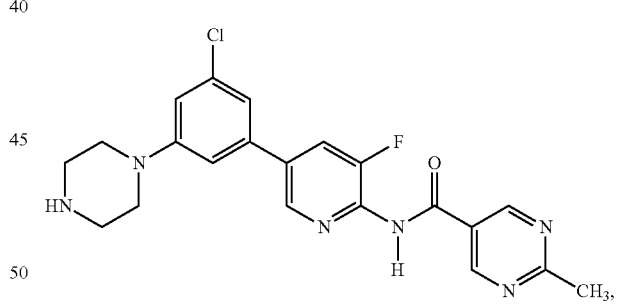
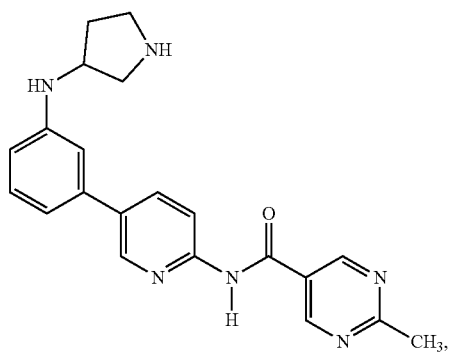

-continued
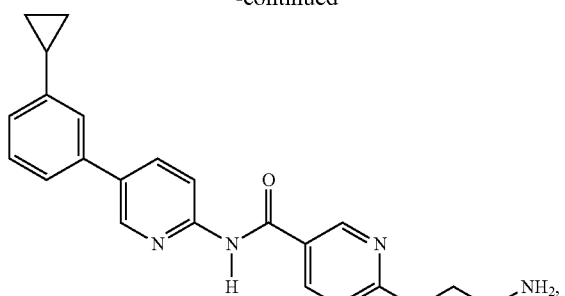
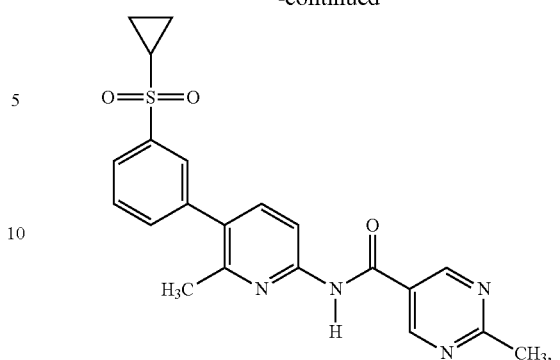
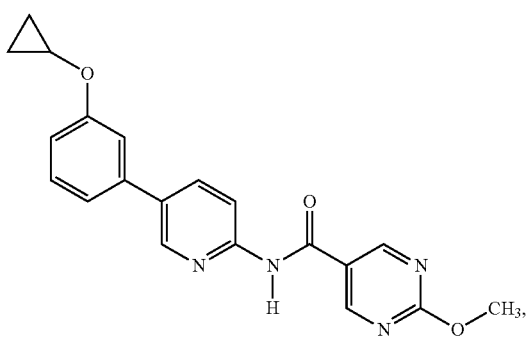
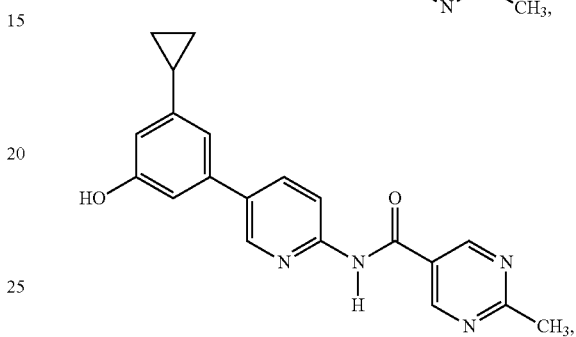
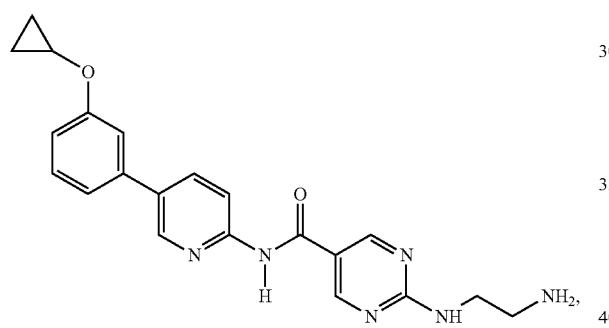
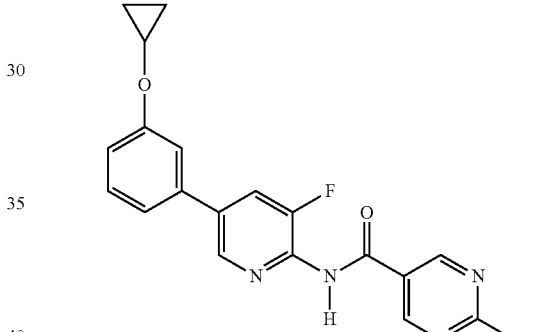
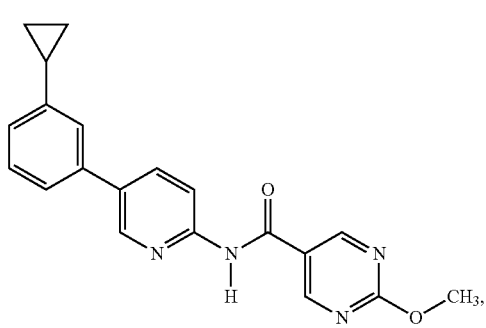
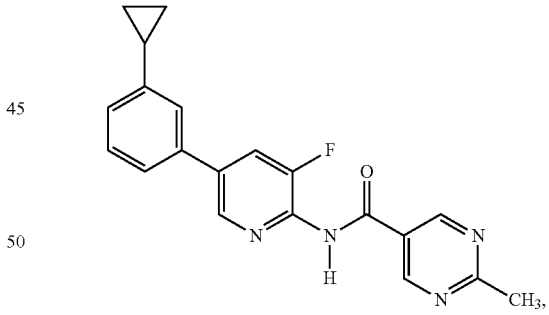
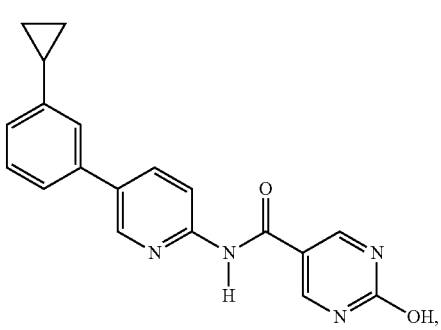
and -continued

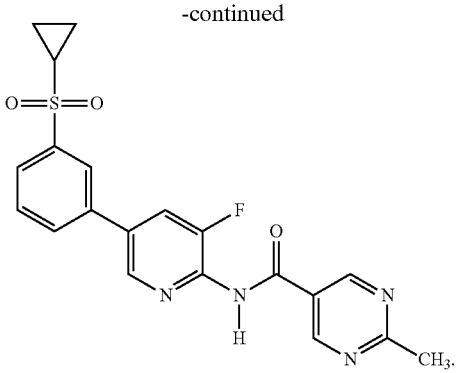

3. A pharmaceutical composition comprising a compound of claim 2 and a pharmaceutically acceptable carrier or excipient.

4. A method of treating an proliferative disorder in a patient in need thereof, comprising administering a compound of claim 2 to the patient.

5. The method of claim 4, wherein the proliferative disorder is cancer and is selected from adrenal, anal, aplastic anemia, bile duct, bladder, bone, brain, breast, cervical, central nervous system, colon, endometrial, esophagial, ewing family, ocular, gallbladder, gastrointestinal carcinoid, gastrointestinal stromal, Kaposi sarcoma, kidney, laryngeal, leukemia, liver, lung, lymphomas, malignant mesothelioma, multiple myeloma, myelodysplastic syndrome, nasal cavity and paranasal sinus, nasopharyngeal, neuroblastoma, oral cavity and oropharyngeal, osteosarcoma, ovarian, pancreatic, penile, pituitary, prostate, rectal, retinoblastoma, rhabdomyosarcoma, salivary, sarcoma, skin, small intestine, stomach, testicular, thymus, thyroid, uterine sarcoma, vaginal, and Wilms tumor cancers.

6. The method of claim 4, wherein the proliferative disorder is a gastric cancer.

7. The method of claim 4, wherein the proliferative disorder is selected from Castleman disease, gestational trophoblastic disease, and Hodgkins disease.

8. A compound or salt of formula II

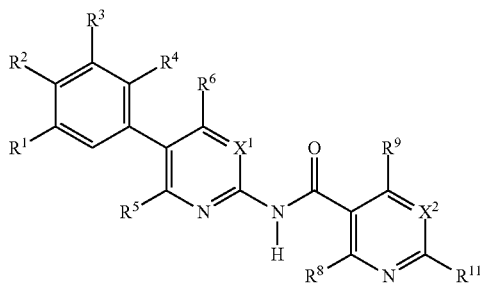

(II)

wherein
 $X^1$ is selected from N and $CR^7$;
 $X^2$ is selected from N and $CR^{16}$;
 each of $R^1$, $R^3$, and $R^4$ is independently selected from —H, halogen, substituted or unsubstituted $C_{1-8}$ alkyl, substituted or unsubstituted $C_{3-6}$ cycloalkyl, substituted or unsubstituted $C_{2-8}$ alkenyl, substituted or unsubstituted $C_{2-8}$ alkynyl, —CN, —NO$_2$, —C(O)R$^A$, —CO$_2$R$^A$, —C(O)NR$^A$R$^B$, —OR$^A$, —OC(O)R$^A$, —OC(O)NR$^A$R$^B$, —NR$^C$C(O)R$^A$, —NR$^C$C(O)NR$^A$R$^B$, —NR$^A$R$^B$, —NR$^C$CO$_2$R$^A$, —NR$^C$S(O)$_2$R$^A$, —SR$^A$, —S(O)R$^A$, —S(O)$_2$R$^A$, —S(O)$_2$NR$^A$R$^B$, substituted or unsubstituted $C_{6-10}$ aryl, substituted or unsubstituted 5- to 10-membered heteroaryl, and substituted or unsubstituted 3- to 10-membered heterocyclyl;

$R^2$ is independently selected from —H, halogen, substituted or unsubstituted $C_{1-8}$ alkyl, substituted or unsubstituted $C_{3-6}$ cycloalkyl, substituted or unsubstituted $C_{2-8}$ alkenyl, substituted or unsubstituted $C_{2-8}$ alkynyl, —CN, —NO$_2$, —C(O)R$^A$, —CO$_2$R$^A$, —C(O)NR$^A$R$^B$, —OR$^A$, —OC(O)R$^A$, —OC(O)NR$^A$R$^B$, —NR$^C$C(O)R$^A$, —NR$^C$C(O)NR$^A$R$^B$, —NR$^A$R$^B$, —NR$^C$CO$_2$R$^A$, —NR$^C$S(O)$_2$R$^A$, —SR$^A$, —S(O)R$^A$, —S(O)$_2$R$^A$, —S(O)$_2$NR$^A$R$^B$, substituted or unsubstituted $C_{6-10}$ aryl, substituted or unsubstituted 5- to 10-membered heteroaryl, and unsubstituted 3- to 10-membered heterocyclyl;

each of $R^5$, $R^6$, $R^7$, $R^{10}$, and $R^{11}$ is independently selected from —H, halogen, substituted or unsubstituted $C_{1-8}$ alkyl, substituted or unsubstituted $C_{2-8}$ alkenyl, substituted or unsubstituted $C_{2-8}$ alkynyl, —CN, —NO$_2$, —C(O)R$^A$, —CO$_2$R$^A$, —C(O)NR$^A$R$^B$, —OR$^A$, —OC(O)R$^A$, —OC(O)NR$^A$R$^B$, —NR$^C$C(O)R$^A$, —NR$^C$C(O)NR$^A$R$^B$, —NR$^A$R$^B$, —NR$^C$CO$_2$R$^A$, NR$^C$S(O)$_2$R$^A$, SR$^A$, S(O)R$^A$, S(O)$_2$R$^A$, S(O)$_2$NR$^A$R$^B$, substituted or unsubstituted $C_{6-10}$ aryl, substituted or unsubstituted 5- to 10-membered heteroaryl, and substituted or unsubstituted 3- to 10-membered heterocyclyl;

each of $R^8$ and $R^9$ is independently selected from —H, halogen, —OR$^A$, —NH$_2$, —NO$_2$, —O(CO)R$^A$, —O(CO)NR$^A$R$^B$, —SH, and —SR$^A$;

each of $R^A$, $R^B$, and $R^C$, when present, is independently selected from —H, halogen, substituted or unsubstituted $C_{1-8}$ alkyl, substituted or unsubstituted $C_{3-6}$ cycloalkyl, substituted or unsubstituted $C_{2-8}$ alkenyl, substituted or unsubstituted $C_{2-8}$ alkynyl, —CN, =O, —NO$_2$, —OR', —OC(O)R', —CO$_2$R', —C(O)R', —C(O)NR'R", —OC(O)NR'R", —NR'"C(O)R', —NR'"C(O)NR'R", —NR'R", —NR'"CO$_2$R', —SR', —S(O)R', —S(O)$_2$R', —S(O)$_2$NR'R", —NR'S(O)$_2$R", substituted or unsubstituted $C_{6-10}$ aryl, substituted or unsubstituted 5- to 10-membered heteroaryl and substituted or unsubstituted 3- to 10-membered heterocyclyl;

R', R", and R'" are each independently hydrogen, unsubstituted $C_{1-4}$ alkyl, and substituted or unsubstituted $C_{3-6}$ cycloalkyl or R' and R" together with the atoms which they substitute form a substituted or unsubstituted 5-, 6-, or 7-membered ring;

provided that when $X^1$ is N, $X^2$ is CH, and each of $R^1$, $R^2$, $R^3$, $R^4$, $R^8$, $R^9$, and $R^{11}$ is hydrogen, then $R^5$ and $R^6$ cannot both be Cl or OCH$_3$;

provided that when $X^1$ and $X^2$ are both CH, then at least one of $R^1$, $R^2$, $R^3$, $R^4$, $R^5$, $R^6$, $R^8$, $R^9$, and $R^{11}$ is not hydrogen; and provided that when $X^1$ is CH, $X^2$ is C—Cl, and $R^{11}$ is Cl or O-isopropyl, then at least one of $R^1$, $R^2$, $R^3$, $R^4$, $R^5$, $R^6$, $R^8$, and $R^9$ is not hydrogen.

9. The compound or salt of claim 8, wherein each of $R^1$, $R^3$, and $R^4$ is independently selected from —H, halogen, substituted or unsubstituted $C_{1-8}$ alkyl, substituted or unsubstituted $C_{3-6}$ cycloalkyl, —C(O)NR$^A$R$^B$, —OR$^A$, —NR$^A$R$^B$, substituted or unsubstituted 5- to 10-membered heteroaryl, and substituted or unsubstituted 3- to 10-membered heterocyclyl.

10. The compound or salt of claim 8, wherein at least one of $R^1$, $R^2$, $R^3$, and $R^4$ is halogen, substituted or unsubstituted $C_{1-8}$ alkyl, substituted or unsubstituted $C_{3-6}$ cycloalkyl, —C(O)NR$^A$R$^B$, —OR$^A$, —NR$^A$R$^B$, —S(O)$_2$R$^A$, substituted or unsubstituted 5- to 10-membered heteroaryl, or unsubstituted 3- to 10-membered heterocyclyl.

11. The compound or salt of claim 8, wherein
$R^1$ is selected from H, chloro, trifluoromethyl, cyclopropyl, —(C=O)NHCH$_3$, —OCH$_3$, —O-cyclopropyl, —NH-cyclopropyl, 1-methyl-piperazin-1-yl, 4-methyl-piperazin-1-yl)ethoxyl, phenyl, oxetan-3-yl, cyclobutyl, tert-butyl, —S(O)$_2$-cyclopropyl, piperazin-1-yl, pyrrolidin-3-yl-amino, and —OH;
$R^2$ is selected from H, chloro, and —OCH$_3$;
$R^3$ is selected from —H, chloro, cyclopropyl, —(C=O)NHCH$_3$, —OCH$_3$, —O-cyclopropyl, —NH-cyclopropyl, —S(O)$_2$-cyclopropyl, 1-methyl-piperazin-1-yl, 4-methylpiperazin-1-yl)ethoxyl, phenyl, oxetan-3-yl, cyclobutyl, tert-butyl, —S(O)$_2$-cyclopropyl, piperazin-1-yl, pyrrolidin-3-yl-amino, and —OH; and
$R^4$ is selected from —H, chloro, trifluoromethyl, and —OCH$_3$;
wherein at least one of $R^1$, $R^2$, $R^3$, and $R^4$ is not —H.

12. The compound or salt of claim 8, wherein at least one of $R^1$ and $R^3$ is selected from —S(O)$_2$-cyclopropyl and 1-methyl-piperazin-1-yl.

13. The compound or salt of claim 8, wherein one of $R^1$ and $R^3$ is selected from —S(O)$_2$-cyclopropyl and 1-methyl-piperazin-1-yl and the other of $R^1$ and $R^3$ is selected from —H, —Cl, —S(O)$_2$-cyclopropyl, —NH-cyclopropyl, and cyclopropyl.

14. The compound or salt of claim 10, wherein at least one of $R^1$ and $R^3$ is
—O-cyclopropyl and the other of $R^1$ and $R^3$ is —H.

15. A pharmaceutical composition comprising a compound of claim 8 and a pharmaceutically acceptable carrier or excipient.

16. A method of treating a proliferative disorder in a patient in need thereof, comprising administering a compound of claim 8 to the patient.

17. The method of claim 16, wherein the proliferative disorder is cancer and is selected from adrenal, anal, aplastic anemia, bile duct, bladder, bone, brain, breast, cervical, central nervous system, colon, endometrial, esophagial, ewing family, ocular, gallbladder, gastrointestinal carcinoid, gastrointestinal stromal, Kaposi sarcoma, kidney, laryngeal, leukemia, liver, lung, lymphomas, malignant mesothelioma, multiple myeloma, myelodysplastic syndrome, nasal cavity and paranasal sinus, nasopharyngeal, neuroblastoma, oral cavity and oropharyngeal, osteosarcoma, ovarian, pancreatic, penile, pituitary, prostate, rectal, retinoblastoma, rhabdomyosarcoma, salivary, sarcoma, skin, small intestine, stomach, testicular, thymus, thyroid, uterine sarcoma, vaginal, and Wilms tumor cancers.

18. The method of claim 16, wherein the proliferative disorder is a gastric cancer.

19. The method of claim 16, wherein the proliferative disorder is selected from Castleman disease, gestational trophoblastic disease, and Hodgkins disease.

\* \* \* \* \*